US008383125B2

(12) United States Patent
Cocks et al.

(10) Patent No.: US 8,383,125 B2
(45) Date of Patent: Feb. 26, 2013

(54) ANTIMICROBIAL PROTEIN

(75) Inventors: Benjamin Cocks, Melbourne (AU); Jianghui Wang, Melbourne (AU); Jane Whitley, Melbourne (AU)

(73) Assignee: Agriculture Victoria Services Pty, Limited, Attwood, Victoria (AU)

( * ) Notice: Subject to any disclaimer, the term of this patent is extended or adjusted under 35 U.S.C. 154(b) by 633 days.

(21) Appl. No.: 12/294,000

(22) PCT Filed: Mar. 23, 2007

(86) PCT No.: PCT/AU2007/000367
§ 371 (c)(1),
(2), (4) Date: Jun. 4, 2009

(87) PCT Pub. No.: WO2007/106951
PCT Pub. Date: Sep. 27, 2007

(65) Prior Publication Data
US 2009/0312248 A1 Dec. 17, 2009

Related U.S. Application Data

(60) Provisional application No. 60/785,675, filed on Mar. 23, 2006.

(51) Int. Cl.
*A61K 39/00* (2006.01)
*A61K 38/00* (2006.01)
*A01N 63/00* (2006.01)
*A01N 25/34* (2006.01)
*C07K 1/00* (2006.01)
*C07K 14/00* (2006.01)
*C07K 17/00* (2006.01)
*C07K 2/00* (2006.01)
*C07K 4/00* (2006.01)
*C07K 5/00* (2006.01)
*C07K 7/00* (2006.01)
*C07K 16/00* (2006.01)

(52) U.S. Cl. ............... 424/185.1; 424/157.1; 424/184.1; 424/192.1; 424/134.1; 424/93.4; 424/802; 424/803; 424/404; 530/350; 530/300

(58) Field of Classification Search ........................ None
See application file for complete search history.

(56) References Cited

FOREIGN PATENT DOCUMENTS

| WO | WO 95/30751 | 11/1995 |
|---|---|---|
| WO | WO 96/32482 | 10/1996 |
| WO | WO 98/08534 | 3/1998 |
| WO | WO 03/091437 | 11/2003 |
| WO | WO 2005/033274 | 4/2005 |
| WO | WO 2005/033281 | 4/2005 |
| WO | WO 2005/077046 | 8/2005 |
| WO | WO 2007/106951 | 9/2007 |
| WO | WO 2007/142542 | 12/2007 |

OTHER PUBLICATIONS

Bowie et al. (Science, 1990, 257:1306-1310).*
Wallaby Holds the Secret to Combat Superbugs, pp. 1-3; Jun. 20, 2005; http://www2.prnewswire.com/cgi-bin/stories.pl?ACCT=104&STORY=/www/story/06-20-2005/0003925520&EDATE=;bcsi-ac-2160f1cfec5c399f=1DFA724E00000102eD6v+Hme7+i6JGHmzeZ5bYJvg5kVCwAAAg
EAAL6hKQCEAwAAAAAAAER4CwA=.*
Axelsson, et al. "Statistical Aspects of Cell Motility Determinations with a Modified Chemotaxis Assembly for Multiwell Filter Assays," *Journal of Immunological Methods*, vol. 46, pp. 251-258, 1981.
Brady, et al. "Reflections on a Peptide," *Nature*, vol. 368, pp. 692-693, Apr. 21, 10094.
Broadbent, et al. "Nisin Inhibits Several Gram-positive, Maestitis-causing Pathogens," *Journal of Dairy Science*, vol. 72, No. 12, pp. 3342-3345, 1989.
Chorev, et al. Recent Developments in Retro Peptides and Proteins—An Ongoing Topochemical Exploration, *Trends in Biotechnology*, vol. 13, pp. 438-445, 1995.
Clare, et al. "Bioactive Milk Peptides: A Prospectus," *Journal of Dairy Science*, vol. 83, No. 6, pp. 1187-1195, 2000.
Cowland, et al. "hCAP-18, a Cathelin/Pro-bactenecin-like Protein of Human Neutrophil Specific Granules," *FEBS Letters*, vol. 368, pp. 173-176, 1995.
Donovan, et al. "Peptidoglycan Hydrolase Fusions Maintain Their Parental Specificities," *Applied and Environmental Microbiology*, vol. 72, No. 4, pp. 2988-2996, Apr. 2006.
Goldman, "Evolution of the Mammary Gland Defense System and the Ontogeny of the Immune System" *Journal of Mammary Gland Biology and Neoplasia*, vol. 7, No. 3, pp. 277-289, Jul. 2002.
Goodman, et al. "On the Concept of Linear Modified Retro-peptide Structures," *Accounts of Chemical Research*, vol. 12, No. 1, pp. 1-7, Jan. 1979.
Hoeben, et al. "Effect of Bovine Somatotropin on Neutrophil Functions and Clinical Symptoms during *Streptococcus uberis* Mastitis," *Journal of Dairy Science*, vol. 82, No. 7, pp. 1465-1481, 1999.
Jameson, et al. "A Rationally Designed CD4 Analogue Inhibits Experimental Allergic Encephalomyelitis," *Nature*, vol. 368, pp. 744-746, Apr. 21, 1994.
Larrick, et al. "Human CAP18: A Novel Antimicrobial Lipopolysaccharide-binding Protein," *Infection and Immunity*, vol. 63, No. 4. pp. 1291-1297, Apr. 1995.
Lehrer, et al. Antimicrobial Peptides in Mammalian and Insect Host Defence, *Current Opinion in Immunology*, vol. 11, pp. 23-27, 1999.
Nagaoka, et al. "Augmentation of the Bactericidal Activities of Human Cathelicidin CAP18/LL-37-derived Antimicrobial Peptides by Amino Acid Substitutions," *Inflammation Research*, vol. 54, No. 2, pp. 66-73, 2005.
Old, et al. "The Effect of Oestrus and the Presence of Pouch Young on Aerobic Bacteria Isolated from the Pouch of the Tammar Wallaby, *Macropus eugenii*," *Comparative Immunology Microbiology & Infectious Diseases*, vol. 21, No. 4, pp. 237-245, 1998.
Peeters, et al. "Clinical Characteristics of Linezolid-resistant *Staphylococcus aureus* Infections," *The American Journal of the Medical Sciences*, vol. 330, No. 2, pp. 102-104, Aug. 2005.

(Continued)

*Primary Examiner* — Vanessa L Ford
*Assistant Examiner* — Lakia Tongue
(74) *Attorney, Agent, or Firm* — Knobbe, Martens, Olson & Bear, LLP

(57) ABSTRACT

The present invention provides improved antimicrobial compositions comprising peptide fragments of tammar wallaby milk proteins and analogs and derivatives thereof exemplified by the amino acid sequences of SEQ ID Nos: 1-40 and uses therefor in the treatment of a range of infections by bacteria and fungi. The antimicrobial compositions are particularly useful for broad spectrum applications, especially for the treatment of bacterial infections.

18 Claims, 7 Drawing Sheets

OTHER PUBLICATIONS

Sela, et al. "Different Roles of D-amino Acids in Immune Phenomena," *The FASEB Journal*, vol. 11, pp. 449-456, May 1997.

Sparo, et al. "In vitro Efficacy of the Novel Peptide CECT7121 Against Bacteria Isolated from Mastitic Dairy Cattle," *Letters in Applied Microbiology*, vol. 48, No. 2, pp. 187-192, 2009.

Steinberg, et al. "Designer Assays for Antimicrobial Peptides," *Methods in Molecular Biology*, vol. 78, pp. 169-188, 1997.

Swoboda, et al. "Varying Linezolid Susceptibility of Vancomycin-resistant *Enterococcus faecium* Isolates During Therapy: A Case Report," *Journal of antimicrobial Chemotherapy*, vol. 56, pp. 787-789, 2005.

Tang, et al. "Role of *Pseudomonas aeruginosa* Pili in Acute Pulmonary Infection," *Infection and Immunity*, vol. 63, No. 4, pp. 1278-1285, Apr. 1995.

Wall, et al. "Genetically Enhanced Cows Resist Intramammary *Staphylococcus aureus* Infection," *Nature Biotechnology*, vol. 23, No. 4, pp. 445-451, Apr. 2005.

Wang, et al. "Mammary Gland and Innate Immunity of the Tammar Wallaby," *Tissue Antigens*, vol. 66, No. 5, p. 583, Abstract 656.

Yaoita, et al. "Apoptosis in Relevant Clinical Situations: Contribution of Apoptosis in Myocardial Infarction," *Cardiovascular Research*, vol. 45, No. 3, pp. 630-641, 2000.

Zhang, et al. "Interaction of Cationic Antimicrobial Peptides with Model Membranes," *The Journal of Biological Chemistry*, vol. 276, No. 38, pp. 35714-35722, 2001.

Wang, J. et al. "Mammary gland and innate immunity of the tammar wallaby", Tissue Antigens, 2005, vol. 66, No. 5, p. 583, Abstract 656. Meeting Info: 35th Annual Scientific Meeting of the Australasian Society for Immunology/14th International HLA and Immunogenetics Workshops, Melbourne, Australia Nov. 29-Dec. 2, 2005. Australasian Soc. Immunol.

Old, J M, et al, "The effect of oestrus and the presence of pouch young on aerobic bacteria isolated from the pouch of the tammar wallaby, Macropus eugenii", Comparative Immunology, Microbiology & Infectious Diseases, 1998, vol. 21, No. 4, pp. 237-245.

The International Search Report corresponding to International Application No. PCT/AU2007/000367.

Marshall, S.H et al., *Molecular Biology and Genetics*, vol. 6, No. 3 (2003).

McPhee, J.B. et al., *Journal of Peptide Science*, in Press (2005).

Oppenheim, J,J. et al., Annals of the Rheumatic. Diseases, vol. 62, Supplement II, ii17-ii21 (2003).

Smet, K.D. et al., Biotechnology Letters, vol. 27, pp. 1337-1347 (2005).

Zanetti, M., Journal of Leukocyte Biology, vol. 75, pp. 39-48 (2004).

Zanetti, M. et al., Current Pharmaceutical Design, vol. 8, pp. 779-793 (2002).

* cited by examiner

| SEQ ID NO: | SEQ ID NO: | SEQ ID NO: | SEQ ID NO: |
| 9 | 11 | 13 | 17 |

ANTIMICROBIAL PROTEIN

RELATED APPLICATIONS

This application is the U.S. National Phase filing under 35 U.S.C. §371 of PCT/AU2007/000367, filed Mar. 23, 2007, entitled "Antimicrobial Protein", which designated the United States and was published in English on Sep. 27, 2007, which claims priority under 35 U.S.C. §119(e) to U.S. Provisional Patent Application No. 60/785,675, filed Mar. 23, 2006, the contents of which are incorporated herein by reference.

FIELD OF THE INVENTION

The present invention relates to antimicrobial peptides and uses thereof.

BACKGROUND OF THE INVENTION

General

The following publications provide conventional techniques of molecular biology, microbiology, virology, recombinant DNA technology, peptide synthesis in solution, solid phase peptide synthesis, and immunology. Such procedures are described, for example, in the following texts that are incorporated by reference:
1. Sambrook, Fritsch & Maniatis, Molecular Cloning: A Laboratory Manual, Cold Spring Harbor Laboratories, New York, Second Edition (1989), whole of Vols I, II, and III;
2. DNA Cloning: A Practical Approach, Vols. I and II (D. N. Glover, ed., 1985), IRL Press, Oxford, whole of text;
3. Oligonucleotide Synthesis: A Practical Approach (M. J. Gait, ed., 1984) IRL Press, Oxford, whole of text, and particularly the papers therein by Gait, pp 1-22; Atkinson et al., pp 35-81; Sproat et al., pp 83-115; and Wu et al., pp 135-151;
4. Animal Cell Culture: Practical Approach, Third Edition (John R. W. Masters, ed., 2000), ISBN 0199637970, whole of text;
5. J. F. Ramalho Ortigão, "The Chemistry of Peptide Synthesis" In: Knowledge database of Access to Virtual Laboratory website (Interactiva, Germany);
6. Sakakibara, D., Teichman, J., Lien, E. Land Fenichel, R. L. (1976). *Biochem. Biophys. Res. Commun.* 73 336-342;
7. Merrifield, R. B. (1963). *J. Am. Chem. Soc.* 85, 2149-2154.
8. Barany, G. and Merrifield, R. B. (1979) in *The Peptides* (Gross, E. and Meienhofer, J. eds.), vol. 2, pp. 1-284, Academic Press, New York.
9. Wünsch, E., ed. (1974) *Synthese von Peptiden in Houben-Weyls Metoden der Organischen Chemie* (Müler, E., ed.), vol. 15, 4th edn., Parts 1 and 2, Thieme, Stuttgart.
10. Bodanszky, M. (1984) *Principles of Peptide Synthesis*, Springer-Verlag, Heidelberg.
11. Bodanszky, M. & Bodanszky, A. (1984) *The Practice of Peptide Synthesis*, Springer-Verlag, Heidelberg.

DESCRIPTION OF THE RELATED ART

The discovery of penicillin in the 1930s and the subsequence discovery of other classes of antibiotics is estimated to have increased average life expectancy by up to ten years (McDermott et al, *Johns Hopkins Med. J.,* 151: 302-312, 1982). However, widespread misuse of antibiotics in recent years has lead to the rapid emergence of antibiotic-resistant pathogens (Zanetti et al., *Current Pharmaceutical Design,* 8: 779-793, 2002). For example, according to the World Health Organisation (WHO), approximately 70% of chest infections in developing countries may be resistant to at least one antimicrobial. Furthermore, *Pseudomonas, Klebsiella*, methicillin-resistant *Staphylococcus aureus* (MRSA) and vancomycin-resistant *Enterococcus* (VRE) having high levels of resistance are common pathogens in all parts of the world.

This problem is further exacerbated by the almost negligible progress in the development of new classes of antimicrobials. In fact, until the introduction of linezolid in 2000, there had not been a new class of antibiotics introduced to the market since the 1960s (McPhee and Hancock, *J. Peptide Sci.,* 11: 677-687, 2005).

In any event, since the introduction of linezolid, resistant strains of *S. aureus* and *Enterococcus faecium* have been identified in hospitalized patients (Swoboda et al., Antimicrob. Chemother. 56: 787-9, 2005 and Peeters and Sarria Am. J. Med. Sci., 330: 102-4, 2005).

Although previously considered to be relatively avirulent, the *Acinetobacter calcoaceticus-baumannii* complex is emerging as a problematic, multidrug-resistant, nosocomial and community-acquired pathogen. For example, *Acinetobacter* species cause hospital-acquired pneumonia, bloodstream infection, surgical site infection, and urinary tract infection. Risk factors for development of *A. baumannii* infection include alcoholism, smoking, chronic lung disease, and/or invasive procedures. Although the organism can cause suppurative infection in virtually any organ system, patients receiving mechanical ventilation are at special risk for hospital-acquired pneumonia caused by *Acinetobacter* species. Acinetobacter species are also involved in war-related injuries e.g., osteomyelitis and/or wound infection and/or bacteremia following wound infection. Many of the isolates are multidrug resistant and, in some parts of the United States, many isolates are now resistant to all aminoglycosides, cephalosporins, and fluoroquinolones. Colistin, previously abandoned in clinical use because of an unacceptably high rate of renal toxicity, is currently the most reliably active agent.

Antibiotic-resistant enterococci e.g., *E. faecium* are particularly significant cause of bloodstream infection in hospitalized patients, endocarditis, catheter-associated bacteremia, meningitis, and intra-abdominal infection. Those susceptible to infection include patients with neutropenia and/or cancer, patients receiving long-term hemodialysis, and liver transplant recipients. There is a clear need for anti-enterococcal compounds especially oral, bactericidal compounds.

*Pseudomonas aeruginosa* is an invasive, gram-negative bacterial pathogen that causes a wide range of severe infections which may cause morbidity in immunocompromised subjects e.g., caused by HIV infection, chemotherapy, or immunosuppressive therapy. Furthermore, *P. aeruginosa* causes serious infections of the lower respiratory tract, the urinary tract, and wounds in younger and older hospitalized ill patients, including those suffering from cystic fibrosis. As with Acinetobacter species and ESBL-producing Enterobacteriaceae, the incidence of *P. aeruginosa* infection among intensive care unit patients is increasing. Moreover, *P. aeruginosa* has a greater ability than most gram-positive and many gram-negative pathogens to develop resistance.

Accordingly there is a clear need in the art for new antimicrobial compounds.

In an effort to identify new antimicrobial compounds with a mechanism of action different to those of conventional antibiotics, both pharmaceutical and biotechnology companies have turned their attention to naturally-occurring antimicrobial peptides. In this respect, antimicrobial peptides are generally defined as a peptide with direct antibiotic activity, having fewer than about 50 amino acids and having a net positive charge. Generally, antimicrobial peptides may be grouped into the following four distinct families based on biochemical characteristics:

(i) Linear cationic basic peptides forming amphipathic α-helices, such as the cecropins or the magainins;
(ii) Peptides with one to six intramolecular disulfide linkages, such as the defensins;
(iii) Proline-rich peptides, such as apidaecins and abaecins; and
(iii) Glycine-rich antimicrobial peptides or polypeptides, such as the attacins.

Generally, an antimicrobial peptide binds to the negatively charged microbial membrane as a consequence of its overall positive charge. The peptide then inserts into the membrane and creates a conductance pathway that permits the leakage of protons, other ions and some larger cellular constituents (Zhang et al., *J. Biol. Chem.*, 276: 35714-35722, 2001). Antimicrobial peptides may also bind to intracellular targets and inhibit cellular processes, such as, for example, RNA or protein synthesis or ATPase activity, thereby resulting in cell death.

The majority of antimicrobials tested to date, including antimicrobial peptides, are ineffective for therapeutic treatment. For example, the Bovine Myeloid Antimicrobial Peptides (BMAPs) are toxic to cultured blood cells and blood cell-derived cell lines (Risso et al., *Cell Immunol.*, 189: 107-115, 1998). Accordingly, these peptides are ineffective for intravenous administration to a subject.

Other peptides that have been found to be toxic to cells and/or subjects, include, for example, peptides derived from bee venom, wasp venom or scorpion toxin. For example, the bee venom peptide, melittin forms channel-like structures in biological membranes generally and causes hemolysis, cytolysis, membrane depolarization, activation of tissue phospholipase C and involuntary muscle contraction.

The antimicrobial activities of several antimicrobial peptides, including several β-defensins, are inhibited at physiological salt concentrations (Huang et al., *Eye Contact Lens*, 31: 34-38, 2005). Accordingly, these peptides are ineffective for treatment of conditions that require the peptide to be exposed to a body fluid, such as, for example, blood or saliva.

Given the complexity of microorganisms of potential or real pathogenicity to animals and humans, there is a clear need for a diverse range of effective antimicrobials e.g., having a broad spectrum or a spectrum of activity that complements existing therapeutics e.g., known antibiotics or antimicrobial proteins. There also remains a need for antimicrobial proteins having specific activity comparable to that of existing antibiotic treatments, preferably without the development of the resistance that occurs to conventional antibiotic compounds. There is also a need for antimicrobials that are effective in a wide range of applications, including the food, agriculture and horticulture industries, and in medicine, veterinary science and phytopathology. Clearly, it is highly desirable for any antimicrobial composition of matter to exhibit reduced toxicity and high activity at physiological conditions, e.g., at physiological salt concentrations. Desirably, compounds are for administration to animals or humans will not be highly antigenic in so far as their ability to stimulate specific B-cell or T-cell production is concerned, however will possess adjuvant activity.

SUMMARY OF THE INVENTION

General

This specification contains nucleotide and amino acid sequence information prepared using PatentIn Version 3.3. Each nucleotide sequence is identified in the sequence listing by the numeric indicator <210> followed by the sequence identifier (e.g. <210>1, <210>2, <210>3, etc). The length and type of sequence (DNA, protein (PRT), etc), and source organism for each nucleotide sequence, are indicated by information provided in the numeric indicator fields <211>, <212> and <213>, respectively. Nucleotide sequences referred to in the specification are defined by the term "SEQ ID NO:", followed by the sequence identifier (eg. SEQ ID NO: 1 refers to the sequence in the sequence listing designated as <400>1).

The designation of nucleotide residues referred to herein are those recommended by the IUPAC-IUB Biochemical Nomenclature Commission, wherein A represents Adenine, C represents Cytosine, G represents Guanine, T represents thymine, Y represents a pyrimidine residue, R represents a purine residue, M represents Adenine or Cytosine, K represents Guanine or Thymine, S represents Guanine or Cytosine, W represents Adenine or Thymine, H represents a nucleotide other than Guanine, B represents a nucleotide other than Adenine, V represents a nucleotide other than Thymine, D represents a nucleotide other than Cytosine and N represents any nucleotide residue.

As used herein the term "derived from" shall be taken to indicate that a specified integer may be obtained from a particular source albeit not necessarily directly from that source.

Throughout this specification, unless the context requires otherwise, the word "comprise", or variations such as "comprises" or "comprising", will be understood to imply the inclusion of a stated step or element or integer or group of steps or elements or integers but not the exclusion of any other step or element or integer or group of elements or integers.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Each embodiment described herein is to be applied mutatis mutandis to each and every other embodiment unless specifically stated otherwise.

Each embodiment directed to an amino acid sequence selected from the group consisting of SEQ ID Nos: 1-17 shall be taken to apply mutatis mutandis to an amino acid sequence selected from the group consisting of SEQ ID Nos: 18-29 and/or an amino acid sequence selected from the group consisting of SEQ ID Nos: 30-40. Each embodiment directed to an amino acid sequence selected from the group consisting of SEQ ID Nos: 18-29 shall be taken to apply mutatis mutandis to an amino acid sequence selected from the group consisting of SEQ ID Nos: 1-17 and/or an amino acid sequence selected from the group consisting of SEQ ID Nos: 30-40. Each embodiment directed to an amino acid sequence selected from the group consisting of SEQ ID Nos: 30-40 shall be taken to apply mutatis mutandis to an amino acid sequence selected from the group consisting of SEQ ID Nos: 1-17 and/or an amino acid sequence selected from the group consisting of SEQ ID Nos: 18-29.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The present invention is not to be limited in scope by the specific embodiments described herein, which are intended for the purpose of exemplification only. Functionally-equivalent products, compositions and methods are clearly within the scope of the invention, as described herein.

SPECIFIC EMBODIMENTS

In work leading up to the present invention, the present inventors sought to identify new antimicrobial compounds. The inventors synthesized peptides derived from milk proteins of the tammar wallaby *Macropus eugenii* and tested the derived peptides, and derivatives and analogs thereof for their ability to inhibit growth of a variety of gram-negative bacteria, gram-positive bacteria and fungi. Several peptides, derivatives and analogs were identified that retained considerable antimicrobial activity at a physiological salt concentration.

The inventors also characterized the toxicity of peptides to mammalian cells, using a hemolysis assay. The peptides tested did not cause substantial levels of hemolysis at concentrations at which the peptides exert antimicrobial activity. Accordingly, the peptides identified by the inventors represent attractive therapeutic molecules as they retain antimicrobial activity under physiological conditions and have a low level of toxicity to mammalian cells.

Accordingly, the present invention provides an antimicrobial peptide fragment of a tammar wallaby milk protein or an antimicrobial derivative or analog thereof, wherein it is preferred for said peptide, derivative or analog to have enhanced activity (i.e., about 8-16 fold lower MIC) against one or a plurality of gram-negative bacteria e.g., *Escherichia coli* DH5 α and/or *Pseudomonas aeruginosa* and/or *Acinetobacter baumannii* and/or *Klebsiella pneumoniae*, relative to an equivalent amount, e.g., an equimolar concentration, of LL-37 peptide comprising amino acid residues 104-140 of the 18-kDa human cationic antimicrobial protein (hCAP18) described e.g., by Larrick et al., *Infect. Immun.* 63, 1291-1297 (1995); Cowland et al., *FEBS Lett.* 368, 173-176 (1995) and Lehrer and Ganz, *Curr. Opin. Immunol.* 11, 23-27 (1999). Accordingly, the antimicrobial peptide of the present invention has a lower minimum inhibitory concentration (MIC) against one or more of such gram negative bacteria than LL-37.

As used herein, the term "antimicrobial" shall be taken to mean that the peptide is capable of killing a microorganism and/or preventing growth of a microorganism, i.e., the peptide has microbicidal activity and/or microbistatic activity. Methods for determining the antimicrobial activity of a peptide will be apparent to the skilled artisan and/or described herein. For example, the peptide is applied to a substrate upon which a microorganism has been previously grown and, after a suitable period of time, the level of growth inhibition and/or cell death of the microorganism is determined. The term "microorganism" includes any microscopic organism and, preferably, a pathogenic microscopic organism. Accordingly, the term "microorganism" includes a bacterium, an archaebacterium, a virus, a yeast, a fungus or a protist. Preferably, the microorganism is a bacterium or a fungus.

In a preferred embodiment, the antimicrobial peptide or analog or derivative thereof is capable of inhibiting the growth of or killing a bacterium and/or a fungus. Preferably, the antimicrobial peptide or analog or derivative thereof is capable of inhibiting the growth of or killing a bacterium. Alternatively, antimicrobial peptide or analog or derivative thereof is capable of inhibiting the growth of or killing a fungus.

Alternatively, or in addition, the antimicrobial peptide fragment of a tammar wallaby milk protein or a derivative or analog thereof has antimicrobial activity against one or more multidrug-resistant bacteria. In the present context, the term "multidrug-resistant" shall be taken to mean that a bacterium is resistant to at least two antibiotics belonging to two or more major class of antibiotic compounds e.g., fluoroquinolones, aminoglycosides, beta-lactams, carbapenems, monobactams, glyeopeptides, clindamycin, and macrolides. For example, a multidrug-resistant bacterium can be a multidrug-resistant gram negative bacterium e.g., a multidrug-resistant bacterium belonging to a genus selected from the group consisting of *Escherichia, Pseudomonas, Proteus, Salmonella, Acinetobacter* and *Klebsiella*. Alternatively, or in addition, a multidrug-resistant bacterium can be a multidrug-resistant gram positive bacterium e.g., a multidrug-resistant bacterium belonging to a genus selected from the group consisting of *Bacillus, Staphylococcus, Enterococcus* and *Streptococcus*, and preferably a multidrug-resistant bacterium belonging to a genus selected from the group consisting of *Bacillus, Enterococcus* and *Streptococcus*. Additional gram-negative and/or gram-positive bacteria are not to be excluded.

Alternatively, or in addition, the antimicrobial peptide fragment of a tammar wallaby milk protein or a derivative or analog thereof has antimicrobial activity against one or more fungi e.g., of the genus *Candida*. Additional fungi are not to be excluded Disclosed herein are antimicrobial peptides derived from tammar wallaby milk proteins which comprise the sequences set forth SEQ ID Nos: 1-40. As shown in the accompanying examples, a peptide comprising an amino acid sequence selected from the group consisting of SEQ ID NO: 2, SEQ ID NO: 19 and SEQ ID NO: 31 or a derivative or analog of SEQ ID NO: 2 comprising a sequence selected from SEQ ID Nos: 9, 11, 13, 17 exhibits superior antimicrobial activity especially albeit not exclusively against gram negative bacteria.

Accordingly, the antimicrobial peptide of the present invention can comprise an amino acid sequence comprising at least six contiguous amino acids of amino acid sequence selected from the group consisting of SEQ ID NO: 1, SEQ ID NO: 18 and SEQ ID NO: 30 or a derivative or analog of said antimicrobial peptide. Alternatively, the antimicrobial peptide of the invention comprises an amino acid sequence comprising at least six contiguous amino acids set forth in SEQ ID NO: 1 or SEQ ID NO: 2, or a derivative or analog of said antimicrobial peptide. Alternatively, the antimicrobial peptide of the invention comprises an amino acid sequence comprising at least six contiguous amino acids set forth in SEQ ID NO: 18 or SEQ ID NO: 19 or a derivative or analog of said antimicrobial peptide. Alternatively, the antimicrobial peptide of the invention comprises an amino acid sequence comprising at least six contiguous amino acids set froth in SEQ ID NO: 30 or SEQ ID NO: 31 or a derivative or analog of said antimicrobial peptide.

As used herein the term "derivative" shall be taken to mean a peptide that is derived from an antimicrobial peptide of the invention, e.g., a fragment or processed form of an antimicrobial peptide of the invention. The term "derivative" also encompasses a peptide comprising an reversed sequence relative to the native or endogenous sequence of an antimicrobial peptide disclosed herein. The term "derivative" also encompasses fusion proteins encompasses prising an antimicrobial peptide of the invention. For example, the fusion protein comprises a label, such as, for example, an epitope or tag sequence to facilitate isolation or identification of an antimicrobial peptide to which it is covalently linked, e.g., influenza virus Hemagglutinin (HA) epitope (SEQ ID NO: 41), simian virus 5 (SV-5) epitope (SEQ ID NO: 42), hexa-histidine sequence (SEQ ID NO: 43), c-myc tag (SEQ ID NO: 44) or FLAG tag (SEQ ID NO: 45).

The term "derivative" also encompasses a derivatized peptide, such as, for example, a peptide modified to contain one or more-chemical moieties other than an amino acid. The chemical moiety may be linked covalently to the peptide e.g., via an amino terminal amino acid residue, a carboxy terminal amino acid residue, or at an internal amino acid residue. Such modifications include the addition of a protective or capping group on a reactive moiety in the peptide, addition of a detectable label, and other changes that do not adversely destroy the activity of the peptide compound.

Additional suitable fusion proteins will be apparent to the skilled artisan based on the disclosure herein and include, for example, a fusion protein comprising a plurality of the antibacterial peptides described herein in any embodiment.

Exemplary fragments of an antimicrobial peptide of the present invention will comprise a sequence selected from the group consisting of SEQ ID Nos: 2-7, 19, and 31-35. Exemplary reversed sequences of an antimicrobial peptide of the present invention will comprise a sequence selected from the group consisting of SEQ ID Nos: 12-17, 24-29 and 38-40. Exemplary fusion proteins will comprise any one or more of SEQ ID Nos: 1-40 fused to one or more of SEQ ID Nos: 41-45, or a plurality of antimicrobial peptides selected from the group consisting of SEQ ID Nos: 1-40 covalently linked and optionally separated by one or more spacer residues.

As used herein, the term "analog" shall be taken to mean a peptide that is modified to comprise one or more naturally-occurring and/or non-naturally-occurring amino acids, provided that the peptide analog displays antimicrobial activity. For example, the term "analog" encompasses an antimicrobial peptide as described herein in any embodiment comprising one or more conservative amino acid changes. The term "analog" also encompasses a peptide comprising, for example, one or more D-amino acids. Such an analog has the characteristic of, for example, reduced immunogenicity and/or protease resistance. For example, analogs may be beneficial for contexts in which proteolysis may degrade unmodified proteins e.g., for treatment of infections involving microbes that produce high concentrations of proteases e.g., as a resistance mechanism, or for administration to serum. Exemplary analogs of an antimicrobial peptide of the present invention will comprise a sequence selected from the group consisting of SEQ ID Nos: 8-11, 14-19, 22, 23, 26-29, 36, 37, 39 and 40 (of which SEQ ID Nos: 12-17, 24-29 and 38-40 are also inverted relative to the tammar wallaby sequences from which they were derived).

Preferred analogs and derivatives other than those specifically exemplified herein will comprise an amino acid sequence at least about 60% identical to an amino acid sequence selected from the group consisting of SEQ ID NO: 1, SEQ ID NO: 18 and SEQ ID NO: 30 or a derivative or analog thereof. Analogs and derivatives other than those specifically disclosed herein are readily produced without undue experimentation based on the teaching provided herein and/or based on the known structure/function relationships of various classes of analogs and derivatives e.g., retroinverted peptides.

Preferably, the antimicrobial peptide or analog or derivative thereof has antimicrobial activity in the presence of a physiological salt concentration. As used herein, the term "physiological salt concentration" shall be taken to mean a physiological salt concentration in a mammal. Preferably, the term "physiological salt concentration" shall be taken to mean the salt concentration in blood and/or serum of a mammal. For example, a physiological salt concentration is between about 80 mM NaCl and about 200 mM NaCl. Preferably, a physiological salt concentration is between about 90 mM NaCl and about 150 mM NaCl. More preferably, a physiological salt concentration is between about 100 mM NaCl and about 150 mM NaCl. Even more preferably, a physiological salt concentration is about 100 mM NaCl.

It is also preferable that the antimicrobial peptide or analog or derivative thereof of the invention has a low level of toxicity to mammalian cells at a concentration at which it is capable of preventing microbial growth and/or killing a microorganism. As used herein, the term "low level of toxicity" shall be taken to mean that the peptide induces cell death in less than about 20% of cells to which it is exposed. Preferably, the peptide induces cell death in less than about 15% of cells to which it is exposed. More preferably, the peptide induces cell death in less than about 10% of cells to which it is exposed. Even more preferably, the peptide induces cell death in less than about 5% of cells to which it is exposed. Preferably, the mammalian cell used to test the toxicity is a blood cell, such as, for example, a red blood cell. Accordingly, it is preferable that the antimicrobial peptide or analog or derivative thereof induces a low level of haemolysis at a concentration at which it is capable of preventing microbial growth and/or killing a microorganism Alternatively, or in addition, the present invention provides a complex of antimicrobial peptides and/or analogs and/or derivatives of the present invention. Without being bound by theory or mode of action or suggesting that a complex is necessary for performance of the present invention, such a complex is useful for enhancing the antimicrobial activity of an antimicrobial peptide or analog or derivative of the invention. For example, the present invention provides a complex of the same antimicrobial peptide, analog or derivative. Alternatively, the present invention provides a complex or aggregate comprising a plurality of different antimicrobial peptides and/or analogs and/or derivatives of the invention. Such complex or aggregate may comprise additional antimicrobial peptides known in the art.

The present invention also provides a composition comprising an effective amount of an antimicrobial peptide, analog derivative, fusion protein or complex as described herein in any embodiment. For example, the present invention provides a disinfecting solution (e.g., for cleaning a surface), a preservative (e.g., for preventing microbial growth on or in a food product), a pharmaceutical composition or a phytoprotective composition. Such a composition may take any of a number of forms, such as, for example, a solution (e.g., a spray solution or a pharmaceutical solution, e.g., a nasal spray solution or syrup), an aerosol, a cream, a lotion, a gel or a powder. Suitable compositions will be apparent to the skilled artisan based on the description herein.

An antimicrobial peptide of the present invention also stimulates the immune response of a subject to a pathogen or an antigen, e.g., by stimulating the innate immune response of said subject. As used herein, the term "innate immune response" shall be taken to mean an inherited, non-specific immune response, as opposed to an adaptive immune response. Generally, an innate immune response involves the detection of a pathogen associated molecular pattern on the surface of a microorganism (e.g., lipopolysaccharide) by a receptor in a subject, e.g., a TOLL-receptor or a NOD protein, resulting in increased production of macrophages, dendritic cells and/or neutrophils and/or activation of the complement system and/or expression of an antibacterial peptide, thereby killing said microorganism. Preferred compositions of matter that stimulate innate immune responses are not themselves highly antigenic as determined by their ability to stimulate the production of antibodies or cytotoxic T-cells that bind to and/or process and/or present them on their surface(s).

For example, the antimicrobial peptides of the invention and analogs and derivatives thereof can stimulate IL-8 production by THP-1 cells stimulated previously using *E. coli* LPS, as determined by standard ELISA. The antimicrobial peptides also exhibit anti-endotoxic properties, as determined by their ability to neutralize the LPS-induced production of the pro-inflammatory cytokine IL-8 in the differentiated macrophage-like THP-1 cell line at low concentration (less than about 0.5 µg/ml).

Accordingly, the present invention additionally provides a composition that induces, enhances or stimulates an immune response by a subject. Accordingly, the present invention provides a composition having an adjuvant property, i.e., an adjuvant, said composition or adjuvant comprising an antimicrobial peptide of the invention or an analog or derivative thereof.

As used herein, the term "adjuvant" shall be taken to mean a compound or composition that non-specifically enhances or induces an immune response of a subject to which it is administered. In the context of the present invention an adjuvant composition generally does not induce a specific immune response, e.g., a B-cell response or a cytotoxic T-cell response against an antimicrobial peptide of the invention or an analog or derivative thereof.

Preferably, the composition stimulates an innate immune response in a subject to which it is administered. In this respect, plants, animals and insects are capable of mounting an innate immune response. Accordingly the composition of the present embodiment preferably induces an immune response, preferably an innate immune response, in an animal and/or a plant and/or an inset. More preferably, the composition of the present embodiment preferably induces an immune response, preferably an innate immune response, in a human.

An adjuvant composition of the present invention may also comprise, for example, a microorganism and/or a cancer cell and/or an antigen, e.g., from a microorganism or cancer cells. Such a composition is useful for, for example, stimulating an immune response against said microorganism or cancer cell.

The present invention also provides a solid surface coated with or having adsorbed thereto an antimicrobial peptide, analog derivative, fusion protein, complex or aggregate as described herein in any embodiment. For example, the present invention provides a bead or implant coated with an antimicrobial peptide of the invention, e.g., for insertion into a subject to treat a disease or disorder. Alternatively, the present invention provides a prosthetic device coated with or having adsorbed thereto an antimicrobial peptide of the invention or an analog or derivative thereof to thereby reduce or prevent infection following insertion of the device.

In another embodiment, the present invention provides a method for providing or producing an isolated or recombinant antimicrobial peptide or analog or derivative of the invention. For example, the method comprises providing or obtaining information concerning the antimicrobial peptide, analog and/or derivative (e.g., the sequence of the peptide or nucleic acid encoding same) and synthesizing or expressing the peptide, analog or derivative. Methods for synthesizing and/or expressing an antimicrobial peptide, analog or derivative of the invention will be apparent to the skilled artisan based on the description herein.

The antimicrobial activity of the peptides, analogs and/or derivatives of the invention makes them suitable for reducing or preventing microbial growth. Accordingly, the present invention also provides a method for reducing or preventing microbial growth, said method comprising contacting a microorganism or a surface or composition of matter suspected of comprising a microorganism with a peptide, analog or derivative of the invention for a time and under conditions sufficient to reduce microbial growth and/or kill a microorganism, thereby reducing or preventing microbial growth. Such a method is suitable for, for example, disinfecting a surface and/or preserving a food product and/or reducing or preventing water contamination.

Alternatively, or in addition, the method comprises applying the surface or composition of matter suspected of comprising a microorganism with a peptide, analog or derivative of the invention for a time and under conditions sufficient to reduce microbial growth and/or kill a microorganism, thereby reducing or preventing microbial growth. For example, the peptide, analog or derivative of the invention is sprayed onto the surface or composition of matter. Such spray application is useful for, for example, applying a peptide, analog or derivative of the invention to a food product or a fluid to be consumed, e.g., by a human. This is because spraying the peptide, analog or derivative reduces the handling of said food product or fluid, thereby further reducing the risk of microorganism contamination.

In one embodiment, the method additionally comprises performing a method to detect the presence of a microorganism. Such a detection method may be performed prior to and/or following contacting with a peptide, analog and/or derivative of the invention.

As will be apparent to the skilled artisan based on the foregoing, the present invention also provides for the use of a peptide, analog and/or derivative of the invention in the manufacture of a composition for reducing or preventing microbial growth.

As a peptide of the present invention is useful for reducing microbial growth in a food product, the present invention additionally provides a method for prolonging the storage life of a perishable product, said method comprising:

(i) contacting a perishable product with an antimicrobial peptide of the present invention for a time and under conditions sufficient to reduce or prevent growth of a microorganism and/or to kill a microorganism; and (ii) storing the perishable product.

In this respect, the perishable product is capable of being stored for a longer period of time than the same product that has not been contacted with an antimicrobial peptide of the invention.

The skilled artisan will be aware that such a method is useful for prolonging the storage life of, for example, a food product, e.g., meat, fruit, vegetable, dairy; a pharmaceutical composition; and/or a washing solution, e.g., saline for contact lenses.

The present invention also provides a method of therapeutic or prophylactic treatment of a subject comprising administering an antimicrobial peptide, analog and/or derivative of the invention or composition comprising same to a subject in need thereof. In this respect, a subject in need of treatment with a peptide, analog or derivative of the invention is, for example, a subject suffering from an infection or suspected of suffering from an infection or at risk of developing an infection As used herein, the term "subject" shall be taken to mean any animal, including a human, plant or insect that may be infected by a microorganism. Preferably, the subject is any animal, including a human, plant or insect that may be infected by a microorganism against which an antimicrobial peptide of the invention.

Preferably, the peptide is administered under conditions sufficient for the peptide, analog and/or derivative to reduce or prevent microbial growth and/or to kill a microorganism, e.g., in a pharmaceutical composition.

As used herein, the term "infection" shall be taken to mean the invasion, development and/or multiplication of a microorganism within or on another organism. An infection may be localized to a specific region of an organism or systemic. Infections for which a peptide, analog and/or derivative of the invention are useful for treating include any infection caused by a bacteria or a fungus and will be apparent to the skilled artisan from the disclosure herein.

In this respect, the present invention is not limited to the treatment of an infection in an animal subject. Rather, a peptide, analog and/or derivative of the present invention is also useful for, for example, treatment of a plant to thereby reduce or prevent a microbial infection therein or thereon. Accordingly, the antimicrobial peptide of the invention or analog or derivative thereof is a phytoprotective agent.

In a preferred embodiment, the subject is an animal, and more preferably a mammal. Accordingly, the antimicrobial peptide of the invention or analog or derivative thereof is a pharmaceutical agent.

The antimicrobial peptide, analog and/or derivative of the invention may be administered to a subject by any of a variety of means, such as, for example, topical administration, nasal administration, oral administration, vaginal administration, rectal administration, intravenous administration, intraperitoneal administration, or subcutaneous administration. For example, as infectious microorganisms generally enter a mammal by way of a membrane, e.g., a mucus membrane, a peptide, analog or derivative of the invention is preferably administered in a manner suitable to contact a membrane. For example, the peptide, analog and/or derivative is administered by topical administration, nasal administration, oral administration, vaginal administration, rectal administration.

In the case of a systemic infection or a localised infection of a tissue or part thereof that is within a subject a peptide may be administered by, for example, intravenous administration, intraperitoneal administration, or subcutaneous administration. In such a case, it is preferable to administer a peptide, analog and/or derivative with reduced immunogenicity to avoid or reduce the risk of the subject raising an immune response against the peptide, analog and/or derivative. Preferably, the peptide, analog and/or derivative is resistant to protease degradation to thereby increase its half-life in the subject and, as a consequence, it therapeutic/prophylactic benefit.

An antimicrobial peptide of the invention or a derivative thereof may also be administered to a subject by expressing the peptide or derivative in the subject. For example, the peptide or derivative is expressed in a transgenic subject (e.g., a transgenic plant) or is expressed by a cell administered to a subject, e.g., ex vivo therapeutic or prophylactic treatment. Methods for expressing a peptide of the invention in a cell or subject will be apparent to the skilled artisan and/or described herein.

In a preferred embodiment, a method of treating a subject of the invention additionally comprises providing or obtaining an antimicrobial peptide, analog and/or derivative of the invention or information concerning same. For example, the present invention provides a method of therapeutic or prophylactic treatment of a subject, said method comprising:
(i) determining a subject suffering from an infection or at risk of developing an infection;
(ii) obtaining an antimicrobial peptide, analog and/or derivative of the invention; and
(iii) administering said peptide, analog or derivative to said subject.

In another embodiment, the present invention provides a method for the prophylactic or therapeutic treatment of an infection, said method comprising:
(i) identifying a subject suffering from an infection or suspected of suffering from an infection or at risk of developing an infection; and
(ii) recommending administration of an antimicrobial peptide of the invention or an analog or derivative thereof.

As will be apparent to the skilled artisan based on the foregoing, the present invention also provides for the use of a peptide, analog and/or derivative of the invention in medicine. For example, the present invention provides for the use of an antimicrobial peptide, analog or derivative in the manufacture of a medicament for the treatment or prophylaxis of an infection.

As discussed hereinabove, the antimicrobial peptides or analogs or derivatives thereof of the present invention also enhance an immune response of a subject e.g., to a pathogen or antigen. Alternatively, the antimicrobial peptides or analogs or derivatives thereof of the present invention have adjuvant activity. Accordingly, the present invention additionally provides a method for enhancing an innate immune response of a subject comprising administering an antimicrobial peptide of the invention or an analog or derivative thereof for a time and under conditions sufficient to stimulate the immune system of a subject.

Alternatively, the present invention provides a method for enhancing an immune response of a subject against a pathogen or an antigen, said method comprising administering an antimicrobial peptide of the invention or an analog or derivative thereof for a time and under conditions sufficient to stimulate the innate immune system of a subject, thereby enhancing an immune response of a subject against the pathogen or antigen.

For example, the present invention stimulates the production of a cell-type associated with innate immunity, such as, for example, a macrophage or a dendritic cell or the expression of one or more complement components and/or the expression of an antibacterial peptide.

As the innate immune system is generally activated in response to an infection and/or a cancer, the present invention additionally provides a method of therapeutic or prophylactic treatment of a subject suffering from or at risk of developing an infection or a cancer, said method comprising administering an antimicrobial peptide of the invention or an analog or derivative thereof for a time and under conditions sufficient to induce or enhance the innate immune response of the subject, thereby stimulating the immune response to an organism that causes the infection or a cancer cell.

The present invention also provides for the use of the antimicrobial peptide of the invention or an analog or derivative thereof in the manufacture of a compound for enhancing the immune response of a subject. Alternatively, the invention also provides for the use of the antimicrobial peptide of the invention or an analog or derivative thereof in the manufacture of a compound for inducing an immune response against a pathogen or an antigen.

DETAILED DESCRIPTION OF THE PREFERRED EMBODIMENTS

Suitable Peptides, Derivatives and Analogs

Figure 1A:
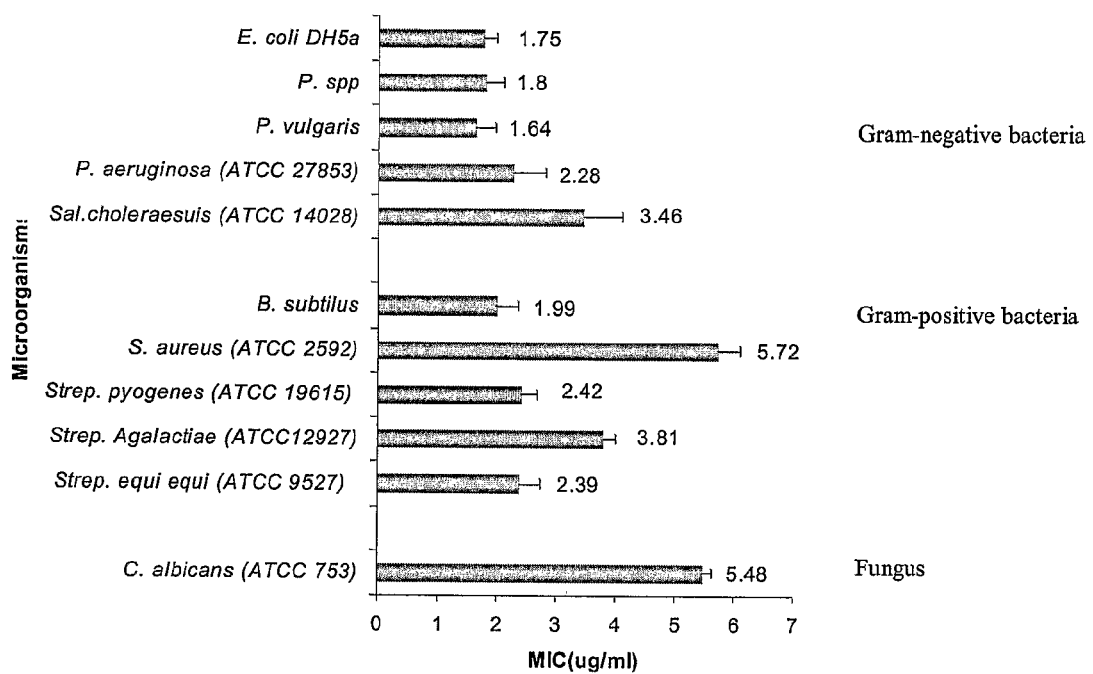
FIG. 1a is a graphical representation of the minimum inhibitory concentration (MIC) of an antimicrobial peptide comprising an amino acid sequence set forth in SEQ ID NO: 2 as determined using a radial diffusion assay. The MIC (μg/ml) is indicated on the X-axis. The MIC is defined as the χ intercept of the least mean square regression lines through the respective data points. Results are means±standard error of the mean (SEM) from two experiments. The microorganism being tested is indicated on the Y axis.

In a preferred embodiment, the present invention provides an antimicrobial peptide comprising at least seven or eight or ten or fifteen or twenty amino acids of an amino acid selected from the group consisting of SEQ ID NO: 1, SEQ ID NO: 18 and SEQ ID NO: 30. Preferably, the peptide comprises at least about ten amino acids of an amino acid selected from the group consisting of SEQ ID NO: 1, SEQ ID NO: 18 and SEQ ID NO: 30. More preferably, the peptide comprises at least fifteen amino acids of an amino acid selected from the group consisting of SEQ ID NO: 1, SEQ ID NO: 18 and SEQ ID NO: 30. Still more preferably, the peptide comprises at least twenty amino acids of an amino acid selected from the group consisting of SEQ ID NO: 1, SEQ ID NO: 18 and SEQ ID NO: 30.

Preferably, the antimicrobial peptide, analog and/or derivative comprises an amino acid sequence at least about 65% identical to an amino acid selected from the group consisting of SEQ ID NO: 1, SEQ ID NO: 18 and SEQ ID NO: 30. Preferably, the degree of sequence identity is at least about 70%. More preferably, the degree of sequence identity is at least about 75%. Even more preferably, the degree of sequence identity is at least about 80%. Still more preferably, the degree of sequence identity is at least about 85%. Even more preferably, the degree of sequence identity is at least about 90%. Still more preferably, the degree of sequence identity is at least about 95%. Still more preferably, the degree of sequence identity is at least about 99%, for example, 100%.

In determining whether or not two amino acid sequences fall within the defined percentage identity limits supra, those skilled in the art will be aware that it is possible to conduct a side-by-side comparison of the amino acid sequences. In such comparisons or alignments, differences will arise in the positioning of non-identical residues depending upon the algorithm used to perform the alignment. In the present context, references to percentage identities and similarities between two or more amino acid sequences shall be taken to refer to the number of identical and similar residues respectively, between said sequences as determined using any standard algorithm known to those skilled in the art. In particular, amino acid identities and similarities are calculated using software of the Computer Genetics Group, Inc., University Research Park, Madison, Wis., United States of America, e.g., using the GAP program of Devereaux et al., *Nucl. Acids Res.* 12, 387-395, 1984, which utilizes the algorithm of Needleman and Wunsch, *J. Mol. Biol.* 48, 443-453, 1970. Alternatively, the CLUSTAL W algorithm of Thompson et al., *Nucl. Acids Res.* 22, 4673-4680, 1994, is used to obtain an alignment of multiple sequences, wherein it is necessary or desirable to maximize the number of identical/similar residues and to minimize the number and/or length of sequence gaps in the alignment.

Alternatively, a suite of commonly used and freely available sequence comparison algorithms is provided by the National Center for Biotechnology Information (NCBI) Basic Local Alignment Search Tool (BLAST) (Altschul et al. *J. Mol. Biol.* 215: 403-410, 1990), which is available from several sources, including the NCBI, Bethesda, Md. The BLAST software suite includes various sequence analysis programs including "blastn," that is used to align a known nucleotide sequence with other polynucleotide sequences from a variety of databases and "blastp" used to align a known amino acid sequence with one or more sequences from one or more databases. Also available is a tool called "BLAST 2 Sequences" that is used for direct pairwise comparison of two nucleotide sequences.

As used herein the term "NCBI" shall be taken to mean the database of the National Center for Biotechnology Information at the National Library of Medicine at the National Institutes of Health of the Government of the United States of America, Bethesda, Md., 20894.

In this respect, non-natural amino acids shall be considered to be identical to their natural counterparts. Accordingly, a peptide comprising only non-natural amino acids (e.g., D-amino acids) equivalent to those set forth in SEQ ID NO: 1 shall be considered to have an amino acid sequence 100% identical to SEQ ID NO: 1.

Preferably, an antimicrobial peptide or analog or derivative thereof is between about 6 to about 100 residues long (or any value there between), preferably from about 15 to 75 residues (or any value there between), preferably from about 20 to about 50 residues (or any value there between), and even more preferably from about 24 to about 40 residues (or any value there between).

Peptide Analogs

Suitable peptide analogs include, for example, an antimicrobial peptide comprising one or more conservative amino acid substitutions. A "conservative amino acid substitution" is one in which the amino acid residue is replaced with an amino acid residue having a similar side chain.

Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), .beta.-branched side chains (e.g., threonine, valine, isoleucine) and aromatic side chains (e.g., tyrosine, phenylalanine, tryptophan, histidine).

Analogs of the modulator compounds of the invention are intended to include compounds in which one or more amino acids of the peptide structure are substituted with a homologous amino acid such that the properties of the original modulator are maintained. Preferably conservative amino acid substitutions are made at one or more amino acid residues.

The importance of the hydropathic amino acid index in conferring interactive biological function on a protein is generally understood in the art (Kyte & Doolittle, J. Mol. Biol. 157, 105-132, 1982). It is known that certain amino acids may be substituted for other amino acids having a similar hydropathic index or score and still retain a similar biological activity, for example, the ability to bind to a membrane of a microorganism and/or kill the microorganism. The hydropathic index of amino acids also may be considered in determining a conservative substitution that produces a functionally equivalent molecule. Each amino acid has been assigned a hydropathic index on the basis of their hydrophobicity and charge characteristics, as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making changes based upon the hydropathic index, the substitution of amino acids whose hydropathic indices are within +/−0.2 is preferred. More preferably, the substitution will involve amino acids having hydropathic indices within +/−0.1, and more preferably within about +/−0.05.

It is also understood in the art that the substitution of like amino acids is made effectively on the basis of hydrophilicity. As detailed in U.S. Pat. No. 4,554,101, the following hydrophilicity values have been assigned to amino acid residues: arginine (+3.0); lysine (+3.0); aspartate (+3.0+/−0.1); glutamate (+3.0+/−0.1); serine (+0.3); asparagine (+0.2); glutamine (+0.2); glycine (0); threonine (−0.4); proline (−0.5+/−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, it is preferred to substitute amino acids having hydrophilicity values within about +/−0.2 of each other, more preferably within about +/−0.1, and even more preferably within about +/−0.05

The present invention also contemplates non-conservative amino acid changes. For example, of particular interest are substitutions of charged amino acids with another charged amino acid and with neutral or positively charged amino acids. The latter of these substitutions results in an antimicrobial peptide analog having reduced positive charge, thereby improving the characteristics of the antimicrobial peptide.

Additional preferred peptide analogs have reduced immunogenicity compared to an antimicrobial peptide of the invention. Alternatively, or in addition, a preferred peptide analog has enhanced stability compared to an antimicrobial peptide of the invention.

It also is contemplated that other sterically similar compounds may be formulated to mimic the key portions of the peptide structure. Such compounds, which may be termed peptidomimetics, may be used in the same manner as the peptides of the invention and hence are also analogs of a peptide of the invention. The generation of such an analog may be achieved by the techniques of modeling and chemical design known to those of skill in the art. It will be understood that all such sterically similar antimicrobial peptide analogs fall within the scope of the present invention.

Another method for determining the "equivalence" of modified peptides involves a functional approach. For example, a given peptide analog is tested for its antimicrobial activity e.g., using any screening method described herein.

Particularly preferred analogs of a peptide of the invention will comprise one or more non-naturally occurring amino acids or amino acid analogs. For example, an antimicrobial peptide of the invention may comprise one or more naturally occurring non-genetically encoded L-amino acids, synthetic L-amino acids or D-enantiomers of an amino acid. For example, the peptide comprises only D-amino acids. More particularly, the analog may comprise one or more residues selected from the group consisting of: hydroxyproline, β-alanine, 2,3-diaminopropionic acid, α-aminoisobutyric acid, N-methylglycine (sarcosine), ornithine, citrulline, t-butylalanine, t-butylglycine, N-methylisoleucine, phenylglycine, cyclohexylalanine, norleucine, naphthylalanine, pyridylalanine 3-benzothienyl alanine 4-chlorophenylalanine, 2-fluorophenylalanine, 3-fluorophenylalanine, 4-fluorophenylalanine, penicillamine, 1,2,3,4-tetrahydro-tic isoquinoline-3-carboxylic acid β-2-thienylalanine, methionine sulfoxide, homoarginine, N-acetyl lysine, 2,4-diamino butyric acid, p-aminophenylalanine, N-methylvaline, homocysteine, homoserine, ϵ-amino hexanoic acid, δ-amino valeric acid, 2,3-diaminobutyric acid and mixtures thereof.

Commonly-encountered amino acids that are not genetically encoded and which can be present, or substituted for an amino acid in an analog of an antimicrobial peptide of the invention include, but are not limited to, β-alanine (β-Ala) and other omega-amino acids such as 3-aminopropionic acid (Dap), 2,3-diaminopropionic acid (Dpr), 4-aminobutyric acid and so forth; α-aminoisobutyric acid (Aib); ϵ-aminohexanoic acid (Aha); δ-aminovaleric acid (Ava); methylglycine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); 2-naphthylalanine (2-Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); .beta.-2-thienylalanine (Thi); methionine sulfoxide (MSO); homoarginine (hArg); N-acetyl lysine (AcLys); 2,3-diaminobutyric acid (Dab); 2,3-diaminobutyric acid (Dbu); p-aminophenylalanine (Phe (pNH$_2$)); N-methyl valine (MeVal); homocysteine (hCys) and homoserine (hSer).

Other amino acid residues that are useful for making the peptides and peptide analogs described herein can be found, e.g., in Fasman, 1989, CRC Practical Handbook of Biochemistry and Molecular Biology, CRC Press, Inc., and the references cited therein.

The present invention additionally encompasses an isostere of a peptide described herein. The term "isostere" as used herein is intended to include a chemical structure that can be substituted for a second chemical structure because the steric conformation of the first structure fits a binding site specific for the second structure. The term specifically includes peptide back-bone modifications (i.e., amide bond mimetics) known to those skilled in the art. Such modifications include modifications of the amide nitrogen, the α-carbon, amide carbonyl, complete replacement of the amide bond, extensions, deletions or backbone crosslinks. Several peptide backbone modifications are known, including ψ[CH$_2$S], ψ[CH$_2$NH], ψ[CSNH$_2$], ψ[NHCO], ψ[COCH$_2$], and ψ[(E) or (Z) CH=CH]. In the nomenclature used above, ψ indicates the absence of an amide bond. The structure that replaces the amide group is specified within the brackets.

Other modifications include, for example, an N-alkyl (or aryl) substitution (ψ [CONR]), or backbone cross-linking to construct lactams and other cyclic structures. Other derivatives of the modulator compounds of the invention include C-terminal hydroxymethyl derivatives, O-modified derivatives (e.g., C-terminal hydroxymethyl benzyl ether), N-terminally modified derivatives including substituted amides such as alkylamides and hydrazides.

In another embodiment, the peptide analog is a retro peptide analog (Goodman et al., *Accounts of Chemical Research*, 12:1-7, 1979). A retro peptide analog comprises a reversed amino acid sequence of an antimicrobial peptide of the present invention. For example, a retro peptide analog of an antimicrobial peptide of the present comprises an amino acid sequence set forth in SEQ ID NO: 14 or SEQ ID NO: 15 or SEQ ID NO: 16.

In a preferred embodiment, an analog of an antimicrobial peptide of the invention is a retro-inverted peptide (Sela and Zisman, *FASEB J.* 11:449, 1997). Evolution has ensured the almost exclusive occurrence of L-amino acids in naturally occurring proteins. As a consequence, virtually all proteases cleave peptide bonds between adjacent L-amino acids. Accordingly, artificial proteins or peptides composed of D-amino acids are preferably resistant to proteolytic breakdown. Retro-inverted peptide analogs are isomers of linear peptides in which the direction of the amino acid sequence is reversed (retro) and the chirality, D- or L-, of one or more amino acids therein is inverted (inverso) e.g., using D-amino acids rather than L-amino acids, e.g., Jameson et al., *Nature*, 368, 744-746 (1994); Brady et al., *Nature*, 368, 692-693 (1994). The net result of combining D-enantiomers and reverse synthesis is that the positions of carbonyl and amino groups in each amide bond are exchanged, while the position of the side-chain groups at each alpha carbon is preserved.

An advantage of retro-inverted peptides is their enhanced activity in vivo due to improved resistance to proteolytic degradation, i.e., the peptide has enhanced stability. (e.g., Chorev et al., Trends Biotech. 13, 438-445, 1995).

Retro-inverted peptide analogs may be complete or partial. Complete retro-inverted peptides are those in which a complete sequence of an antimicrobial peptide of the invention is reversed and the chirality of each amino acid in a sequence is inverted e.g., a peptide comprising an amino acid sequence set forth in SEQ ID NO: 14 or SEQ ID NO: 15 or SEQ ID NO: 26 or SEQ ID NO: 27 or SEQ ID NO: 39. Partial retro-inverted peptide analogs are those in which some or all of the peptide bonds are reversed (i.e., completely reversed sequence) and the chirality of some, but not all, amino acid residues is inverted, e.g., a peptide comprising an amino acid sequence set forth in SEQ ID NO: 16 or SEQ ID NO: 17 or SEQ ID NO: 28 or SEQ ID NO: 28 or SEQ ID NO: 40 in which the N-terminal and C-terminal amino acid residues are D-amino acids and the entire sequence is reversed relative to the base peptide sequences of SEQ ID Nos: 1, 2, 18, 19, 30 and 31. Partial retro-inverted peptide analogs can also have only some of the peptide bonds are reversed and the chirality of only those amino acid residues in the reversed portion inverted. For example, one or two or three or four or five or six or seven or eight or nine or ten or eleven or twelve or thirteen or fourteen or fifteen or sixteen or seventeen or eighteen or nineteen or twenty or twenty one or twenty two or twenty three or twenty four or twenty five or twenty six or twenty seven or twenty eight or twenty nine or thirty or thirty one or thirty two or thirty three or thirty four or thirty five or thirty six or thirty seven or thirty eight amino acid residues are D-amino acids. The present invention clearly encompasses both partial and complete retro-inverted peptide analogs.

In another embodiment, an analog of a peptide is modified to reduce the immunogenicity of said analog. Such reduced immunogenicity is useful for a peptide that is to be injected into a subject. Methods for reducing the immunogenicity of a peptide will be apparent to the skilled artisan. For example, an antigenic region of a peptide is predicted using a method known in the art and described, for example, in Kolaskar and Tongaonkar *FEBS Letters*, 276: 172-174, 1990. Any identified antigenic region may then be modified to reduce the immunogenicity of a peptide analog, provided that said analog is an antimicrobial peptide analog. For example, using this method a peptide comprising a sequence set forth in SEQ ID NO: 2 may include an antigenic determinant. However, by modifying the antigenic determinant, the immunogenicity of the peptide is reduced.

Alternatively, or in addition, Tangri et al., *The Journal of Immunology*, 174: 3187-3196, 2005, describe a process for identifying an antigenic site in a peptide and modifying said site to thereby reduce the immunogenicity of the protein without significantly reducing the activity of said protein. The approach is based on 1) the identification of immune-dominant epitopes, e.g., by determining binding to purified HLA molecules; and 2) reducing their binding affinity to HLA-DR molecules to levels below those associated with naturally occurring helper T lymphocyte epitopes. Generally, the approach is based on quantitative determination of HLA-DR binding affinity coupled with confirmation of these epitopes by in vitro immunogenicity testing.

Peptide Derivatives

Preferred derivatives include, for example, a fragment or processed form of an antimicrobial peptide of the invention. For example, an antimicrobial peptide derived from SEQ ID NO: 1 comprises an amino acid sequence set forth in any one of SEQ ID Nos: 2-7; an antimicrobial peptide derived from SEQ ID NO: 18 comprises an amino acid sequence set forth in SEQ ID NO: 19; and an antimicrobial peptide derived from SEQ ID NO: 30 comprises an amino acid sequence set forth in any one of SEQ ID Nos: 31-35.

Preferred derivatives have reduced immunogenicity. For example, by deleting an antigenic determinant from an antimicrobial peptide of the invention, a derivative is produced having reduced immunogenicity. For example, such a derivative comprises an amino acid sequence set forth in SEQ ID NO: 4.

Alternatively, or in addition, a preferred derivative of an antimicrobial peptide of the invention has enhanced antimicrobial activity.

Alternatively, or in addition, a preferred derivative of an antimicrobial peptide of the invention has enhanced stability. For example, a cleavage site of a protease active in a subject to which a peptide is to be administered is mutated and/or deleted to produce a stable derivative of an antimicrobial peptide of the invention.

Methods for producing additional derivatives of an antimicrobial peptide of the invention will be apparent to the skilled artisan and include recombinant methods. For example, a nucleic acid encoding an antimicrobial peptide of the invention or an analog thereof is amplified using mutagenic PCR and the resulting nucleic acid expressed to produce a peptide using a method known in the art and/or described herein.

In a preferred embodiment, the nucleic acid fragments are modified by amplifying a nucleic acid fragment using mutagenic PCR. Such methods include a process selected from the group consisting of: (i) performing the PCR reaction in the presence of manganese; and (ii) performing the PCR in the presence of a concentration of dNTPs sufficient to result in mis-incorporation of nucleotides.

Methods of inducing random mutations using PCR are known in the art and are described, for example, in Dieffenbach (ed) and Dveksler (ed) (In: PCR Primer: A Laboratory Manual, Cold Spring Harbour Laboratories, NY, 1995). Furthermore, commercially available kits for use in mutagenic PCR are obtainable, such as, for example, the Diversify PCR Random Mutagenesis Kit (Clontech) or the GeneMorph Random Mutagenesis Kit (Stratagene).

In one embodiment, PCR reactions are performed in the presence of at least about 200 µM manganese or a salt thereof, more preferably at least about 300 µM manganese or a salt thereof, or even more preferably at least about 500 µM or at least about 600 µM manganese or a salt thereof. Such concentrations manganese ion or a manganese salt induce from about 2 mutations per 1000 base pairs (bp) to about 10 mutations every 1000 bp of amplified nucleic acid (Leung et al *Technique* 1, 11-15, 1989).

In another embodiment, PCR reactions are performed in the presence of an elevated or increased or high concentration of dGTP. It is preferred that the concentration of dGTP is at least about 25 µM, or more preferably between about 50 µM and about 100 µM. Even more preferably the concentration of dGTP is between about 100 µM and about 150 µM, and still more preferably between about 150 µM and about 200 µM. Such high concentrations of dGTP result in the mis-incorporation of nucleotides into PCR products at a rate of between about 1 nucleotide and about 3 nucleotides every 1000 bp of amplified nucleic acid (Shafkhani et al *BioTechniques* 23, 304-306, 1997).

PCR-based mutagenesis is preferred for the mutation of the nucleic acid fragments of the present invention, as increased mutation rates are achieved by performing additional rounds of PCR.

Alternatively, or in addition, a nucleic acid encoding an antimicrobial peptide of the invention or a derivative thereof is inserted or introduced into a host cell that is capable of mutating nucleic acid. Such host cells are generally deficient in one or more enzymes, such as, for example, one or more recombination or DNA repair enzymes, thereby enhancing the rate of mutation to a rate that is rate approximately 5,000 to 10,000 times higher than for non-mutant cells. Strains particularly useful for the mutation of nucleic acids carry alleles that modify or inactivate components of the mismatch repair pathway. Examples of such alleles include alleles selected from the group consisting of mutY, mutM, mutD, mutT, mutA, mutC and mutS. Bacterial cells that carry alleles that modify or inactivate components of the mismatch repair pathway are known in the art, such as, for example the XL-1Red, XL-mutS and XL-mutS-Kanr bacterial cells (Stratagene).

Alternatively the nucleic acid is cloned into a nucleic acid vector that is preferentially replicated in a bacterial cell by the repair polymerase, Pol I. By way of exemplification, a Pol I variant strain will induce a high level of mutations in the introduced nucleic acid vector, thereby enhancing sequence diversity of the nucleic acid encoding the antimicrobial peptide or derivative thereof. Such a method is described, for example, in Fabret et al (In: *Nucl Acid Res,* 28: 1-5 2000).

Alternatively, derivatives of an antimicrobial peptide of the present invention can be generated through DNA shuffling, e.g., as disclosed in Stemmer, *Nature* 370:389-91, 1994, Stemmer, *Proc. Natl. Acad. Sci. USA* 91:10747-51, 1994 and WO 97/20078. Briefly, nucleic acid encoding a derivative of the invention is generated by in vitro homologous recombination by random fragmentation of a parent DNA (e.g., encoding an antimicrobial peptide of the invention) followed by reassembly using PCR, resulting in randomly introduced mutations. This technique can be modified by using a family of parent DNAs, such as, for example, nucleic acid encoding another antimicrobial peptide, to introduce additional variability into the process. Reassembled nucleic acids are then expressed to produce a derivative peptide and assessed for antimicrobial activity and/or reduced immunogenicity and/or resistance to degradation using a method known in the art and/or described herein. Screening for the desired activity, followed by additional iterations of mutagenesis and assay provides for rapid "evolution" of sequences by selecting for desirable mutations while simultaneously selecting against detrimental changes.

For example, a derivative of the invention is produced by combining nucleic acids encoding two or more antimicrobial peptides of the invention, or nucleic acid encoding one or more antimicrobial peptides of the invention and nucleic acid encoding another antimicrobial peptide in a reaction vessel. The nucleic acids are then digested using a nuclease (e.g., DNase I). The resulting fragments are then reassembled by repeated cycles of denaturing and annealing in the presence of a DNA polymerase. Homologous regions of fragments then induce DNA replication of fragments, e.g., from different source templates, to thereby regenerate a nucleic acid encoding a peptide analog. Such a method is described, for example, in Stemmer, *Proc. Natl. Acad. Sci. USA* 91:10747-51, 1994. An analog produced using this method may then be screened for antimicrobial activity, e.g., using a method described herein.

The present invention additionally encompasses the production of a derivative of an antimicrobial peptide of the invention by performing a combination of random mutagenesis and DNA shuffling.

Alternatively, a derivative of an antimicrobial peptide of the invention is produced by performing site-directed mutagenesis. Suitable methods of site-directed mutagenesis are known in the art and/or described in Dieffenbach (ed) and Dveksler (ed) (In: PCR Primer: A Laboratory Manual, Cold Spring Harbour Laboratories, NY, 1995).

Peptide derivatives of the present invention also encompass an antimicrobial peptide or an analog thereof as described herein in any embodiment that is modified to contain one or more-chemical moieties other than an amino acid. The chemical moiety may be linked covalently to the peptide or analog e.g., via an amino terminal amino acid residue, a carboxy terminal amino acid residue, or at an internal amino acid residue. Such modifications include the addition of a protective or capping group on a reactive moiety in the peptide, addition of a detectable label, and other changes that do not adversely destroy the activity of the peptide compound (e.g., its antimicrobial activity).

An "amino terminal capping group" of a peptide compound described herein is any chemical compound or moiety that is covalently linked or conjugated to the amino terminal amino acid residue of a peptide or analog. An amino-terminal capping group may be useful to inhibit or prevent intramolecular cyclization or intermolecular polymerization, to protect the amino terminus from an undesirable reaction with other molecules, or to provide a combination of these properties. A peptide compound of this invention that possesses an amino terminal capping group may possess other beneficial activities as compared with the uncapped peptide, such as enhanced efficacy or reduced side effects. Examples of amino terminal capping groups that are useful in preparing peptide derivatives according to the invention include, but are not limited to, 1 to 6 naturally occurring L-amino acid residues, preferably, 1-6 lysine residues, 1-6 arginine residues, or a combination of lysine and arginine residues; urethanes; urea compounds; lipoic acid ("Lip"); glucose-3-O-glycolic acid moiety ("Gga"); or an acyl group that is covalently linked to the amino terminal amino acid residue of a peptide, wherein such acyl groups useful in the compositions of the invention may have a carbonyl group and a hydrocarbon chain that ranges from one carbon atom (e.g., as in an acetyl moiety) to up to 25 carbons (e.g., palmitoyl group, "Palm" (16:0) and docosahexaenoyl group, "DHA" (C22:6-3)). Furthermore, the carbon chain of the acyl group may be saturated, as in Palm, or unsaturated, as in DHA. It is understood that when an acid, such as docosahexaenoic acid, palmitic acid, or lipoic acid is designated as an amino terminal capping group, the resultant peptide compound is the condensed product of the uncapped peptide and the acid.

A "carboxy terminal capping group" of a peptide compound described herein is any chemical compound or moiety that is covalently linked or conjugated to the carboxy terminal amino acid residue of the peptide compound. The primary purpose of such a carboxy terminal capping group is to inhibit or prevent intramolecular cyclization or intermolecular polymerization, to promote transport of the peptide compound across the blood-brain barrier, and to provide a combination of these properties. A peptide compound of this invention possessing a carboxy terminal capping group may also possess other beneficial activities as compared with the uncapped peptide, such as enhanced efficacy, reduced side effects, enhanced hydrophilicity, enhanced hydrophobicity. Carboxy terminal capping groups that are particularly useful in the peptide compounds described herein include primary or secondary amines that are linked by an amide bond to the α-carboxyl group of the carboxy terminal amino acid of the peptide compound. Other carboxy terminal capping groups useful in the invention include aliphatic primary and secondary alcohols and aromatic phenolic derivatives, including flavenoids, with 1 to 26 carbon atoms, which form esters when linked to the carboxylic acid group of the carboxy terminal amino acid residue of a peptide compound described herein.

Other chemical modifications of a peptide or analog, include, for example, glycosylation, acetylation (including N-terminal acetylation), carboxylation, carbonylation, phosphorylation, PEGylation, amidation, addition of trans olefin, substitution of α-hydrogens with methyl groups, derivatization by known protecting/blocking groups, circularization, inhibition of proteolytic cleavage (e.g., using D amino acids), linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$, acetylation, formylation, oxidation, reduction, etc.

Fusion Proteins and Complexes

1. Tags

The present invention provides an additional derivative of an antimicrobial peptide of the invention, such as, for example a fusion protein comprising one or more of the antimicrobial peptides and/or analogs of the invention. For example, the antimicrobial peptide or analog is fused to a tag or label. Such a tag or label facilitates purification or isolation of the antimicrobial peptide and/or analog and/or derivative or detection of the peptide, analog or derivative. Suitable tags will be apparent to the skilled artisan and include, for example, influenza virus hemagglutinin (HA) (SEQ ID NO: 41), Simian Virus 5 (V5) (SEQ ID NO: 42), polyhistidine (SEQ ID NO: 43), c-myc (SEQ ID NO: 44) or FLAG (SEQ ID NO: 45).

2. Multimeric Proteins

In another embodiment, a fusion protein of the present invention comprises a plurality of antimicrobial peptides of the invention and/or analogs thereof. In this respect, the fusion protein may comprise multiple copies of the same antimicrobial peptide or analog and/or a plurality of antimicrobial peptides and/or analogs (whether present in a single copy or a plurality of copies). For example, the fusion protein comprises an amino acid sequence selected from the group consisting of:

(i) SEQ ID NO: 2 and SEQ ID NO: 19;
(ii) SEQ ID NO: 2 and SEQ ID NO: 31;
(iii) SEQ ID NO: 19 and SEQ ID NO: 31;
(iv) SEQ ID NO: 2; SEQ ID NO: 19 and SEQ ID NO: 31;
(v) SEQ ID NO: 2 and SEQ ID NO: 15;
(vi) SEQ ID NO: 2 and SEQ ID NO: 27;
(vii) SEQ ID NO: 2 and SEQ ID NO: 39;
(viii) SEQ ID NO: 19 and SEQ ID NO: 15;
(ix) SEQ ID NO: 19 and SEQ ID NO: 27;
(x) SEQ ID NO: 19 and SEQ ID NO: 39;
(xi) SEQ ID NO: 31 and SEQ ID NO: 15;
(xii) SEQ ID NO: 31 and SEQ ID NO: 27;
(xiii) SEQ ID NO: 31 and SEQ ID NO: 39;
(xiv) SEQ ID NO: 2; SEQ ID NO: 15 and SEQ ID NO: 27;
(xv) SEQ ID NO: 2; SEQ ID NO: 15 and SEQ ID NO: 39;
(xvi) SEQ ID NO: 2; SEQ ID NO: 27 and SEQ ID NO: 39;
(xvii) SEQ ID NO: 2; SEQ ID NO: 15; SEQ ID NO: 27; and SEQ ID NO: 39;
(xviii) SEQ ID NO: 19; SEQ ID NO: 15 and SEQ ID NO: 27;
(xix) SEQ ID NO: 19; SEQ ID NO: 15 and SEQ ID NO: 39;
(xx) SEQ ID NO: 19; SEQ ID NO: 27 and SEQ ID NO: 39;
(xxi) SEQ ID NO: 19; SEQ ID NO: 15; SEQ ID NO: 27; and SEQ ID NO: 39;
(xxii) SEQ ID NO: 31; SEQ ID NO: 15 and SEQ ID NO: 27;
(xxiii) SEQ ID NO: 31; SEQ ID NO: 15 and SEQ ID NO: 39;

(xxiv) SEQ ID NO: 31; SEQ ID NO: 27 and SEQ ID NO: 39;
(xxv) SEQ ID NO: 31; SEQ ID NO: 15; SEQ ID NO: 27; and SEQ ID NO: 39;
(xxvi) SEQ ID NO: 2; SEQ ID NO: 19; SEQ ID NO: 15 and SEQ ID NO: 27;
(xxvii) SEQ ID NO: 2; SEQ ID NO: 19; SEQ ID NO: 15 and SEQ ID NO: 39;
(xxviii) SEQ ID NO: 2; SEQ ID NO: 19; SEQ ID NO: 27 and SEQ ID NO: 39;
(xxix) SEQ ID NO: 2; SEQ ID NO: 19; SEQ ID NO: 15; SEQ ID NO: 27; and SEQ ID NO: 39;
(xxx) SEQ ID NO: 2; SEQ ID NO: 31; SEQ ID NO: 15 and SEQ ID NO: 27;
(xxxi) SEQ ID NO: 2; SEQ ID NO: 31; SEQ ID NO: 15 and SEQ ID NO: 39;
(xxxii) SEQ ID NO: 2; SEQ ID NO: 31; SEQ ID NO: 27 and SEQ ID NO: 39;
(xxxiii) SEQ ID NO: 2; SEQ ID NO: 31; SEQ ID NO: 15; SEQ ID NO: 27; and SEQ ID NO: 39;
(xxxiv) SEQ ID NO: 19, SEQ ID NO: 31; SEQ ID NO: 15 and SEQ ID NO: 27;
(xxxv) SEQ ID NO: 19; SEQ ID NO: 31; SEQ ID NO: 15 and SEQ ID NO: 39;
(xxxvi) SEQ ID NO: 19; SEQ ID NO: 31; SEQ ID NO: 27 and SEQ ID NO: 39;
(xxxvi) SEQ ID NO: 19; SEQ ID NO: 31; SEQ ID NO: 15; SEQ ID NO: 27; and SEQ ID NO: 39;
(xxxvii) SEQ ID NO: 2; SEQ ID NO: 19; SEQ ID NO: 31; SEQ ID NO: 15; SEQ ID NO: 27; and SEQ ID NO: 39;
(xxxix) SEQ ID NO: 15 and SEQ ID NO: 27;
(xl) SEQ ID NO: 15 and SEQ ID NO: 39;
(xli) SEQ ID NO: 27 and SEQ ID NO: 39;
(xlii) SEQ ID NO: 15, SEQ ID NO: 27 and SEQ ID NO: 39; and
(xliii) combinations of any one or more of (i) to (xlii).

In one embodiment, such a fusion protein comprises one or more additional components, such as, for example, a tag or label and/or an additional antimicrobial peptide or analog or derivative thereof.

3. Inhibitors of Antimicrobial Activity

In another embodiment, a derivative of an antimicrobial peptide of the invention additionally comprises an inhibitor of the antimicrobial activity of the peptide, analog or derivative. Such an inhibitor is useful, for example, for maintaining a peptide or analog of the invention in an inactive state until antimicrobial activity s required, for example, until the peptide is administered to a subject suffering from an infection.

In one embodiment, the inhibitor is a peptide or a polypeptide. For example, the inhibitor comprises an amino acid sequence set forth in any one of SEQ ID Nos: 46 to 51. For example, the fusion protein comprises an amino acid sequence set forth in SEQ ID NO: 2 and SEQ ID NO: 46 or SEQ ID NO: 49. Alternatively, the fusion protein comprises an amino acid sequence set forth in SEQ ID NO: 19 and SEQ ID NO: 47 or SEQ ID NO: 50. Alternatively, the fusion protein comprises an amino acid sequence set forth in SEQ ID NO: 31 and SEQ ID NO: 48 or SEQ ID NO: 51.

Preferably, such an inhibitor is linked to the antimicrobial peptide of the invention or analog thereof by a region comprising a cleavage site of a protease that is active in an infection by a microorganism. In this manner, during an infection the antimicrobial peptide, analog or derivative is separated from the inhibitor thereby facilitating its activity for the treatment of an infection.

4. Linkers

Each of the components of a derivative of an antimicrobial peptide of the invention may optionally be separated by a linker that facilitates the independent folding of each of said components. A suitable linker will be apparent to the skilled artisan. For example, it is often unfavourable to have a linker sequence with high propensity to adopt α-helix or β-strand structures, which could limit the flexibility of the protein and consequently its functional activity. Rather, a more desirable linker is a sequence with a preference to adopt extended conformation. In practice, most currently designed linker sequences have a high content of glycine residues that force the linker to adopt loop conformation. Glycine is generally used in designed linkers because the absence of a β-carbon permits the polypeptide backbone to access dihedral angles that are energetically forbidden for other amino acids.

Preferably, the linker is hydrophilic, i.e. the residues in the linker are hydrophilic.

Linkers comprising glycine and/or serine have a high freedom degree for linking of two proteins, i.e., they enable the fused proteins to fold and produce functional proteins. Robinson and Sauer *Proc. Natl. Acad. Sci.* 95: 5929-5934, 1998 found that it is the composition of a linker peptide that is important for stability and folding of a fusion protein rather than a specific sequence. For example, the authors found that a fusion protein comprising a linker consisting almost entirely of glycine was unstable. Accordingly, the use of amino acid residues other than glycine, such as, for example, alanine or serine, is also useful for the production of a linker.

In one embodiment, the linker is a glycine rich linker. Preferably, the linker is a glycine linker that additionally comprises alanine and/or serine.

5. Complexes

Without being bound by theory or mode of action a complex of antimicrobial peptides may enhance the antimicrobial activity of said peptides. Accordingly, the present invention also provides a derivative of an antimicrobial peptide of the invention comprising a complex of antimicrobial peptides and/or analogs thereof as described herein in any embodiment. In this resect, such a complex may comprise a plurality of the same or different peptides and/or analogs of the invention. Such a complex is formed, for example, by the direct attachment of the monomers to each other or to substrate, including, for example, peptides attached to a polymer scaffold, e.g., a PEG scaffold.

Peptide Synthesis

An antimicrobial peptide of the invention or an analog or derivative thereof is preferably synthesized using a chemical method known to the skilled artisan. For example, synthetic peptides are prepared using known techniques of solid phase, liquid phase, or peptide condensation, or any combination thereof, and can include natural and/or unnatural amino acids. Amino acids used for peptide synthesis may be standard Boc (Nα-amino protected Nα-t-butyloxycarbonyl) amino acid resin with the deprotecting, neutralization, coupling and wash protocols of the original solid phase procedure of Merrifield, J. Am. Chem. Soc., 85:2149-2154, 1963, or the base-labile Nα-amino protected 9-fluorenylmethoxycarbonyl (Fmoc) amino acids described by Carpino and Han, J. Org. Chem., 37:3403-3409, 1972. Both Fmoc and Boc Nα-amino protected amino acids can be obtained from various commercial sources, such as, for example, Fluka, Bachem, Advanced Chemtech, Sigma, Cambridge Research Biochemical, Bachem, or Peninsula Labs.

Generally, chemical synthesis methods comprise the sequential addition of one or more amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions that allow for the formation of an amide linkage. The protecting group is then removed from the newly added amino acid residue and the next amino acid (suitably protected) is then added, and so forth. After the desired amino acids have been linked in the proper sequence, any remaining protecting groups (and any solid support, if solid phase synthesis techniques are used) are removed sequentially or concurrently, to render the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide. See, e.g., J. M. Stewart and J. D. Young, Solid Phase Peptide Synthesis (Pierce Chemical Co., Rockford, Ill. 1984) and G. Barany and R. B. Merrifield, The Peptides: Analysis, Synthesis, Biology, editors E. Gross and J. Meienhofer, Vol. 2, (Academic Press, New York, 1980), pp. 3-254, for solid phase peptide synthesis techniques; and M. Bodansky, Principles of Peptide Synthesis, (Springer-Verlag, Berlin 1984) and E. Gross and J. Meienhofer, Eds., The Peptides: Analysis. Synthesis. Biology, Vol. 1, for classical solution synthesis. These methods are suitable for synthesis of an antimicrobial peptide of the present invention or an analog or derivative thereof.

Typical protecting groups include t-butyloxycarbonyl (Boc), 9-fluorenylmethoxycarbonyl (Fmoc) benzyloxycarbonyl (Cbz); p-toluenesulfonyl (Tx); 2,4-dinitrophenyl; benzyl (Bzl); biphenylisopropyloxycarboxy-carbonyl, t-amyloxycarbonyl, isobornyloxycarbonyl, o-bromobenzyloxycarbonyl, cyclohexyl, isopropyl, acetyl, o-nitrophenylsulfonyl and the like.

Typical solid supports are cross-linked polymeric supports. These can include divinylbenzene cross-linked-styrene-based polymers, for example, divinylbenzene-hydroxymethylstyrene copolymers, divinylbenzene-chloromethylstyrene copolymers and divinylbenzene-benzhydrylaminopolystyrene copolymers.

The antimicrobial peptide, analog or derivative of the present invention can also be chemically prepared by other methods such as by the method of simultaneous multiple peptide synthesis. See, e.g., Houghten *Proc. Natl. Acad. Sci. USA* 82: 5131-5135, 1985 or U.S. Pat. No. 4,631,211.

As will be apparent to the skilled artisan based on the description herein, an analog or derivative of an antimicrobial of the invention may comprise D-amino acids, a combination of D- and L-amino acids, and various unnatural amino acids (e.g., α-methyl amino acids, Cα-methyl amino acids, and Nα-methyl amino acids, etc) to convey special properties. Synthetic amino acids include omithine for lysine, fluorophenylalanine for phenylalanine, and norleucine for leucine or isoleucine.

Methods for the synthesis of such peptides will be apparent to the skilled artisan based on the foregoing.

Recombinant Peptide Production

In one embodiment, an antimicrobial peptide or analog or derivative thereof or fusion protein comprising same is produced as a recombinant protein. To facilitate the production of a recombinant peptide or fusion protein nucleic acid encoding same is preferably isolated or synthesized. Typically the nucleic acid encoding the constituent components of the fusion protein is/are isolated using a known method, such as, for example, amplification (e.g., using PCR or splice overlap extension) or isolated from nucleic acid from an organism using one or more restriction enzymes or isolated from a library of nucleic acids. Methods for such isolation will be apparent to the ordinary skilled artisan and/or described in Ausubel et al (In: Current Protocols in Molecular Biology. Wiley Interscience, ISBN 047 150338, 1987), Sambrook et al (In: Molecular Cloning: Molecular Cloning: A Laboratory Manual, Cold Spring Harbor Laboratories, New York, Third Edition 2001).

For example, nucleic acid (e.g., genomic DNA or RNA that is then reverse transcribed to form cDNA) from a cell or organism capable of expressing an antimicrobial peptide of the invention is isolated using a method known in the art and cloned into a suitable vector. The vector is then introduced into a suitable organism, such as, for example, a bacterial cell. Using a nucleic acid probe from a known antimicrobial peptide encoding gene a cell comprising the nucleic acid of interest is isolated using methods known in the art and described, for example, in Ausubel et al (In: Current Protocols in Molecular Biology. Wiley Interscience, ISBN 047 150338, 1987), Sambrook et al (In: Molecular Cloning: Molecular Cloning: A Laboratory Manual, Cold Spring Harbor Laboratories, New York, Third Edition 2001).

Alternatively, nucleic acid encoding an antimicrobial peptide of the invention is isolated using polymerase chain reaction (PCR). Methods of PCR are known in the art and described, for example, in Dieffenbach (ed) and Dveksler (ed) (In: PCR Primer: A Laboratory Manual, Cold Spring Harbour Laboratories, NY, 1995). Generally, for PCR two non-complementary nucleic acid primer molecules comprising at least about 20 nucleotides in length, and more preferably at least 25 nucleotides in length are hybridized to different strands of a nucleic acid template molecule, and specific nucleic acid molecule copies of the template are amplified enzymatically. Preferably, the primers hybridize to nucleic acid adjacent to a nucleic acid encoding an antimicrobial peptide of the invention, thereby facilitating amplification of the nucleic acid that encodes the subunit. Following amplification, the amplified nucleic acid is isolated using a method known in the art and, preferably cloned into a suitable vector.

Other methods for the production of a nucleic acid of the invention will be apparent to the skilled artisan and are encompassed by the present invention.

For expressing protein by recombinant means, a protein-encoding nucleotide sequence is placed in operable connection with a promoter or other regulatory sequence capable of regulating expression in a cell-free system or cellular system. For example, nucleic acid comprising a sequence that encodes an antimicrobial peptide of the present invention in operable connection with a suitable promoter is expressed in a suitable cell for a time and under conditions sufficient for expression to occur. Nucleic acid encoding an antimicrobial protein of the present invention is readily derived from the publicly available amino acid sequence.

As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid (e.g., a transgene), e.g., in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid (e.g., a transgene and/or a selectable marker gene and/or a detectable marker gene) to which it is operably linked. Preferred promoters can contain additional copies of one or more specific regulatory elements to further enhance expression and/or alter the spatial expression and/or temporal expression of said nucleic acid.

As used herein, the term "in operable connection with" "in connection with" or "operably linked to" means positioning a promoter relative to a nucleic acid (e.g., a transgene) such that expression of the nucleic acid is controlled by the promoter. For example, a promoter is generally positioned 5' (upstream) to the nucleic acid, the expression of which it controls. To construct heterologous promoter/nucleic acid combinations (e.g., promoter/transgene and/or promoter/selectable marker gene combinations), it is generally preferred to position the promoter at a distance from the gene transcription start site that is approximately the same as the distance between that promoter and the nucleic acid it controls in its natural setting, i.e., the gene from which the promoter is derived. As is known in the art, some variation in this distance can be accommodated without loss of promoter function.

Should it be preferred that a peptide or fusion protein of the invention is expressed in vitro a suitable promoter includes, but is not limited to a T3 or a T7 bacteriophage promoter (Hanes and Plückthun *Proc. Natl. Acad. Sci. USA*, 94 4937-4942 1997).

Typical expression vectors for in vitro expression or cell-free expression have been described and include, but are not limited to the TNT T7 and TNT T3 systems (Promega), the pEXP1-DEST and pEXP2-DEST vectors (Invitrogen).

Typical promoters suitable for expression in bacterial cells include, but are not limited to, the lacz promoter, the Ipp promoter, temperature-sensitive $\lambda L$ or $\lambda R$ promoters, T7 promoter, T3 promoter, SP6 promoter or semi-artificial promoters such as the IPTG-inducible tac promoter or lacUV5 promoter. A number of other gene construct systems for expressing the nucleic acid fragment of the invention in bacterial cells are well-known in the art and are described for example, in Ausubel et al (In: Current Protocols in Molecular Biology. Wiley Interscience, ISBN 047 150338, 1987), U.S. Pat. No. 5,763,239 (Diversa Corporation) and Sambrook et al (In: Molecular Cloning: Molecular Cloning: A Laboratory Manual, Cold Spring Harbor Laboratories, New York, Third Edition 2001).

Numerous expression vectors for expression of recombinant polypeptides in bacterial cells and efficient ribosome binding sites have been described, and include, for example, PKC30 (Shimatake and Rosenberg, Nature 292, 128, 1981); pKK173-3 (Amann and Brosius, Gene 40, 183, 1985), pET-3 (Studier and Moffat, J. Mol. Biol. 189, 113, 1986); the pCR vector suite (Invitrogen), pGEM-T Easy vectors (Promega), the pL expression vector suite (Invitrogen) the pBAD/TOPO or pBAD/thio—TOPO series of vectors containing an arabinose-inducible promoter (Invitrogen, Carlsbad, Calif.), the latter of which is designed to also produce fusion proteins with a Trx loop for conformational constraint of the expressed protein; the pFLEX series of expression vectors (Pfizer nc., CT, USA); the pQE series of expression vectors (QIAGEN, CA, USA), or the pL series of expression vectors (Invitrogen), amongst others.

Typical promoters suitable for expression in viruses of eukaryotic cells and eukaryotic cells include the SV40 late promoter, SV40 early promoter and cytomegalovirus (CMV) promoter, CMV IE (cytomegalovirus immediate early) promoter amongst others. Preferred vectors for expression in mammalian cells (e.g., 293, COS, CHO, 10T cells, 293T cells) include, but are not limited to, the pcDNA vector suite supplied by Invitrogen, in particular pcDNA 3.1 myc-His-tag comprising the CMV promoter and encoding a C-terminal 6×His and MYC tag; and the retrovirus vector pSR$\alpha$tkneo (Muller et al., *Mol. Cell. Biol.*, 11, 1785, 1991).

A wide range of additional host/vector systems suitable for expressing an antimicrobial peptide or fusion protein of the present invention are available publicly, and described, for example, in Sambrook et al (In: Molecular cloning, A laboratory manual, second edition, Cold Spring Harbor Laboratory, Cold Spring Harbor, N.Y., 1989).

Means for introducing the isolated nucleic acid molecule or a gene construct comprising same into a cell for expression are well-known to those skilled in the art. The technique used for a given organism depends on the known successful techniques. Means for introducing recombinant DNA into cells include microinjection, transfection mediated by DEAE-dextran, transfection mediated by liposomes such as by using lipofectamine (Gibco, Md., USA) and/or cellfectin (Gibco, Md., USA), PEG-mediated DNA uptake, electroporation and microparticle bombardment such as by using DNA-coated tungsten or gold particles (Agracetus Inc., WI, USA) amongst others.

Peptide/Analog/Derivative/Fusion Protein Isolation

Following production/expression/synthesis, an antimicrobial peptide of the invention or derivative or analog thereof or fusion protein comprising same is purified using a method known in the art. Such purification preferably provides a peptide of the invention substantially free of conspecific protein, acids, lipids, carbohydrates, and the like. Antibodies and other affinity ligands are particularly preferred for producing isolated protein. Preferably, the protein will be in a preparation wherein more than about 90% (e.g. 95%, 98% or 99%) of the protein in the preparation is an antimicrobial peptide of the invention or derivative or analog thereof or fusion protein comprising same.

Standard methods of peptide purification are employed to obtain an isolated peptide of the invention, including but not limited to various high-pressure (or performance) liquid chromatography (HPLC) and non-HPLC peptide isolation protocols, such as size exclusion chromatography, ion exchange chromatography, phase separation methods, electrophoretic separations, precipitation methods, salting in/out methods, immunochromatography, and/or other methods.

A preferred method of isolating peptide compounds useful in compositions and methods of the invention employs reversed-phase HPLC using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can also be used to separate a peptide based on its charge.

Alternatively, affinity purification is useful for isolating a fusion protein comprising a label. Methods for isolating a protein using affinity chromatography are known in the art and described, for example, in Scopes (In: Protein purification: principles and practice, Third Edition, Springer Verlag, 1994). For example, an antibody or compound that binds to the label (in the case of a polyhistidine tag this may be, for example, nickel-NTA) is preferably immobilized on a solid support. A sample comprising a fusion protein is then contacted to the immobilized antibody or compound for a time and under conditions sufficient for binding to occur. Following washing to remove any unbound or non-specifically bound protein, the fusion protein is eluted.

The degree of purity of the peptide compound may be determined by various methods, including identification of a major large peak on HPLC. A peptide compound that produces a single peak that is at least 95% of the input material on an HPLC column is preferred. Even more preferable is a polypeptide that produces a single peak that is at least 97%, at least 98%, at least 99% or even 99.5% of the input material on an HPLC column.

To ensure that a peptide obtained using any of the techniques described above is the desired peptide for use in compositions and methods of the present invention, analysis of the composition of the peptide is determined by any of a variety of analytical methods known in the art. Such composition analysis may be conducted using high resolution mass spectrometry to determine the molecular weight of the peptide. Alternatively, the amino acid content of a peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine the sequence of the peptide. Since some of the peptide compounds contain amino and/or carboxy terminal capping groups, it may be necessary to remove the capping group or the capped amino acid residue prior to a sequence analysis. Thin-layer chromatographic methods may also be used to authenticate one or more constituent groups or residues of a desired peptide.

Determining the Antimicrobial Activity of a Peptide

Methods for determining the antimicrobial activity of a peptide will be apparent to the skilled artisan, for example, based on the description herein. For example, as exemplified herein, the present inventors have used a radial diffusion assay.

Other suitable methods include, for example, a broth dilution method. Essentially, this method involves growing a microorganism in liquid media until log phase is reached. The peptide, analog or derivative to be tested is serially diluted in media in which the microorganism is grown are grown and a sample of the microorganism added to the peptide containing sample. The sample is then maintained for a time and under conditions sufficient for growth of the microorganism, and the amount of growth of the microorganism determined relative to a negative control by detecting the absorbance at $A_{600}$.

Another method in accordance with the invention comprises contacting a microorganism previously contacted with a peptide to be tested with an agent that has affinity for a compound located within the microorganism, but is not able to cross an intact or undamaged membrane. The presence of the agent within the microorganism indicates that the agent crossed the membrane indicating that the membrane of the microorganism was damaged by the peptide. An example of such an agent is Sytox green dye (Molecular Probes, Eugene, Oreg.). This dye has a strong affinity for nucleic acids, but can only penetrate cells that have a damaged membrane.

Yet another method for determining whether a peptide being assayed for antimicrobial activity has damaged the membrane of the microorganism involves contacting the microorganism with a test peptide and an agent capable of crossing the membrane of the microorganism. The agent is capable of being processed within the microorganism to form a product that is unable to cross an undamaged membrane. The medium surrounding the microorganism is then assayed for the presence of said product. The presence of said product in the medium in which the microorganism is grown is indicative of damage to the membrane of the microorganism caused by the peptide, and is indicative of the antimicrobial activity of the peptide. An example of a suitable agent is calcein AM. Calcein AM is converted into free calcein within the microorganism. Normally, free calcein is unable to cross the cell membrane of the microorganism and enter the surrounding culture. Thus, detection of free calcein in the medium surrounding the microorganism is indicative of damage to the cell membrane of the microorganism, and thus the antimicrobial activity of the peptide.

Alternatively, or in addition, an antimicrobial peptide of the invention or analog or derivative thereof is administered to an animal model of infection and the effect of the peptide on said infection is determined. Animal models of infection are known in the art and include, for example, primate models of HIV-1 infection (Nathanson *Int J STD AIDS;* 91:3-7, 1989); rat, mouse or monkey models of candidiasis (Samaranayake and Samaranayake *Clinical Microbiology Reviews,* 398-429, 2001); mouse models of *S. aureus* infection (Kuklin et al., *Antimicrobial Agents and Chemotherapy* 47: 2740-2748, 2003); a mouse model of chronic *P. aeruginosa* infection (van Heeckeren, *Lab Anim.* 36: 291-312, 2002, and/or an animal model described in Bacterial Pathogenesis, Part A: Identification And Regulation Of Virulence Factors, 235 (Clark et al., Eds.), Academic Press, 1994.

Compositions Comprising an Antimicrobial Peptide, Analog or Derivative

Preferably, a peptide, analog or derivative of the present invention is provided in a composition, e.g., a pharmaceutical composition, a disinfecting composition, a preservative composition or a phytoprotective composition. Such a composition additionally comprises, for example, a suitable carrier, e.g., pharmaceutically acceptable carrier. The term "carrier" as used herein, refers to a carrier that is conventionally used in the art to facilitate the storage, administration, and/or the biological activity of a regulatory agent. A carrier may also reduce any undesirable side effects of the regulatory agent. A suitable carrier is stable, i.e., incapable of reacting with other ingredients in the formulation. The carrier does not produce significant local or systemic adverse effect in recipients at the dosages and concentrations employed for treatment. Such carriers are generally known in the art. Suitable carriers for this invention include those conventionally used. Water, saline, aqueous dextrose, and glycols are preferred liquid carriers, particularly (when isotonic) for solutions. Alternatively, the carrier is selected from various oils, including those of petroleum, animal, vegetable or synthetic origin, for example, peanut oil, soybean oil, mineral oil, sesame oil, and the like. Suitable pharmaceutical carriers include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like.

A composition comprising an antimicrobial peptide of the invention or a derivative or analog thereof can be subjected to conventional pharmaceutical expedients, such as sterilization, and can contain conventional pharmaceutical additives, such as preservatives, stabilizing agents, wetting, or emulsifying agents, salts for adjusting osmotic pressure, buffers, and the like. Other acceptable components in the composition of the invention include, but are not limited to, isotonicity-modifying agents such as water, saline, and buffers including phosphate, citrate, succinate, acetic acid, and other organic acids or their salts. However, because an antimicrobial peptide of the present invention is a soluble hydrophilic molecule, sprays, solutions, lotions and topical ointments for administration are readily formulated without the need for chemical solvent-based solubilising agents, which may be detrimental to a subject to which the peptide is to be administered.

Preferably, a composition of the invention also includes one or more stabilizers, reducing agents, anti-oxidants and/or anti-oxidant chelating agents. The use of buffers, stabilizers, reducing agents, anti-oxidants and chelating agents in the preparation of protein-based compositions, is known in the art and described, for example, in Wang et al. *J. Parent. Drug Assn.* 34:452-462, 1980; Wang et al. *J. Parent. Sci. Tech.* 42:S4-S26 (Supplement), 1988. Suitable buffers include acetate, adipate, benzoate, citrate, lactate, maleate, phosphate, tartarate, borate, tri(hydroxymethyl aminomethane), succinate, glycine, histidine, the salts of various amino acids, or the like, or combinations thereof. Suitable salts and isotonicifiers include sodium chloride, dextrose, mannitol, sucrose, trehalose, or the like. Where the carrier is a liquid, it is preferred that the carrier is hypotonic or isotonic with oral, conjunctival, or dermal fluids and has a pH within the range of 4.5-8.5. Where the carrier is in powdered form, it is preferred that the carrier is also within an acceptable non-toxic pH range.

In some embodiments, an antimicrobial peptide of the invention or analog or derivative thereof is incorporated within a composition for administration to a mucus membrane, e.g., by nasal administration. Such a composition generally includes a biocompatible polymer functioning as a carrier or base. Such polymer carriers include polymeric powders, matrices or microparticulate delivery vehicles, among other polymer forms. The polymer can be of plant, animal, or synthetic origin. Often the polymer is crosslinked. Additionally, in these delivery systems the biologically active agent, can be functionalized in a manner where it can be covalently bound to the polymer and rendered inseparable from the polymer by simple washing. Polymers useful in this respect are desirably water interactive and/or hydrophilic in nature to absorb significant quantities of water, and they often form hydrogels when placed in contact with water or aqueous media for a period of time sufficient to reach equilibrium with water.

Drug delivery systems based on biodegradable polymers are preferred in many biomedical applications because such systems are broken down either by hydrolysis or by enzymatic reaction into non-toxic molecules. The rate of degradation is controlled by manipulating the composition of the biodegradable polymer matrix. These types of systems can therefore be employed in certain settings for long-term release of biologically active agents. Examples of suitable biodegradable polymers include, for example, poly(glycolic acid) (PGA), poly-(lactic acid) (PLA), and poly(D,L-lactic-co-glycolic acid) (PLGA).

Alternatively, a peptide or analog or derivative thereof of the invention can be administered via in vivo expression of the recombinant protein. In vivo expression can be accomplished via somatic cell expression according to suitable methods (see, e.g. U.S. Pat. No. 5,399,346). In this embodiment, nucleic acid encoding the protein can be incorporated into a retroviral, adenoviral or other suitable vector (preferably, a replication deficient infectious vector) for delivery, or can be introduced into a transfected or transformed host cell capable of expressing the protein for delivery. In the latter embodiment, the cells can be implanted (alone or in a barrier device), injected or otherwise introduced in an amount effective to express the protein in a therapeutically effective amount.

In another embodiment, the antimicrobial peptides of the invention are used in combination with or to enhance the activity of other antimicrobial agents or antibiotics.

Combinations of the peptides with other agents may be useful to allow antibiotics to be used at lower doses due to toxicity concerns, to enhance the activity of antibiotics whose efficacy has been reduced or to effectuate a synergism between the components such that the combination is more effective than the sum of the efficacy of either component independently. Antibiotics that may be combined with an antimicrobial peptide in combination therapy include but are not limited to penicillin, ampicillin, amoxycillin, vancomycin, cycloserine, bacitracin, cephalolsporin, methicillin, streptomycin, kanamycin, tobramycin, gentamicin, tetracycline, chlortetracycline, doxycycline, chloramphenicol, lincomycin, clindamycin, erythromycin, oleandomycin, polymyxin nalidixic acid, rifamycin, rifampicin, gantrisin, trimethoprim, isoniazid, paraminosalicylic acid, and ethambutol.

In another embodiment, the composition is a disinfecting or preservative composition, e.g., for cleaning a surface and/or for preserving food or pharmaceuticals. Such a composition comprises a suitable carrier, such as, for example, as described supra. Such a composition also preferably comprises one or more protease inhibitors to reduce or prevent degradation of the antimicrobial peptide of the invention.

In another embodiment, the composition is a phytoprotective composition. Such a composition is, for example, sprayed onto or applied to a plant or soil in which a plant is grown or is to be grown to prevent a microbial infection or to treat a microbial infection.

As will be apparent to the skilled artisan based on the foregoing, a preferred composition is suitable for spray application. For example, the composition is suitable for spraying onto a food product or onto a food preparation surface or onto a plant. Such spray compositions are useful for the treatment of food, e.g., to prevent food spoilage without actually handling the food. The skilled artisan will be aware of suitable components of a composition suitable for spray application. For example the composition comprises an antimicrobial peptide or analog or derivative as described herein according to any embodiment and a suitable carrier, e.g., water or saline. Such a composition may also comprise, for example, a surfactant, e.g., Tween 20, preferably, a surfactant does not inhibit or reduce the antimicrobial activity of said peptide, analog or derivative.

In some embodiments, a peptide described herein according to any embodiment is applied to a surface of a device to prevent microbial proliferation on that surface of the device. The device is, for example, a medical device, which includes any material or device that is used on, in, or through a patient's body in the course of medical treatment (e.g., for a disease or injury). Medical devices include but are not limited to such items as medical implants, wound care devices, drug delivery devices, and body cavity and personal protection devices. The medical implants include but are not limited to urinary catheters, intravascular catheters, dialysis shunts, wound drain tubes, skin sutures, vascular grafts, implantable meshes, intraocular devices, heart valves, prosthetic devices (e.g., hip prosthetics) and the like. Wound care devices include but are not limited to general wound dressings, biologic graft materials, tape closures and dressings, and surgical incise drapes. Drug delivery devices include but are not limited to needles, drug delivery skin patches, drug delivery mucosal patches and medical sponges.

Reducing or Preventing Microbial Growth

The present inventors have demonstrated that the peptides of the present invention are active against a variety of microorganisms. Accordingly, the peptides of the present invention are useful for, for example, preserving food stuff, e.g., by preventing colonization with a microorganism that causes food-poisoning in a subject or a microorganism that causes food-spoilage. For example, an antimicrobial peptide of the invention is useful for preventing colonization by a bacterium, such as, for example, *Staphylococcus aureus, Salmonella, Clostridium perfringens, Campylobacter, Listeria* monocytogenes, Vibrio parahaemolyticus, Bacillus cereus, and Entero-pathogenic Escherichia coli or a fungus of the genera Aspergillus, Penicillium or Rhizopus.

The antimicrobial peptides of the invention and/or the analogs or derivatives thereof are useful for the treatment of an infection by a microorganism, such as, for example, a virus, a bacterium or a fungus. Organisms against which a peptide, analog or derivative of the invention are active will be apparent to the skilled artisan and include, for example, a virus from a family selected from the group consisting of Astroviridae, Caliciviridae, Picornaviridae, Togaviridae, Flaviviridae, Caronaviridae, Paramyxviridae, Orthomyxoviridae, Bunyaviridae, Arenaviridae, Rhabdoviridae, Filoviridae, Reoviridae, Bornaviridae, Retroviridae, Poxviridae, Herpesviridae, Adenoviridae, Papovaviridae, Parvoviridae, Hepadnaviridae, (eg., a virus selected from the group consisting of a Coxsackie A-24 virus Adenovirus 11, Adenovirus 21, Coxsackie B virus, Borna Diease Virus, Respiratory syncytial virus, Parainfluenza virus, California encephalitis virus, human papilloma virus, varicella zoster virus, Colorado tick fever virus, Herpes Simplex Virus, vaccinia virus, parainfluenza virus 1, parainfluenza virus 2, parainfluenza virus 3, dengue virus, Ebola virus, Parvovirus B19 Coxsackie A-16 virus, HSV-1, hepatitis A virus, hepatitis B virus, hepatitis C virus, hepatitis D virus, hepatitis E virus, human immunodeficiency virus, Coxsackie B1-B5, Influenza viruses A, B or C, LaCross virus, Lassavirus, rubeola virus Coxsackie A or B virus, Echovirus, lymphocytic choriomeningitis virus, HSV-2, mumps virus, Respiratory Synytial Virus, Epstein-Barr Virus, Poliovirus Enterovirus, rabies virus, rubivirus, variola virus, WEE virus, Yellow fever virus and varicella zoster virus).

Preferably, the peptide is useful for the treatment of an infection by a bacterium, such as for example, a gram-positive bacterium or a gram-negative bacterium. For example, the present invention is useful for treating an infection by a bacterium, such as, for example, S. pyrogenes, S. agalactiae, S. equi, S. canis, S. bovis, S. equinus, S. anginosus, S. sanguis, S. salivarius, S. mitis, S. mutans, S pyogenes, Enterococcus faecalis, Enterococcus faecium, Staphylococcus epidermidis, Staphylococcus aureus, Hemophilus influenzae, Pseudomonas aeruginosa, Pseudomonas pseudomallei, Pseudomonas mallei, Brucella melitensis, Brucella suis, Brucella abortus, Bordetella pertussis, Neisseria meningitidis, Neisseria gonorrhoeae, Moraxella catarrhalis, Corynebacterium diphtheriae, Corynebacterium ulcerans, Corynebacterium pseudotuberculosis, Corynebacterium pseudodiphtheriticum, Corynebacterium urealyticum, Corynebacterium hemolyticum, Corynebacterium equi, Listeria monocytogenes, Nocardia asteroides, Bacteroides species, Actinomycetes species, Treponema pallidum, Leptospirosa species, Klebsiella pneumoniae; Escherichia coli, Proteus, Serratia species, Acinetobacter, Yersinia pestis, Francisella tularensis, Enterobacter species, Bacteriodes species or Legionella species Preferably, the antimicrobial peptide of the present invention is useful for treating an infection caused by a bacterium such as, for example, E. coli, Pseudomonas spp., P. vulgaris, P aeruginosa, S. choleraesuis, S. aureus, S. pyogenes or S. equi equi.

The antimicrobial peptide of the present invention is preferably also useful for treating an infection caused by a fungus, such as, for example, Aspergillus sp., Dermatophytes, Blastomyces derinatitidis, Candida sp., Malassezia furfur, Exophiala werneckii, Piedraia hortai, Trichosporon beigelii, Pseudallescheria boydii, Madurella grisea, Histoplasma capsulatum, Sporothrix schenckii, Histoplasma capsulatum T. rubrum, T. interdigitale, T. tonsurans, M. audouini, T. violaceum, M. ferrugineum, T. schoenleinii, T. megninii, T. soudanense, T. yaoundei, M. canis, T. equinum, T. erinacei, T. verrucosum, M. nanum (originating from pigs), M. distortum, M. gypseum or M. fulvum In addition, the invention is useful for controlling protozoan or macroscopic infections by organisms such as Cryptosporidium, Isospora belli, Toxoplasma gondii, Trichomonas vaginalis, Cyclospora species.

Accordingly, an antimicrobial peptide or analog or derivative thereof is useful for treating a condition such as, for example, an infection of the skin and/or an infection of the urogenital tract and/or an infection of the digestive system (e.g., the gut) and/or an infection of the lung, and/or an infection of the sinus. For example, the antimicrobial peptide is useful for the treatment of a condition, such as, for example, rosacea, atopic dermatitis (e.g., eczema), a Candida infection (e.g., vaginal, diaper, intertrigo, balanitis, oral thrush), Tinea versicolor, Dermatophytosis (e.g., Tinea pedis (athlete's foot), Tinea unguium, Onychomycosis (e.g., toe nail fungus), Tinea cruris, Tinea capitus, Tinea corporis, Tinea barbae, seborrheic dermatitis, antibiotic-resistant skin infections, impetigo, ecthyma, erythrasma, burn wounds (e.g., reduction of infections, improved healing), diabetic foot/leg ulcers (e.g., reduction of infections, improved healing), prevention of central catheter-related blood stream infections, oral mucositis, warts (e.g., common, flat, plantar, genital), and molluscum contagiosum. In some embodiments, the condition is acne, often acne vulgaris and sometimes acne conglobate.

The peptides, analogs and/or derivatives of the present invention are also useful for treating a medical condition or a microorganism-causing complication of a medical condition, such as, for example, pneumonia, sepsis or a microbial complication of cystic fibrosis.

Alternatively, or in addition, an antimicrobial peptide of the invention is useful for treating or preventing an infection in a plant, such as, for example, an infection caused by *Alternaria* spp.; *Armillaria mellae*; *Arthrobotrys oligosporus*; *Boletus granulatus*; *Botrytis fabae*; *Botritis cinerea*; *Candida albicans*; *Claviceps purpurea*; *Cronartium ribicola*; *Epicoccum purpurescens*; *Epidermophyton floccosum*; *Fomes annosus*; *Fusarium oxysporum*; *Gaeumannomyces graminis* var. *tritici*; *Glomerella cingulata*; *Gymnosporangium juniperi-virginianae*; *Microsporum canis*; *Monilinia fructicola*; *Physoderma alfalfae*; *Phytopthera infestans*; *Pityrosporum orbiculare* (*Malassezia furfur*); *Polyporus sulphureus*; *Puccinia* spp.; *Saccharomyces cerevisiae*; *Septoria apiicola*; *Trichophyton rubrum*; *T. mentagrophytes*; *Ustilago* spp.; *Venturia inaequalis*; or *Verticillium dahliae*.

Methods of Administration or Application

There are numerous application for the present invention, such as treatment of a water sample, a food product or an animal feed. For example, a peptide of the present invention is readily administered to a water supply, a food product, an animal feed or crops, simply by adding the peptide to the water supply, food product, animal feed or crops. As discussed herein, the peptide may be added to a water supply, a food product, animal feed or with a suitable carrier in e.g., a solid, liquid, gel, foam or aerosol form.

In the case of administration to an animal or a human, numerous methods of administering an effective amount of an isolated peptide of the present invention or an analog or derivative thereof are available for use by the skilled artisan. Such isolated peptides may be introduced topically (e.g., in the form of a cream or a spray or a powder), parenterally, transmucosally, e.g., orally, nasally, or rectally, or transdermally, intra-arteriolely, intramuscularly, intradermally, subcutaneously, intraperitoneally, intraventricularly, and intracranially. Such administration can also occur via bolus administration. Oral solid dosage forms are described generally in Remington's Pharmaceutical Sciences, 18th Ed.1990 (Mack Publishing Co. Easton Pa. 18042) at Chapter 89, and; Marshall, K. In: Modern Pharmaceutics Edited by G. S. Banker and C. T. Rhodes Chapter 10, 1979, both incorporated herein by reference. A method and composition for pulmonary delivery of drugs for systemic effect is described in U.S. Pat. No. 5,451,569, issued Sep. 19, 1995 to Wong et al. (incorporated herein by reference). Systems of aerosol delivery, such as the pressurized metered dose inhaler and the dry powder inhaler are disclosed in Newman, S. P., Aerosols and the Lung, Clarke, S. W. and Davia, D. editors, pp. 197-22 and can be used in connection with the present invention.

In another embodiment, an isolated peptide of the present invention, or variant thereof, can be delivered in a vesicle, in particular a liposome (see Langer, Science 249:1527-1533 (1990); Treat et al., in Liposomes in the Therapy of infectious Disease and Cancer, In the case of administration to a plant, the peptide of the invention is, for example, sprayed onto a plant or plant part or soil comprising a plant or in which a plant is to be grown. Alternatively, the peptide is a component of a fertilizer to be administered to a plant. Alternatively, the peptide is administered in the form of a powder.

Suitable methods of administration and/or application in other situations will be apparent to the skilled artisan. For example, to apply a peptide, analog or derivative of the invention to a food product or a fluid, the peptide, analog or derivative may be sprayed onto or into said food product or fluid or applied to a container in which the food product or fluid is stored.

Pharmacolokinetic Factors Affecting Efficacy of Antimicrobial Peptides

Notwithstanding the relatively broad spectra of the antimicrobial peptides described herein, especially against gram-negative bacteria, their in vitro antimicrobial activities, expressed as minimum inhibitory concentration (MIC) or the minimum bactericidal concentration (MBC), are important considerations when selecting a peptide for a particular treatment context. This is because efficacy of a peptide for any particular treatment context requires a good affinity of the peptide to specific binding sites in the bacteria at a critical concentration and for a sufficient period of time. The pharmacokinetic properties of the peptides can determine a critical concentration at the site of infection as well as the duration of in-vivo exposure. Other factors, e.g., in-vivo disposition of the drug may affect the peptide-bacteria interaction in a clinical setting. The integration of these pharmacokinetic characteristics and the microbiologic activity of an antimicrobial peptide define the pharmacodynamic parameters that form the basis for the optimal method of administration and will enhance its clinical efficacy.

Kinetics of bacterial killing are a function of the period of time required for efficacy and the MIC of the antimicrobial peptide. Accordingly, it is preferred to administer an antimicrobial peptide of the present invention for a minimum period of time of 6-12 hours and/or at a concentration in target tissue (e.g., skin, serum, etc) of at least about 4 times the MIC of the bacteria, preferably at least about 5 times the MIC of the bacteria or at least about 10 times the MIC of the bacteria. The time between doses may also affect efficacy of treatment, and it is preferred to administer the peptides such that serum peptide levels exceed MIC by at least about 4 times during at least 60-70% of the dose interval, achievable e.g., by daily or more frequent dosing, by dosing at higher concentration and at longer time intervals or by continuous infusion following a bolus dose to obviate any observed lag period required to reach a steady state by constant infusion.

Post-antibiotic effect (PAE) of the peptide i.e., the time period after an exposure to and removal of an antimicrobial peptide during which inhibition of bacterial growth persists, may also vary for different peptide-microbe interactions. This may, to a certain extent, be dependent upon the concentration of the peptide administered and/or the duration of exposure to the peptide and/or the antimicrobial combination being administered. Other factors, such as post-antibiotic leukocyte enhancing effect (PALE) and the sub-minimum inhibitory concentration effect, may prolong PAE in vivo. During a PAE, lower concentrations of the antimicrobial peptide may be administered because, microorganisms that undergo a PAE may be highly sensitive to even sub-minimal inhibitory concentrations of antimicrobial peptide(s) of the present invention when administered subsequent to an initial dose of peptide or subsequent to an initial dose of a conventional antibiotic. Because not all known antimicrobial drugs exert a PAE against gram-negative bacilli, the antimicrobial peptides of the present invention, which have relatively low MIC for gram negative bacteria may be particularly useful for that specific treatment context.

The maximum or peak serum level (Cmax or Peak) integrated with the MIC or MBC may define the time exposure threshold of an antimicrobial peptide. These parameters are expressed as the ratio of peak or maximal serum concentration to MIC (Cmax/MIC), the ratio of the area under the concentration time curve (AUC) to the MIC (AUIC), and the time in which serum levels exceed the MIC (time>MIC). These parameters are studied to determine which correlate best with antimicrobial efficacy for different antimicrobial peptides. Preferred determinants of successful outcome are selected from the group consisting of peak plasma level (e.g., as determined by stepwise logistic regression taking into account significant pharmacokinetic, clinical and microbial factors), mean geometric MIC, maximal peak, mean peak/MIC, and maximal peak/MIC. Preferred Cmax target of 10×MIC should provide at least about 90% efficacy, combined with maintenance of maximal serum level of an antimicrobial peptide to prevent the emergence of resistant mutants. Lower Cmax/MIC ratios, especially less than about 2-3 may, in some circumstances, permit the emergence of mutants having diminished sensitivity to the peptide.

Preferably, these parameters are not inconsistent with an effective peptide concentration in the target tissue in the microgram range, preferably about 10-100 µg/ml. Such dosage concentrations generally lend themselves to formulations comprising the antimicrobial peptide at relatively low concentration, preferably less than about 1-10 mg/ml, and more preferably at sub-milligram concentration, even assuming high turnover of 99% in the first 12 hours following administration. The preferential use of analogs described herein, especially retroinverted analogs of antimicrobial peptides also achieve higher serum levels between doses by virtue of their having longer half-lives compared to their unmodified counterparts.

In Vivo Efficacy of Antimicrobial Peptides

The efficacy in vivo of an antibacterial peptide of the present invention is confirmed by any one of a number of methods known to those skilled in the art.

In one preferred example, a murine model of infection is employed, such as the murine model of infection by *Pseudomonas aeruginosa* described, e.g., by Tang et al.,

*Infection and Immunity*, 1278-1285 (1995). This infant mouse model of *P. aeruginosa* pneumonia allows for the in vivo evaluation of bacterial and host factors important in the acute stages of pulmonary infection. The use of this model also provides a means to test preventative and therapeutic strategies against the acquisition of these organisms. The basic procedure is readily amenable to determining pharmokinetic data referred to in the preceding paragraphs.

Briefly, in the infant mouse model of *P. aeruginosa* infection, guaranteed-pregnant and infection-free BALB/cByJ mice (e.g., Jackson Laboratories, Bar Harbor, Me.) are maintained until litter drop, and the litter of 7-day-old mice is inoculated with bacterium capable of infecting mice e.g., a single strain of *P. aeruginosa* in the presence or absence of antimicrobial peptide. Peptide is administered intravenously, or orally e.g., in food or water. Alternatively, the antimicrobial peptide is administered post-infection. The mice are returned to the mother following the inoculation and sacrificed about 24 hr post-inoculation, and the right lung and spleen tissue weighed, homogenized in sterile PBS to a smooth consistency and cultured on MacConkey-lactose agar plates. The left lung and selected spleens are placed in 10% buffered formalin for histopathological studies. Animals found dead at 24 h are also treated in a similar manner. Evidence of bacterial infection and symptoms of phenumonia in the cadavers are assessed. Cultures indicate the extent to which the antimicrobial peptide actually kills the bacterium as opposed to merely preventing growth.

Stimulation of an Immune Response

The antimicrobial peptides, analogs and/or derivatives of the present invention are also useful for simulating a non-specific immune response or an innate immune response of a subject. For example, the antimicrobial peptide is administered to a subject in need thereof for a time and under conditions sufficient to induce the innate immune response of said subject. As the innate immune system is generally activated in response to an infection and/or a cancer, a subject in need of treatment is, for example, a subject at risk of developing an infection e.g., a subject exposed to an infectious agent) and/or a subject at risk of developing a cancer.

Accordingly, the present invention additionally provides a method of therapeutic or prophylactic treatment of a subject suffering from or at risk of developing an infection or a cancer, said method comprising administering an antimicrobial peptide of the invention or an analog or derivative thereof for a time and under conditions sufficient to induce or enhance the innate immune response of the subject.

Suitable peptides, compositions and methods of administration are described herein and are to be taken to apply mutatis mutandis to the present embodiment of the invention.

For example, the antimicrobial peptide of the invention or an analog or derivative thereof is administered to a subject for a time and under conditions sufficient to enhance the production and/or activation of a macrophage and/or a natural killer cell (NK cell) and/or a neutrophil. Methods for detecting, for example, NK cell activation are known in the art and include, for example, a Boyden chamber assay as described by Axelsson et al., *J. Immunol. Methods* 46: 251-258, 1981.

Alternatively, or in addition, the antimicrobial peptide of the invention or an analog or derivative thereof is administered to a subject for a time and under conditions sufficient to enhance the level of a complement pathway protein or to enhance complement pathway activation. Methods for determining complement pathway activation will be apparent to the skilled artisan and include, for example, total hemolytic complement assay (CH50), which measures the ability of the classical pathway and the membrane attack complex to lyse a sheep red blood cells to which an antibody has been attached. The level of various complement proteins may also be measured using antigenic techniques known in the art (e.g., nephelometry, agar gel diffusion, radial immunodiffusion).

The innate immune response also stimulates the adaptive immune response, e.g., T cell production and/or B cell production and/or antibody production. For example, the innate immune response stimulates the production and/or activation of a dendritic cell, which in turn presents an antigen to a T cell and/or a B cell, thereby enhancing the adaptive immune response. Accordingly, the present invention also provides a method for enhancing the immune response of a subject to an antigen, said method comprising administering to said subject an antimicrobial peptide of the invention or an analog or derivative thereof and an antigen for a time and under conditions sufficient for the subject to raise an immune response against said antigen.

In accordance with the present embodiment of the invention, the antimicrobial peptide of the invention or analog or derivative thereof is administered with the antigen, e.g., in the same composition as the antigen and/or conjugated to the antigen. Alternatively, the antimicrobial peptide of the invention or analog or derivative thereof is administered separately to the antigen, e.g., the antimicrobial peptide is administered intranasally and the antigen administered intravenously.

Suitable antigens will be apparent to the skilled artisan. For example, the antigen is from a microorganism. Accordingly, the antimicrobial peptide acts directly on the microorganism and stimulates an immune response against the microorganism. For example, the antigen is a clfA protein from *S. aureus* (SEQ ID NO: 52) or a PcrV antigen of *P. aeruginosa* (SEQ ID NO: 53) or a Int1p protein of *C. albicans* (SEQ ID NO: 54).

The present invention is described further in the following non-limiting examples:

EXAMPLE 1

Antimicrobial Activity of Peptides

Synthetic Peptides

Three amidated peptides were commercially synthesized by Auspep. The sequences of the peptides are as follows:

```
                                        (SEQ ID NO: 2)
KRGFGKKLRKRLKKFRNSIKKRLKNFNVVIPIPLP-NH2;

(SEQ ID NO: 19)
KRGLWESLRKATKLGDDIRNTLRNFKIKFPVPRQ-NH2;
and (SEQ ID NO: 31)
RKKGSKRHKPGSYSVIALGKPGVKKSPYMEAL-NH2.
```

Antimicrobial Assays

Peptides were tested for antimicrobial activity against *Escherichia coli* DH5α, *Escherichia coli* DH5α comprising an ampicillin resistant gene, *Pseudomonas* spp., *Pseudomonas vulgaris*, *Proteus vulgaris*, *Pseudomonas aeruginosa* (ATCC 27853), *Salmonella choleraesuis* (ATCC 14028), *Bacillus subtilis*, *Staphylococcus aureus* (ATCC 25923), *Streptococcus pyogenes* (ATCC 19615), *Streptococcus Agalactiae* (ATCC 12927), *Streptococcus equi equi* (β-Haemolytic streptococcus) (ATCC 9527), and the yeast *Candida albicans* (ATCC753), by a two stage radial diffusion assay essentially as described in Steinberg and Lehrer, *Methods Mol. Biol.*, 78: 169-88, 1997. Briefly, approximately $4 \times 10^6$ of mid-logarithmic-phase organisms were grown on plates in 11 ml of warm 0.8% agarose containing 0.03% (w/v)

Tryticase soy broth (TSB) powder, with or without 100 mM NaCl, buffered with 10 mM sodium phosphate, pH 7.4. The test peptide was serially diluted in acidified water (0.01% acetic acid), and 5 µl of diluted peptide sample was loaded in a 2.5 diameter well in the agarose. A 10 ml overlay gel composed of 6% TSB, 0.8% agarose and 10 mM sodium phosphate buffer (pH 7.4) was poured into each well. Plates were then incubated overnight to allow the surviving organisms to form microcolonies. The clear zone were measured to the nearest 0.1 mm using a magnified transilluminator and expressed in units (1 mm=10 U) after subtracting the well diameter. The minimum inhibitory concentration (MIC) is defined by the $\chi$ intercept of a regression line through zone diameters obtained from a series of serially diluted peptide samples.

Results

Table 1 shows the minimum inhibitory concentration (MIC) of each of the antimicrobial peptides set forth in SEQ ID Nos: 2, 19 and 31 required to inhibit a range of gram-negative bacteria, gram positive bacteria and a fungus. Data in Table 1 are presented as means±standard error of the mean (SEM) from two experiments. Partial inhibition without obvious definition of a clear zone is indicated by asterisks (**). The MICs obtained for a peptide comprising an amino acid sequence set forth in SEQ ID Nos: 2 and 19 in low salt are also represented graphically in FIGS. 1*a* and 1*b*.

activity against gram-negative bacteria as a class, and more specifically provided stronger protection against *E. coli*, *Pseudomonas* spp. including *P. aeruginosa*, *Proteus vulgaris* and *Salmonella choleraesuis*. However, data presented in Table 1 clearly indicate stronger antimicrobial activity of SEQ ID NO: 2 (i.e., MIC less than about 2.5 µg/ml) against *E. coli*, *Pseudomonas* spp. including *P. aeruginosa* and *Proteus vulgaris*. So far as gram-positives are concerned, SEQ ID NO: 2 also exhibited strong (i.e., MIC less than about 2.5 µg/ml) antimicrobial activity against *Bacillus subtilis*, *Streptococcus pyogenes*, and *Streptococcus equi equi*, and moderate antimicrobial activity against *Streptococcus agalactiae*, and weaker antimicrobial activity against *Staphylococcus aureus*. Weaker antimicrobial activity of SEQ ID NO: 2 was also observed against *Candida albicans*.

SEQ ID NO: 19 appears to have weaker antimicrobial activity than SEQ ID NO: 2 against the panel of isolates tested, with the exception of *S. agalactiae* and *S. pyogenes*, against which SEQ ID NO: 19 may the preferred peptide based on MIC value. Additionally, SEQ ID NO: 19 was weaker than SEQ ID NO: 2 (i.e., MIC>5.0 µg/ml) against the gram-negative bacteria tested. These factors suggest a combination therapy of SEQ ID NO: 2 and SEQ ID NO: 19 for certain indications where broad spectrum activity is desired, and specific regimens involving SEQ ID NO: 19 for treatment of *S. agalactiae* and/or *S. pyogenes* infection(s). SEQ ID NO:

TABLE 1

| | MIC (µg/ml) in media containing 0 mM NaCl or 100 mM NaCl | | | | | |
|---|---|---|---|---|---|---|
| | SEQ ID NO: 2 | | SEQ ID NO: 19 | | SEQ ID NO: 31 | |
| Microorganism | 0 mM | 100 mM | 0 mM | 100 mM | 0 mM | 100 mM |
| Gram-negative bacteria | | | | | | |
| *E. coli* DH5α | 1.75 ± 0.22 | 1.32 ± 0.35 | 19.97 ± 0.41 | 26.10 ± 0.41 | 1.16 ± 0.67 | |
| *Pseudomonas* spp | 1.80 ± 0.30 | 1.83 ± 0.23 | 15.94 ± 0.29 | 22.12 ± 0.43 | | |
| *P. aeruginosa* (ATCC 28753) | 2.28 ± 0.53 | 1.51 ± 0.51 | 9.19 ± 0.41 | 10.45 ± 0.24 | 57.8 | |
| *Salmonella choleraesuis* (ATCC 14028) | 3.46 ± 0.66 | 2.05 ± 0.62 | 9.32 ± 0.38 | ** | >250 | |
| *Proteus vulgaris* | 1.64 ± 0.32 | 1.73 ± 0.23 | 9.82 ± 0.28 | 67.45 ± 0.20 | | |
| Gram-positive bacteria | | | | | | |
| *Bacillus subtilis* | 1.99 ± 0.38 | 13.83 ± 0.45 | 2.74 ± 0.48 | 8.67 ± 0.39 | 14.03 ± 0.25 | |
| *Staphylococcus aureus* (ATCC 25923) | 5.72 ± 0.37 | ** | 5.44 ± 0.49 | ** | 8.5 ± 0.23 | |
| *Streptococcus pyogenes* (ATCC 19615) | 2.42 ± 0.25 | 3.57 ± 0.41 | 1.19 ± 0.37 | 8.24 ± 0.37 | 3.43 ± 0.34 | |
| *Streptococcus equi equi* (ATCC 9527) | 2.39 ± 0.35 | 4.05 ± 0.39 | 4.85 ± 0.35 | ** | 8.66 ± 0.45 | |
| *Streptococcus agalactiae* (ATCC 12927) | 3.81 | | 1.2 | | 5.44 ± 0.11 | |
| Fungus | | | | | | |
| *Candida albicans* (ATCC 753) | 5.48 ± 0.16 | ** | 10.01 ± 0.47 | | >250 | |

Figure 1B:
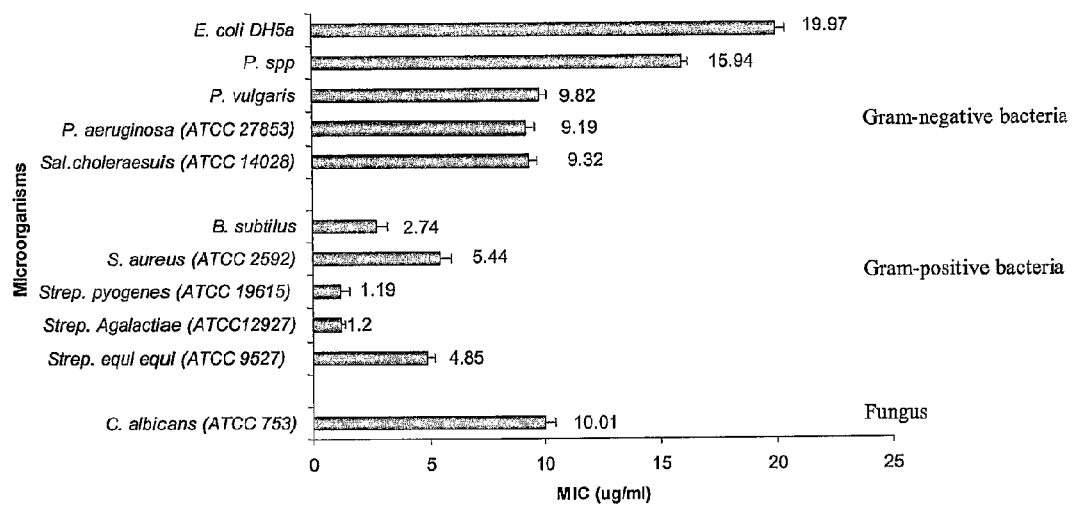
FIG. 1b is a graphical representation of the minimum inhibitory concentration (MIC) of an antimicrobial peptide comprising an amino acid sequence set forth in SEQ ID NO: 19 as determined using a radial diffusion assay. The MIC (μg/ml) is indicated on the X-axis. The MIC is defined as the χ intercept of the least mean square regression lines through the respective data points. Results are means±standard error of the mean (SEM) from two experiments. The microorganism being tested is indicated on the Y axis.

The data presented in Table 1 and FIGS. 1*a* and 1*b* indicate a broad spectrum of activity for the identified antimicrobial peptides, in low and high salt concentrations. The maintenance of antimicrobial activity in high salt suggests efficacy in body fluids, such as, for example, blood.

SEQ ID NO: 2 appears active against all microorganisms tested at less than 10 µg/ml, these low MIC values suggesting that the base peptide and analogs and derivatives thereof having enhanced activity and/or half-life, are particularly strong candidates for development into therapeutic formulations. In particular, SEQ ID NO: 2 exhibited consistent moderate-strong (i.e., MIC less than about 5 µg/ml) antimicrobial 19 was also moderately protective against *B. subtilis* and *S. equi equi*. Weaker antimicrobial activity of SEQ ID NO: 19 was also observed against *Candida albicans*.

SEQ ID NO: 31 also exhibited a broad spectrum of antimicrobial activities, but was generally weaker than SEQ ID NO: 2 and SEQ ID NO: 19. However, this peptide did exhibit strong protection against *E. coli*, comparable to SEQ ID NO: 2; and moderate protection against *S. pyogenes*. This activity profile suggests that SEQ ID NO: 31 may, in some case, supplement SEQ ID NO: 19 for specific treatment of specific infections that include *E. coli*.

EXAMPLE 2

Antimicrobial Peptides Have Low Toxicity to Mammalian Cells

Methods

The toxicity of the antimicrobial peptides was determined using a haemolytic assay. In particular, the hemolytic activity of the peptides was determined using tammar wallaby erythrocytes. Fresh erythrocytes were harvested from heparinized blood taken from a tammar wallaby. Erythrocytes were harvested by centrifugation for 3 min at 3000 g. Erythrocytes were then washed three times with PBS (pH 7.4) until the supernatant was essentially colourless. 20 µl two fold serial dilutions of the peptide were mixed with the same volume of erythrocytes in solution 2%) in PBS of each well of a 96-plate. 80 µl PBS was added to each well after the plate was incubated at 37° C. for one hour. Plates were then centrifuged at 3000 g for 5 min. 90 µl of the resulting supernatant was transferred to a flat-bottom microtiter plate and haemoglobin release was monitored by measuring the absorbance at 414 nm with an ELISA plate reader. Total hemolysis was achieved with 1% Tween-20 and control (zero percent) hemolysis were determined in PBS, respectively. Each sample was performed in triplicate. Percentage hemolysis was calculated by the following formula: [(OD414 peptide−OD414 buffer)/OD414 complete hemolysis−OD414 buffer)]×100%.

Results

Figure 2A:
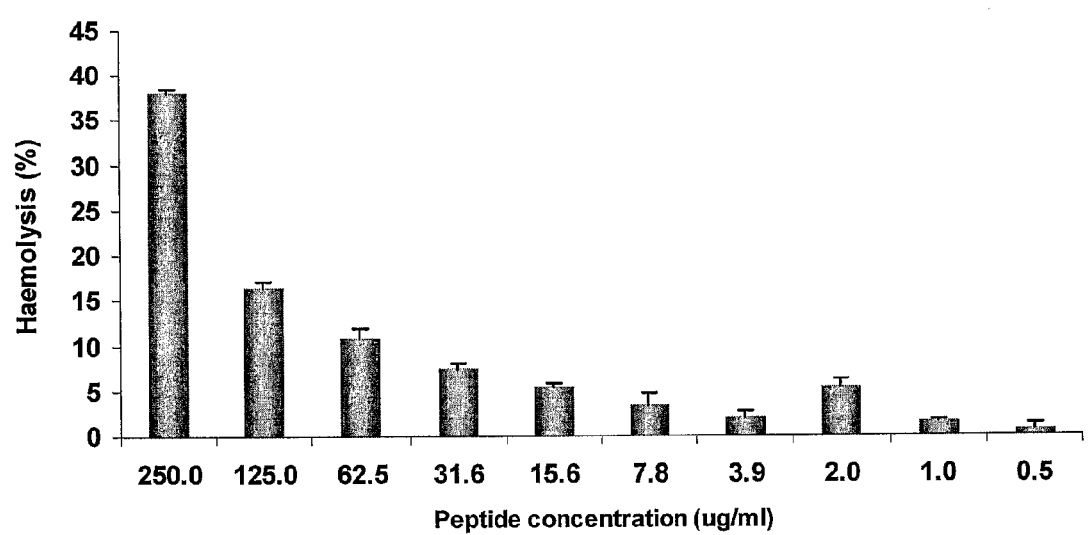
FIG. 2a is a graphical representation showing the percentage haemolysis of red blood cells at various concentrations of an antimicrobial peptide comprising an amino acid sequence set forth in SEQ ID NO: 2. Results are presented as percentage of total haemolysis, obtained by adding 1% Tween-20 to an erythrocyte cell suspension. The concentration of the peptide (μg/ml) is indicated on the X-axis. The percentage haemolysis is indicated on the Y axis. Results are means of triplicate assays±SEM.
Figure 2B:
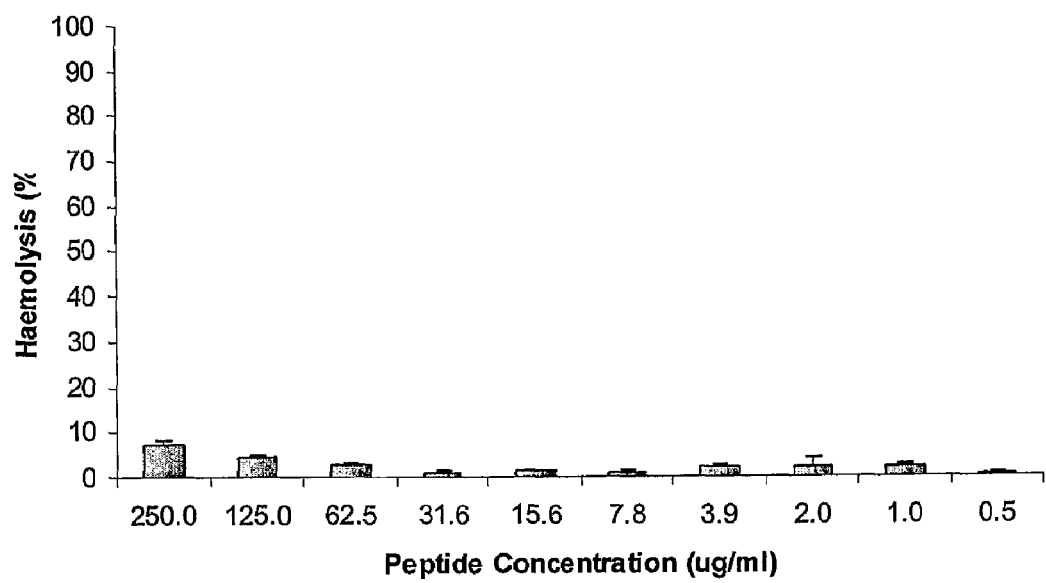
FIG. 2b is a graphical representation showing the percentage haemolysis of red blood cells at various concentrations of an antimicrobial peptide comprising an amino acid sequence set forth in SEQ ID NO: 19. Results are presented as percentage of total haemolysis, obtained by adding 1% Tween-20 to an erythrocyte cell suspension. The concentration of the peptide (μg/ml) is indicated on the X-axis. The percentage haemolysis is indicated on the Y axis. Results are means of triplicate assays±SEM.

As shown in FIGS. 2a and 2b, a peptide comprising an amino acid sequence set forth in SEQ ID NO: 2 or SEQ ID NO: 19, respectively, did not cause substantial levels of haemolysis at the majority of concentrations tested. In fact at the MIC determined in Example 1, these peptides caused less than about 5% haemolysis. Accordingly, the antimicrobial peptides show low levels of toxicity to mammalian cells, indicating their utility for use in mammals, e.g., for the treatment of infections.

EXAMPLE 3

Efficacy of Antimicrobial Peptides against Multidrug-Resistant Bacterial Isolates Methods The MIC values of SEQ ID NO: 2 and SEQ ID NO: 19 were also determined against a range of multidrug-resistant isolates, including clinical and laboratory strains. Peptides, maintained at −20° C. in solid form for storage purposes, were subsequently dissolved in 0.01% (v/v) acetic acid (Sigma-Aldrich) to a stock concentration of 0.64 mg/L. The stock solutions were made fresh for each experiment. Eighteen (18) bacterial isolates obtained from the Facility for Anti-Infective Drug Development and Innovation, Victoria, Australia (FADDI) as listed in Table 2 were maintained as stock cultures in Tryptic Soya Broth plus 20% (v/v) glycerol at a temperature of −80° C., and subcultured onto Nutrient Agar for each experiment. MIC values were determined in cation-adjusted Mueller-Hinton broth (CAMHB) and Mueller-Hinton broth (MHB) using standard broth micro-dilution methods. Experiments were conducted for 17 hr incubation at 35° C., after which time MIC values were determined.

TABLE 2

| Isolate number | Isolate description | Source | Colistin resistant (R) or susceptible (S) |
|---|---|---|---|
| 1 | Pseudomonas aeruginosa (ATCC 27853) | Reference isolate | S |
| 2 | P. aeruginosa strain FADDI 001 | Clinical specimen | S |
| 3 | P. aeruginosa strain FADDI 002 | Clinical specimen | S |
| 4 | P. aeruginosa strain FADDI 003 | Clinical specimen | R |
| 5 | P. aeruginosa strain FADDI 004 | Clinical specimen | R |
| 6 | Acinetobacter baumannii (ATCC 19606) | Reference isolate | S |
| 7 | A. baumannii strain FADDI 005 (ATCC 19606 derivative) | Laboratory prepared | R |
| 8 | A. baumannii strain FADDI 006 | Clinical specimen | R |
| 9 | A. baumannii strain FADDI 007 | Clinical specimen | S |
| 10 | Klebsiella pneumoniae (ATCC 13883) | Reference isolate | S |
| 11 | K. pneumoniae strain FADDI 008 | Clinical specimen | S |
| 12 | K. pneumoniae strain FADDI 009 | Clinical specimen | R |
| 13 | K. pneumoniae strain FADDI 010 | Clinical specimen | R |
| 14 | Staphylococcus aureus (ATCC 700698) | Reference isolate, h-VISA | — |
| 15 | S. aureus 700699 | Reference isolate, VISA | — |
| 16 | S. aureus (ATCC 43300) | Reference isolate, MRSA | — |
| 17 | S. aureus strain FADDI 011 | Clinical specimen | — |
| 18 | Enterococcus faecium (ATCC 700221) | Reference isolate, VRE | — |

Pseudomonas aeruginosa (ATCC 27853) and S. aureus (ATCC 43300) were included as quality controls in experiments. P. aeruginosa strains FADDI 001 and FADDI 002 are mucoid; and P. aeruginosa strains FADDI 003 and FADDI 004 are non-mucoid. P. aeruginosa strain FADDI 003 also has a small colony morphology. The A. baumannii strain FADDI 005 is a colistin-resistant isolate obtained from Mueller-Hinton agar containing 10 mg/L colistin.

Results

The MIC values for SEQ ID NO: 2 and SEQ ID NO: 19 against the panel of reference and clinical isolates shown in Table 2 are presented in Table 3.

TABLE 3

MIC (μg/ml) of antimicrobial peptides against
a panel of reference and clinical isolates

| Isolate description | SEQ ID NO: 2 | | SEQ ID NO: 19 | |
|---|---|---|---|---|
| | CAMHB[a] | MHB[b] | CAMHB[a] | MHB[b] |
| *Pseudomonas aeruginosa* (ATCC 27853) | 16 | 4 | >64 | 32 |
| *P. aeruginosa* strain FADDI 001 | 16 | 8 | >64 | >64 |
| *P. aeruginosa* strain FADDI 002 | 4 | 4 | >64 | >64 |
| *P. aeruginosa* strain FADDI 003 | 8 | 2 | >64 | >64 |
| *P. aeruginosa* strain FADDI 004 | 32 | 8 | >64 | >64 |
| *Acinetobacter baumannii* (ATCC 19606) | 4 | 8 | 32 | 16 |
| *A. baumannii* strain FADDI 005 (ATCC 19606 derivative) | 8 | 4 | 8 | 16 |
| *A. baumannii* strain FADDI 006 | >64 | >64 | >64 | >64 |
| *A. baumannii* strain FADDI 007 | 8 | 8 | 16 | 16 |
| *Klebsiella pneumoniae* (ATCC 13883) | 1 | 2 | >64 | 16 |
| *K. pneumoniae* strain FADDI 008 | 16 | 8 | >64 | >64 |
| *K. pneumoniae* strain FADDI 009 | 4 | 4 | >64 | >64 |
| *K. pneumoniae* strain FADDI 010 | 32 | 32 | >64 | >64 |
| *Staphylococcus aureus* (ATCC 700698) | >64 | >64 | >64 | >64 |
| *S. aureus* 700699 | >64 | >64 | >64 | >64 |
| *S. aureus* (ATCC 43300) | >64 | >64 | >64 | >64 |
| *S. aureus* strain FADDI 011 | >64 | >64 | >64 | >64 |
| *Enterococcus faecium* (ATCC 700221) | 16 | 16 | 16 | 16 |

[a]CAMHB comprises 10.0 mg/L $Mg^{2+}$ and 24 mg/L $Ca^{2+}$
[b]MHB comprises less than 5 mg/L $Mg^{2+}$ and 24 mg/L $Ca^{2+}$ Data presented in Table 2 and Table 3 clearly demonstrate no correlation between colistin-resistance profile and antimicrobial spectrum of any antimicrobial peptide of the present invention, suggesting an entirely different mode of action of the antimicrobial peptide(s) compared to the antibiotic colistin.

Data presented in Table 3 also confirm the broad spectrum of antimicrobial activity for both SEQ ID NO: 2 and SEQ ID NO: 19 obtained in Example 1, and also confirm the observation that SEQ ID NO: 2 is stronger against *P. aeruginosa* than SEQ ID NO: 19. The data presented in Table 3 also confirm the relatively weaker activities of both peptides against *S. aureus* compared to other bacteria.

Data presented in Table 3 also support the observation (Example 1) that SEQ ID NO: 2 has general activity against gram-negative bacteria, in view of the moderate-strong antimicrobial activity of the peptide against all reference and clinical isolates tested of the genera *Pseudomonas*, *Acinetobacter* and *Klebsiella*, in both high and low salt-containing media. As with the data presented in Table 1, these data support the conclusion that SEQ ID NO: 2 and analogs and derivatives thereof are strong candidate antimicrobial peptides.

Data presented in Table 3 supplement the data in Table 1 by showing that SEQ ID NO: 2 and SEQ ID NO: 19 are equally effective against *Enterococcus faecium*. This information supports the earlier observation that SEQ ID NO: 19 or SEQ ID NO: 31 may be suited for use in combination with SEQ ID NO: 2, and suggest further that SEQ ID NO: 2 or SEQ ID NO: 19 may be suited for specific treatment of enterococcal infection, especially treatment of *E. faecium*.

The activities of the antimicrobial peptides of the present invention against a wide range of reference and clinical isolates of gram-negative and gram-positive bacteria as demonstrated herein suggests their utility in a wide range of treatment contexts, including the treatment of infections by multidrug-resistant bacteria.

EXAMPLE 4

Antimicrobial Peptide SEQ ID NO: 2 Has Stronger Activity against *Escherichia Coli* than LL-37

The antibacterial peptide is the "gold standard" in the art. The LL-37 peptide comprises amino acid residues 104-140 of the 18-kDa human cationic antimicrobial protein (hCAP18) described e.g., by Larrick et al., *Infect. Immun.* 63, 1291-1297 (1995); Cowland et al., *FEBS Lett.* 368, 173-176 (1995) and Lehrer and Ganz, *Curr. Opin. Immunol.* 11, 23-27 (1999). It has been shown to have broad spectrum activity against a wide number of microorganisms, and to induce innate immunity.

Methods

To determine whether or not the antimicrobial peptides of the present invention provide an advantage over LL-37, the MIC of the peptides disclosed herein are compared to the MIC of LL-37 under identical conditions. In one example, the MIC of antimicrobial peptide of SEQ ID NO: 2 against an *Escherichia coli* isolate was compared to the MIC of LL-37 against the same bacterial isolate, as determined by radial diffusion assay performed as described herein above e.g., Example 1. In another example, the MIC of antimicrobial peptide of SEQ ID NO: 19 against an *Escherichia coli* isolate was compared to the MIC of LL-37 against the same bacterial isolate.

Microbroth dilution assay in MHB were also performed as described in the preceding example, to confirm radial diffusion assay results.

Results

Figure 3:
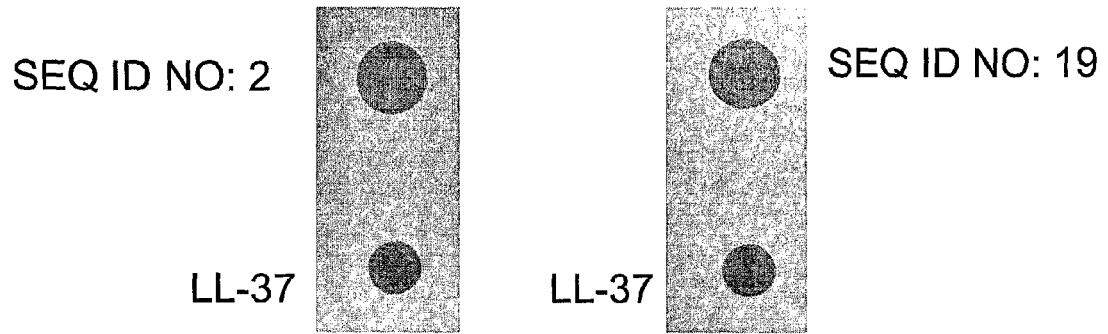
FIG. 3 is a photographic representation showing that the antimicrobial peptides of SEQ ID Nos: 2 and 19 are more potent than LL-37 against *E. coli* in a radial diffusion assay. Briefly, 5 μl of 250 μg/ml solutions of each peptide were subjected to radial diffusion assay as described in the examples. The larger cleared area for samples having SEQ ID Nos: 2 and 19 compared to LL-37 demonstrate higher potency of these peptides relative to LL-37 in this assay.

Data presented in FIG. 3 demonstrate a larger radial clear zone on plates containing *E. coli* in the presence of SEQ ID NO: 2 or SEQ ID NO: 19 compared to LL-37. Based on the approximately identical sizes of SEQ ID NO: 2, SEQ ID NO: 19 and LL-37, it is very likely that the differences are not due to differential diffusion per se of the peptides through the gel. Accordingly, these data indicate that SEQ ID NO: 2 and SEQ ID NO: 19 have stronger antimicrobial activities than LL-37 against *E. coli*, and suggest that SEQ ID NO: 2 and SEQ ID NO: 19 may be preferred for treatment of *E. coli* infection e.g., in the treatment of mastitis. These data also suggest that the antimicrobial peptides of the present invention (especially SEQ ID NO: 2) and analogs and derivatives thereof, are likely to provide significant advantages over LL-37 in other treatment protocols. This conclusion is supported by microbroth dilution assay data (Table 4) showing enhanced efficacy of SEQ ID NO: 2 relative to LL-37 against a range of gram-negative bacteria including *E. coli*.

TABLE 4

MIC (µg/ml) of SEQ ID NO: 2 relative to LL-37 against gram-negative bacteria

| Strain | SEQ ID NO: 2 | LL-37 |
|---|---|---|
| *Escherichia coli* DH5 α | 2 | 32 |
| *Pseudomonas aeruginosa* (ATCC 27853) | 4 | >32 |
| *Acinetobacter baumannii* (ATCC 19606) | 4 | 32 |
| *Klebsiella pneumoniae* (ATCC 13883) | 2 | 32 |
| *Staphylococcus aureus* (ATCC 43300) | >64 | >32 |

EXAMPLE 5

Antimicrobial Activities and Stability of Analogs and Derivatives of SEQ ID NO: 2

The clinical efficacy of antimicrobial peptides may be reduced in vivo by the presence of one or more inhibitory factors e.g., salts, bivalent cations, peptide-binding proteins, and their turnover may be enhanced in vivo by proteolysis.

Methods

To determine whether or not it is possible to enhance the efficacy of the antimicrobial peptides set forth in SEQ ID Nos: 2, 19 and 31, modified peptides are produced and tested against the target *Escherichia coli* using a radial diffusion assay performed as described herein above e.g., Example 1. Microbroth dilution assay in MHB were also performed as described in the preceding example, to confirm radial diffusion assay results.

In one example, SEQ ID NO: 2 was modified as follows:

All D-Amino Acid Analog

To produce an "all-D" analog, each amino acid of SEQ ID NO: 2 was modified from an L-amino acid into the corresponding D-amino acid, to produce the following sequence:

(SEQ ID NO: 9)
D-Lys D-Arg D-Gly D-Phe D-Gly D-Lys D-Lys D-Leu D-

Arg D-Lys D-Arg D-Leu D-Lys D-Lys D-Phe D-Arg D-

Asn D-Ser D-Ile D-Lys D-Lys D-Arg D-Leu D-Lys D-

Asn D-Phe D-Asn D-Val D-Val D-Ile D-Pro D-Ile D-

Pro D-Leu D-Pro.

Terminal D-Amino Acid Analog

To produce a "terminal-D" analog, the N-terminal and C-terminal amino acid residues only of SEQ ID NO: 2 were modified from L-amino acids into the corresponding D-amino acids, to produce the following sequence:

(SEQ ID NO: 11)
D-Lys Arg Gly Phe Gly Lys Lys Leu Arg Lys Arg Leu

Lys Lys Phe Arg Asn Ser Ile Lys Lys Arg Leu Lys

Asn Phe Asn Val Val Ile Pro Ile Pro Leu D-Pro.

Retro (Reversed) Derivative

To produce a "retro" derivative of SEQ ID NO: 2, the entire sequence of the base peptide was reversed and synthesized using L-amino acids, to produce the following sequence:

(SEQ ID NO: 13)
Pro Leu Pro Ile Pro Ile Val Val Asn Phe Asn Lys

Leu Arg Lys Lys Ile Ser Asn Arg Phe Lys Lys Leu

Arg Lys Arg Leu Lys Lys Gly Phe Gly Arg Lys.

Retroinverted Analog

To produce a "retroinverted" derivative of SEQ ID NO: 2, the entire sequence of the base peptide was reversed, all but the terminal residues were synthesized using L-amino acids, and the N-terminal and C-terminal amino acids were synthesized using D-amino acids, to produce the following sequence:

(SEQ ID NO: 17)
D-Pro Leu Pro Ile Pro Ile Val Val Asn Phe Asn Lys

Leu Arg Lys Lys Ile Ser Asn Arg Phe Lys Lys Leu

Arg Lys Arg Leu Lys Lys Gly Phe Gly Arg D-Lys.

In a related albeit separate example, the stability of SEQ ID NO: 9 was compared to the stability of SEQ ID NO: 2 in serum over a period of 24 hours, as determined using the radial diffusion assay. This assay was also conducted in the presence of 75% (v/v) goat serum, to determine any negative effects of serum on the antimicrobial activities of the peptides.

Results

Figure 4:
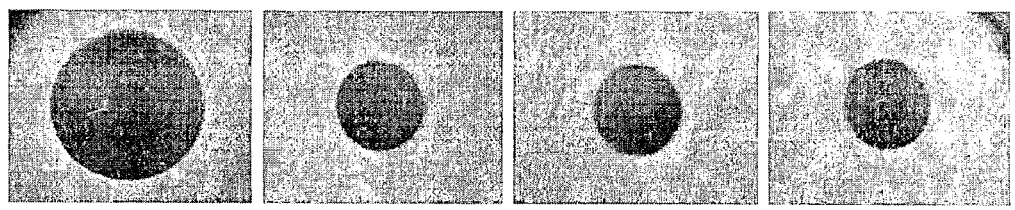
FIG. 4 is a photographic representation showing that analogs and derivatives of the antimicrobial peptide of SEQ ID NO: 2 exhibits antimicrobial activity against *E. coli* in a radial diffusion assay. Briefly, 5 μl of 250 μg/ml solutions of peptides comprising SEQ ID NO: 9, 11, 13 or 17 were subjected to radial diffusion assay as described in the examples. The cleared area for samples having these peptides demonstrates their efficacy in this assay.

For the example described above, the data presented in FIG. 4 indicate significant antibacterial activity of all four modified forms of SEQ ID NO: 2, with strongest antimicrobial activity observed for the all-D analog i.e., SEQ ID NO: 9. This conclusion is supported by microbroth dilution assay data (Table 5) showing efficacy of both SEQ ID NO: 2 and SEQ ID NO: 9 against a range of gram-negative bacteria.

TABLE 5

MIC (µg/ml) of SEQ ID NO: 2 relative to SEQ ID NO: 9 against gram-negative bacteria and *S. aureus*

| Strain | SEQ ID NO: 2 | SEQ ID NO: 9 |
|---|---|---|
| *Escherichia coli* DH5 α | 2 | 4 |
| *Pseudomonas aeruginosa* (ATCC 27853) | 4 | 4 |
| *Acinetobacter baumannii* (ATCC 19606) | 4 | 8 |
| *Klebsiella pneumoniae* (ATCC 13883) | 2 | 4 |
| *Staphylococcus aureus* (ATCC 43300) | >64 | >32 |

Figure 5:
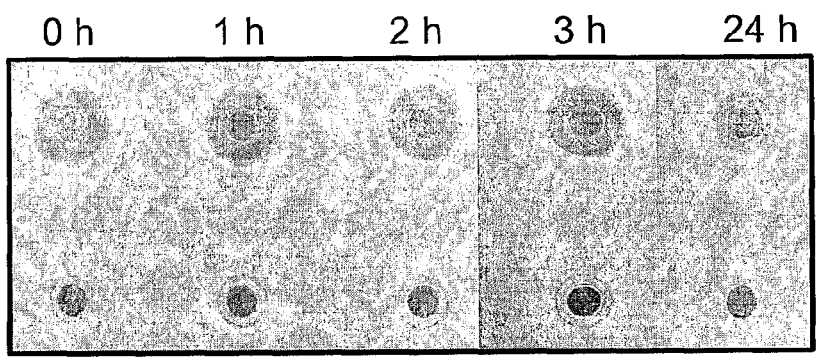
FIG. 5 is a photographic representation showing that the antimicrobial peptide analog of SEQ ID NO: 9 maintains activity against *E. coli* in serum, as determined using a radial diffusion assay. Briefly, 250 μg/ml peptide in presence of 75% goat serum was incubated in 37° C. at indicated time intervals, and 5 μl aliquots of the peptide solutions were subjected to two-layer radial diffusion assay as described in the examples using *E. coli* DH 5α as a target bacterium.

For the examples described above, the data presented in FIG. 5 also indicate that SEQ ID NO: 9 has enhanced activity, at least in serum, relative to SEQ ID NO: 2, and that the peptide maintains its stability in serum for at least the first three hours, with significant activity remaining after 24 hours. In contrast, there was no antibacterial activity remaining for the unmodified form of the peptide, i.e., SEQ ID NO: 2, after 24 hours under these conditions. These data suggest that the introduction of D-amino acids into the antimicrobial peptides of the invention, with or without concomitant reversal of amino acid sequence, enhances their stability and half-life. As with the other data presented herein, these data reinforce the suitability of SEQ ID NO: 2 analogs and derivatives for therapeutic formulations intended for use in vivo, and especially for systemic applications.

Alternatively, each amino acid other than glycine in the sequence of an antimicrobial peptide is modified to a D-amino acid, with equivalent effects.

It is well within the capability of a skilled artisan to apply the examples described herein above to the other analogs and derivatives provided herein, without any undue experimentation.

We claim:

1. An antimicrobial peptide fragment of a tammar wallaby milk protein comprising the sequence as set forth in SEQ ID NO: 2, or an antimicrobial derivative or analog thereof comprising a sequence selected from SEQ ID NO: 9, 11, 13 and 17, wherein SEQ ID NO: 9 has the same amino acid sequence as SEQ ID NO: 2 with substitution of all L-amino acids for all D-amino acids, wherein SEQ ID NO: 11 has the same amino acid sequence as SEQ ID NO: 2 with substitution of N and C terminal L-amino acids for D-amino acids, and wherein said peptide fragment, derivative or analog has enhanced activity against one or a plurality of gram-negative bacteria relative to an equivalent amount of LL-37 peptide comprising amino acid residues 104-140 of the 18-kDa human cationic antimicrobial protein (hCAP18) as determined by minimal inhibitory concentration (MIC) of the peptide, derivative or analog against said one or more gram negative bacteria compared to LL-37.

2. The antimicrobial peptide fragment of a tammar wallaby milk protein or an antimicrobial derivative or analog thereof according to claim 1 having activity against one or more multidrug-resistant bacteria.

3. The antimicrobial peptide fragment of a tammar wallaby milk protein or an antimicrobial derivative or analog thereof according to claim 1 having activity against a plurality of gram-negative bacteria.

4. The antimicrobial peptide fragment of a tammar wallaby milk protein or an antimicrobial derivative or analog thereof according to claim 3 having activity against a bacterium belonging to a genus selected from the group consisting of *Escherichia, Pseudomonas, Proteus, Salmonella, Acinetobacter* and *Klebsiella*.

5. The antimicrobial peptide fragment of a tammar wallaby milk protein or an antimicrobial derivative or analog thereof according to claim 1 having activity against a plurality of gram-positive bacteria.

6. The antimicrobial peptide fragment of a tammar wallaby milk protein or an antimicrobial derivative or analog thereof according to claim 5 having activity against a bacterium belonging to a genus selected from the group consisting of *Bacillus, Staphylococcus, Enterococcus* and *Streptococcus*.

7. The antimicrobial peptide fragment of a tammar wallaby milk protein or an antimicrobial derivative or analog thereof according to claim 1 having activity against one or more fungi of the genus *Candida*.

8. The antimicrobial peptide fragment of a tammar wallaby milk protein or an antimicrobial derivative or analog thereof according to claim 1 comprising one or more chemical moieties other than amino acids.

9. An antimicrobial peptide fragment of a tammar wallaby milk protein wherein said peptide fragment comprises the amino acid sequence of SEQ ID NO: 2.

10. The antimicrobial peptide fragment of a tammar wallaby milk protein or an antimicrobial derivative or analog thereof according to claim 1 wherein said derivative or analog comprises the amino acid sequence of SEQ ID NO: 9 wherein SEQ ID NO: 9 has the same amino acid sequence as SEQ ID NO: 2 with substitution of all L-amino acids for all D-amino acids.

11. The antimicrobial peptide fragment of a tammar wallaby milk protein or an antimicrobial derivative or analog thereof according to claim 1 wherein said derivative or analog comprises the amino acid sequence of SEQ ID NO: 11 wherein SEQ ID NO: 11 has the same amino acid sequence as SEQ ID NO: 2 with substitution of N and C terminal L-amino acids for D-amino acids.

12. The antimicrobial peptide fragment of a tammar wallaby milk protein or an antimicrobial derivative or analog thereof according to claim 1 wherein said derivative or analog comprises the amino acid sequence of SEQ ID NO: 13.

13. The antimicrobial peptide fragment of a tammar wallaby milk protein or an antimicrobial derivative or analog thereof according to claim 1 wherein said derivative or analog comprises the amino acid sequence of SEQ ID NO: 17.

14. A composition comprising an effective amount of an antimicrobial peptide fragment, derivative or analog according to claim 1 to treat a microbial infection in a mammalian host, wherein said peptide fragment, analog or derivative is in combination with a pharmaceutically acceptable carrier or excipient or diluent.

15. A composition comprising an effective amount of an antimicrobial peptide fragment, derivative or analog according to claim 1 to induce, enhance or stimulate an immune response by a subject to an antigen wherein said peptide fragment, analog or derivative is in combination with a pharmaceutically acceptable carrier or excipient or diluent.

16. A solid surface coated with or having adsorbed thereto an antimicrobial peptide fragment, analog or derivative according to claim 1.

17. A medical device coated with or having adsorbed thereto an antimicrobial peptide fragment, analog or derivative thereof according to claim 1.

18. A fusion protein comprising the antimicrobial peptide fragment, derivative or analog thereof according to claim 1.

* * * * *

```
                        SEQUENCE LISTING

<160> NUMBER OF SEQ ID NOS: 54

<210> SEQ ID NO 1
<211> LENGTH: 36
<212> TYPE: PRT
<213> ORGANISM: artificial
<220> FEATURE:
<223> OTHER INFORMATION: antimicrobial peptide derived from Macropus
      eugenii protein

<400> SEQUENCE: 1

Lys Arg Gly Phe Gly Lys Lys Leu Arg Lys Arg Leu Lys Lys Phe Arg
1               5                   10                  15

Asn Ser Ile Lys Lys Arg Leu Lys Asn Phe Asn Val Val Ile Pro Ile
            20                  25                  30

Pro Leu Pro Gly
        35

<210> SEQ ID NO 2
<211> LENGTH: 35
<212> TYPE: PRT
<213> ORGANISM: artificial
<220> FEATURE:
<223> OTHER INFORMATION: antimicrobial peptide fragment of SED ID NO: 1

<400> SEQUENCE: 2

Lys Arg Gly Phe Gly Lys Lys Leu Arg Lys Arg Leu Lys Lys Phe Arg
1               5                   10                  15

Asn Ser Ile Lys Lys Arg Leu Lys Asn Phe Asn Val Val Ile Pro Ile
            20                  25                  30

Pro Leu Pro
        35

<210> SEQ ID NO 3
<211> LENGTH: 27
<212> TYPE: PRT
<213> ORGANISM: artificial
<220> FEATURE:
<223> OTHER INFORMATION: antimicrobial peptide fragment of SED ID NO: 1

<400> SEQUENCE: 3

Lys Arg Gly Phe Gly Lys Lys Leu Arg Lys Arg Leu Lys Lys Phe Arg
1               5                   10                  15

Asn Ser Ile Lys Lys Arg Leu Lys Asn Phe Asn
            20                  25

<210> SEQ ID NO 4
<211> LENGTH: 23
<212> TYPE: PRT
<213> ORGANISM: artificial
<220> FEATURE:
<223> OTHER INFORMATION: antimicrobial peptide fragment of SED ID NO: 1

<400> SEQUENCE: 4

Lys Arg Gly Phe Gly Lys Lys Leu Arg Lys Arg Leu Lys Lys Phe Arg
```

```
                1               5                  10                  15
Asn Ser Ile Lys Lys Arg Leu
            20

<210> SEQ ID NO 5
<211> LENGTH: 25
<212> TYPE: PRT
<213> ORGANISM: artificial
<220> FEATURE:
<223> OTHER INFORMATION: antimicrobial peptide fragment of SED ID NO: 1

<400> SEQUENCE: 5

Gly Phe Gly Lys Lys Leu Arg Lys Arg Leu Lys Lys Phe Arg Asn Ser
1               5                  10                  15

Ile Lys Lys Arg Leu Lys Asn Phe Asn
            20                  25

<210> SEQ ID NO 6
<211> LENGTH: 21
<212> TYPE: PRT
<213> ORGANISM: artificial
<220> FEATURE:
<223> OTHER INFORMATION: antimicrobial peptide fragment of SED ID NO: 1

<400> SEQUENCE: 6

Lys Leu Arg Lys Arg Leu Lys Lys Phe Arg Asn Ser Ile Lys Lys Arg
1               5                  10                  15

Leu Lys Asn Phe Asn
            20

<210> SEQ ID NO 7
<211> LENGTH: 17
<212> TYPE: PRT
<213> ORGANISM: artificial
<220> FEATURE:
<223> OTHER INFORMATION: antimicrobial peptide fragment of SED ID NO: 1

<400> SEQUENCE: 7

Arg Leu Lys Lys Phe Arg Asn Ser Ile Lys Lys Arg Leu Lys Asn Phe
1               5                  10                  15

Asn

<210> SEQ ID NO 8
<211> LENGTH: 36
<212> TYPE: PRT
<213> ORGANISM: artificial
<220> FEATURE:
<223> OTHER INFORMATION: analog of SEQ ID NO: 1 wherein all amino acids
      are D-amino acids

<400> SEQUENCE: 8

Lys Arg Gly Phe Gly Lys Lys Leu Arg Lys Arg Leu Lys Lys Phe Arg
1               5                  10                  15

Asn Ser Ile Lys Lys Arg Leu Lys Asn Phe Asn Val Val Ile Pro Ile
            20                  25                  30

Pro Leu Pro Gly
        35

<210> SEQ ID NO 9
<211> LENGTH: 35
<212> TYPE: PRT
<213> ORGANISM: artificial
<220> FEATURE:
<223> OTHER INFORMATION: analog of SEQ ID NO: 2 wherein all amino acids
      are D-amino acids
```

```
<400> SEQUENCE: 9

Lys Arg Gly Phe Gly Lys Lys Leu Arg Lys Arg Leu Lys Lys Phe Arg
1               5                   10                  15

Asn Ser Ile Lys Lys Arg Leu Lys Asn Phe Asn Val Val Ile Pro Ile
            20                  25                  30

Pro Leu Pro
        35

<210> SEQ ID NO 10
<211> LENGTH: 36
<212> TYPE: PRT
<213> ORGANISM: artificial
<220> FEATURE:
<223> OTHER INFORMATION: analog of SEQ ID NO: 1 wherein the N-terminal
      and C-terminal amino acids are D-amino acids

<400> SEQUENCE: 10

Lys Arg Gly Phe Gly Lys Lys Leu Arg Lys Arg Leu Lys Lys Phe Arg
1               5                   10                  15

Asn Ser Ile Lys Lys Arg Leu Lys Asn Phe Asn Val Val Ile Pro Ile
            20                  25                  30

Pro Leu Pro Gly
        35

<210> SEQ ID NO 11
<211> LENGTH: 35
<212> TYPE: PRT
<213> ORGANISM: artificial
<220> FEATURE:
<223> OTHER INFORMATION: analog of SEQ ID NO: 2 wherein the N-terminal
      and C-terminal amino acids are D-amino acids

<400> SEQUENCE: 11

Lys Arg Gly Phe Gly Lys Lys Leu Arg Lys Arg Leu Lys Lys Phe Arg
1               5                   10                  15

Asn Ser Ile Lys Lys Arg Leu Lys Asn Phe Asn Val Val Ile Pro Ile
            20                  25                  30

Pro Leu Pro
        35

<210> SEQ ID NO 12
<211> LENGTH: 36
<212> TYPE: PRT
<213> ORGANISM: artificial
<220> FEATURE:
<223> OTHER INFORMATION: antimicrobial peptide comprising reversed
      sequence of SEQ ID NO: 1

<400> SEQUENCE: 12

Gly Pro Leu Pro Ile Pro Ile Val Val Asn Phe Asn Lys Leu Arg Lys
1               5                   10                  15

Lys Ile Ser Asn Arg Phe Lys Lys Leu Arg Lys Arg Leu Lys Lys Gly
            20                  25                  30

Phe Gly Arg Lys
        35

<210> SEQ ID NO 13
<211> LENGTH: 35
<212> TYPE: PRT
<213> ORGANISM: artificial
<220> FEATURE:
<223> OTHER INFORMATION: antimicrobial peptide comprising reversed
      sequence of SEQ ID NO: 2
```

-continued

```
<400> SEQUENCE: 13

Pro Leu Pro Ile Pro Ile Val Val Asn Phe Asn Lys Leu Arg Lys Lys
1               5                   10                  15

Ile Ser Asn Arg Phe Lys Lys Leu Arg Lys Arg Leu Lys Lys Gly Phe
            20                  25                  30

Gly Arg Lys
        35

<210> SEQ ID NO 14
<211> LENGTH: 36
<212> TYPE: PRT
<213> ORGANISM: artificial
<220> FEATURE:
<223> OTHER INFORMATION: antimicrobial peptide comprising reversed
      sequence of SEQ ID NO: 1 wherein each amino acid is a D-amino acid

<400> SEQUENCE: 14

Gly Pro Leu Pro Ile Pro Ile Val Val Asn Phe Asn Lys Leu Arg Lys
1               5                   10                  15

Lys Ile Ser Asn Arg Phe Lys Lys Leu Arg Lys Arg Leu Lys Lys Gly
            20                  25                  30

Phe Gly Arg Lys
        35

<210> SEQ ID NO 15
<211> LENGTH: 35
<212> TYPE: PRT
<213> ORGANISM: artificial
<220> FEATURE:
<223> OTHER INFORMATION: antimicrobial peptide comprising reversed
      sequence of SEQ ID NO: 2 wherein each amino acid is a D-amino acid

<400> SEQUENCE: 15

Pro Leu Pro Ile Pro Ile Val Val Asn Phe Asn Lys Leu Arg Lys Lys
1               5                   10                  15

Ile Ser Asn Arg Phe Lys Lys Leu Arg Lys Arg Leu Lys Lys Gly Phe
            20                  25                  30

Gly Arg Lys
        35

<210> SEQ ID NO 16
<211> LENGTH: 36
<212> TYPE: PRT
<213> ORGANISM: artificial
<220> FEATURE:
<223> OTHER INFORMATION: antimicrobial peptide comprising reversed
      sequence of SEQ ID NO: 1 wherein the N-terminal and C-terminal
      amino acid residues are D-amino acids

<400> SEQUENCE: 16

Gly Pro Leu Pro Ile Pro Ile Val Val Asn Phe Asn Lys Leu Arg Lys
1               5                   10                  15

Lys Ile Ser Asn Arg Phe Lys Lys Leu Arg Lys Arg Leu Lys Lys Gly
            20                  25                  30

Phe Gly Arg Lys
        35

<210> SEQ ID NO 17
<211> LENGTH: 35
<212> TYPE: PRT
<213> ORGANISM: artificial
<220> FEATURE:
<223> OTHER INFORMATION: antimicrobial peptide comprising reversed
```

-continued sequence of SEQ ID NO: 2 wherein the N-terminal and C-terminal
amino acids residues are D-amino acids

<400> SEQUENCE: 17

Pro Leu Pro Ile Pro Ile Val Val Asn Phe Asn Lys Leu Arg Lys Lys
1               5                   10                  15

Ile Ser Asn Arg Phe Lys Lys Leu Arg Lys Arg Leu Lys Lys Gly Phe
                20                  25                  30

Gly Arg Lys
        35

<210> SEQ ID NO 18
<211> LENGTH: 36
<212> TYPE: PRT
<213> ORGANISM: artificial
<220> FEATURE:
<223> OTHER INFORMATION: antimicrobial peptide derived from Macropus
      eugenii protein

<400> SEQUENCE: 18

Lys Arg Gly Leu Trp Glu Ser Leu Lys Arg Lys Ala Thr Lys Leu Gly
1               5                   10                  15

Asp Asp Ile Arg Asn Thr Leu Arg Asn Phe Lys Ile Lys Phe Pro Val
                20                  25                  30

Pro Arg Gln Gly
        35

<210> SEQ ID NO 19
<211> LENGTH: 35
<212> TYPE: PRT
<213> ORGANISM: artificial
<220> FEATURE:
<223> OTHER INFORMATION: antimicrobial peptide fragment of SEQ ID NO: 18

<400> SEQUENCE: 19

Lys Arg Gly Leu Trp Glu Ser Leu Lys Arg Lys Ala Thr Lys Leu Gly
1               5                   10                  15

Asp Asp Ile Arg Asn Thr Leu Arg Asn Phe Lys Ile Lys Phe Pro Val
                20                  25                  30

Pro Arg Gln
        35

<210> SEQ ID NO 20
<211> LENGTH: 36
<212> TYPE: PRT
<213> ORGANISM: artificial
<220> FEATURE:
<223> OTHER INFORMATION: analog of SEQ ID NO: 18 wherein all amino acids
      are D-amino acids

<400> SEQUENCE: 20

Lys Arg Gly Leu Trp Glu Ser Leu Lys Arg Lys Ala Thr Lys Leu Gly
1               5                   10                  15

Asp Asp Ile Arg Asn Thr Leu Arg Asn Phe Lys Ile Lys Phe Pro Val
                20                  25                  30

Pro Arg Gln Gly
        35

<210> SEQ ID NO 21
<211> LENGTH: 35
<212> TYPE: PRT
<213> ORGANISM: artificial
<220> FEATURE:
<223> OTHER INFORMATION: analog of SEQ ID NO: 19 wherein all amino acids

```
                            are D-amino acids

<400> SEQUENCE: 21

Lys Arg Gly Leu Trp Glu Ser Leu Lys Arg Lys Ala Thr Lys Leu Gly
1               5                   10                  15

Asp Asp Ile Arg Asn Thr Leu Arg Asn Phe Lys Ile Lys Phe Pro Val
            20                  25                  30

Pro Arg Gln
        35

<210> SEQ ID NO 22
<211> LENGTH: 36
<212> TYPE: PRT
<213> ORGANISM: artificial
<220> FEATURE:
<223> OTHER INFORMATION: analog of SEQ ID NO: 18 wherein the N-terminal
      and C-terminal amino acids are D-amino acids

<400> SEQUENCE: 22

Lys Arg Gly Leu Trp Glu Ser Leu Lys Arg Lys Ala Thr Lys Leu Gly
1               5                   10                  15

Asp Asp Ile Arg Asn Thr Leu Arg Asn Phe Lys Ile Lys Phe Pro Val
            20                  25                  30

Pro Arg Gln Gly
        35

<210> SEQ ID NO 23
<211> LENGTH: 35
<212> TYPE: PRT
<213> ORGANISM: artificial
<220> FEATURE:
<223> OTHER INFORMATION: analog of SEQ ID NO: 19 wherein the N-terminal
      and C-terminal amino acids are D-amino acids

<400> SEQUENCE: 23

Lys Arg Gly Leu Trp Glu Ser Leu Lys Arg Lys Ala Thr Lys Leu Gly
1               5                   10                  15

Asp Asp Ile Arg Asn Thr Leu Arg Asn Phe Lys Ile Lys Phe Pro Val
            20                  25                  30

Pro Arg Gln
        35

<210> SEQ ID NO 24
<211> LENGTH: 36
<212> TYPE: PRT
<213> ORGANISM: artificial
<220> FEATURE:
<223> OTHER INFORMATION: antimicrobial peptide comprising reversed
      sequence of SEQ ID NO: 18

<400> SEQUENCE: 24

Gly Gln Arg Pro Val Pro Phe Lys Ile Lys Phe Asn Arg Leu Thr Asn
1               5                   10                  15

Arg Ile Asp Asp Gly Leu Lys Thr Ala Lys Arg Lys Leu Ser Glu Trp
            20                  25                  30

Leu Gly Arg Lys
        35

<210> SEQ ID NO 25
<211> LENGTH: 35
<212> TYPE: PRT
<213> ORGANISM: artificial
<220> FEATURE:
<223> OTHER INFORMATION: antimicrobial peptide comprising reversed
``` sequence of SEQ ID NO: 19

<400> SEQUENCE: 25

Gln Arg Pro Val Pro Phe Lys Ile Lys Phe Asn Arg Leu Thr Asn Arg
1               5                   10                  15

Ile Asp Asp Gly Leu Lys Thr Ala Lys Arg Lys Leu Ser Glu Trp Leu
            20                  25                  30

Gly Arg Lys
        35

<210> SEQ ID NO 26
<211> LENGTH: 36
<212> TYPE: PRT
<213> ORGANISM: artificial
<220> FEATURE:
<223> OTHER INFORMATION: antimicrobial peptide comprising reversed
      sequence of SEQ ID NO: 18 wherein each amino acid is a D-amino
      acid

<400> SEQUENCE: 26

Gly Gln Arg Pro Val Pro Phe Lys Ile Lys Phe Asn Arg Leu Thr Asn
1               5                   10                  15

Arg Ile Asp Asp Gly Leu Lys Thr Ala Lys Arg Lys Leu Ser Glu Trp
            20                  25                  30

Leu Gly Arg Lys
        35

<210> SEQ ID NO 27
<211> LENGTH: 35
<212> TYPE: PRT
<213> ORGANISM: artificial
<220> FEATURE:
<223> OTHER INFORMATION: antimicrobial peptide comprising reversed
      sequence of SEQ ID NO: 19 wherein each amino acid is a D-amino
      acid

<400> SEQUENCE: 27

Gln Arg Pro Val Pro Phe Lys Ile Lys Phe Asn Arg Leu Thr Asn Arg
1               5                   10                  15

Ile Asp Asp Gly Leu Lys Thr Ala Lys Arg Lys Leu Ser Glu Trp Leu
            20                  25                  30

Gly Arg Lys
        35

<210> SEQ ID NO 28
<211> LENGTH: 36
<212> TYPE: PRT
<213> ORGANISM: artificial
<220> FEATURE:
<223> OTHER INFORMATION: antimicrobial peptide comprising reversed
      sequence of SEQ ID NO: 18 wherein the N-terminal and C-terminal
      amino acid residues are D-amino acids

<400> SEQUENCE: 28

Gly Gln Arg Pro Val Pro Phe Lys Ile Lys Phe Asn Arg Leu Thr Asn
1               5                   10                  15

Arg Ile Asp Asp Gly Leu Lys Thr Ala Lys Arg Lys Leu Ser Glu Trp
            20                  25                  30

Leu Gly Arg Lys
        35

<210> SEQ ID NO 29
<211> LENGTH: 35
<212> TYPE: PRT

```
<213> ORGANISM: artificial
<220> FEATURE:
<223> OTHER INFORMATION: antimicrobial peptide comprising reversed
      sequence of SEQ ID NO: 19 wherein the N-terminal and C-terminal
      amino acid residues are D-amino acids

<400> SEQUENCE: 29

Gln Arg Pro Val Pro Phe Lys Ile Lys Phe Asn Arg Leu Thr Asn Arg
1               5                   10                  15

Ile Asp Asp Gly Leu Lys Thr Ala Lys Arg Lys Leu Ser Glu Trp Leu
                20                  25                  30

Gly Arg Lys
        35

<210> SEQ ID NO 30
<211> LENGTH: 44
<212> TYPE: PRT
<213> ORGANISM: artificial
<220> FEATURE:
<223> OTHER INFORMATION: antimicrobial peptide derived from Macropus
      eugenii protein

<400> SEQUENCE: 30

Thr Pro Glu Leu Phe Arg Ser Arg Ser Pro Pro Gly Arg Lys Lys Gly
1               5                   10                  15

Ser Lys Arg His Lys Pro Gly Ser Tyr Ser Val Ile Ala Leu Gly Lys
                20                  25                  30

Pro Gly Val Lys Lys Ser Pro Tyr Met Glu Ala Leu
        35                  40

<210> SEQ ID NO 31
<211> LENGTH: 32
<212> TYPE: PRT
<213> ORGANISM: artificial
<220> FEATURE:
<223> OTHER INFORMATION: antimicrobial peptide fragment of SEQ ID NO: 30

<400> SEQUENCE: 31

Arg Lys Lys Gly Ser Lys Arg His Lys Pro Gly Ser Tyr Ser Val Ile
1               5                   10                  15

Ala Leu Gly Lys Pro Gly Val Lys Lys Ser Pro Tyr Met Glu Ala Leu
                20                  25                  30

<210> SEQ ID NO 32
<211> LENGTH: 23
<212> TYPE: PRT
<213> ORGANISM: artificial
<220> FEATURE:
<223> OTHER INFORMATION: antimicrobial peptide fragment of SEQ ID NO: 30

<400> SEQUENCE: 32

Pro Gly Ser Tyr Ser Val Ile Ala Leu Gly Lys Pro Gly Val Lys Lys
1               5                   10                  15

Ser Pro Tyr Met Glu Ala Leu
        20

<210> SEQ ID NO 33
<211> LENGTH: 19
<212> TYPE: PRT
<213> ORGANISM: artificial
<220> FEATURE:
<223> OTHER INFORMATION: antimicrobial peptide fragment of SEQ ID NO: 30

<400> SEQUENCE: 33

Ser Val Ile Ala Leu Gly Lys Pro Gly Val Lys Lys Ser Pro Tyr Met
```

```
                               1               5                  10                  15
Glu Ala Leu

<210> SEQ ID NO 34
<211> LENGTH: 16
<212> TYPE: PRT
<213> ORGANISM: artificial
<220> FEATURE:
<223> OTHER INFORMATION: antimicrobial peptide fragment of SEQ ID NO: 30

<400> SEQUENCE: 34

Ala Leu Gly Lys Pro Gly Val Lys Lys Ser Pro Tyr Met Glu Ala Leu
1               5                  10                  15

<210> SEQ ID NO 35
<211> LENGTH: 18
<212> TYPE: PRT
<213> ORGANISM: artificial
<220> FEATURE:
<223> OTHER INFORMATION: antimicrobial peptide fragment of SEQ ID NO: 30

<400> SEQUENCE: 35

Ser Val Ile Ala Leu Gly Lys Pro Gly Val Lys Lys Ser Pro Tyr Met
1               5                  10                  15

Glu Ala

<210> SEQ ID NO 36
<211> LENGTH: 32
<212> TYPE: PRT
<213> ORGANISM: artificial
<220> FEATURE:
<223> OTHER INFORMATION: analog of SEQ ID NO: 31 wherein all amino acids
      are D-amino acids

<400> SEQUENCE: 36

Arg Lys Lys Gly Ser Lys Arg His Lys Pro Gly Ser Tyr Ser Val Ile
1               5                  10                  15

Ala Leu Gly Lys Pro Gly Val Lys Lys Ser Pro Tyr Met Glu Ala Leu
                20                  25                  30

<210> SEQ ID NO 37
<211> LENGTH: 32
<212> TYPE: PRT
<213> ORGANISM: artificial
<220> FEATURE:
<223> OTHER INFORMATION: analog of SEQ ID NO: 31 wherein the N-terminal
      and C-terminal amino acids are D-amino acids

<400> SEQUENCE: 37

Arg Lys Lys Gly Ser Lys Arg His Lys Pro Gly Ser Tyr Ser Val Ile
1               5                  10                  15

Ala Leu Gly Lys Pro Gly Val Lys Lys Ser Pro Tyr Met Glu Ala Leu
                20                  25                  30

<210> SEQ ID NO 38
<211> LENGTH: 32
<212> TYPE: PRT
<213> ORGANISM: artificial
<220> FEATURE:
<223> OTHER INFORMATION: antimicrobial peptide comprising reversed
      sequence of SEQ ID NO: 31

<400> SEQUENCE: 38

Leu Ala Glu Met Tyr Pro Ser Lys Lys Val Gly Pro Lys Gly Leu Ala
1               5                  10                  15
```

-continued

```
Ile Val Ser Tyr Ser Gly Pro Lys His Arg Lys Ser Gly Lys Lys Arg
            20                  25                  30

<210> SEQ ID NO 39
<211> LENGTH: 32
<212> TYPE: PRT
<213> ORGANISM: artificial
<220> FEATURE:
<223> OTHER INFORMATION: antimicrobial peptide comprising reversed
      sequence of SEQ ID NO: 31 wherein each amino acid is a D-amino
      acid

<400> SEQUENCE: 39

Leu Ala Glu Met Tyr Pro Ser Lys Lys Val Gly Pro Lys Gly Leu Ala
1               5                   10                  15

Ile Val Ser Tyr Ser Gly Pro Lys His Arg Lys Ser Gly Lys Lys Arg
            20                  25                  30

<210> SEQ ID NO 40
<211> LENGTH: 32
<212> TYPE: PRT
<213> ORGANISM: artificial
<220> FEATURE:
<223> OTHER INFORMATION: antimicrobial peptide comprising reversed
      sequence of SEQ ID NO: 31 wherein the N-terminal and C-terminal
      amino acid residues are D-amino acids

<400> SEQUENCE: 40

Leu Ala Glu Met Tyr Pro Ser Lys Lys Val Gly Pro Lys Gly Leu Ala
1               5                   10                  15

Ile Val Ser Tyr Ser Gly Pro Lys His Arg Lys Ser Gly Lys Lys Arg
            20                  25                  30

<210> SEQ ID NO 41
<211> LENGTH: 9
<212> TYPE: PRT
<213> ORGANISM: artificial
<220> FEATURE:
<223> OTHER INFORMATION: influenza virus HA epitope

<400> SEQUENCE: 41

Tyr Pro Tyr Asp Val Pro Asp Tyr Ala
1               5

<210> SEQ ID NO 42
<211> LENGTH: 14
<212> TYPE: PRT
<213> ORGANISM: artificial
<220> FEATURE:
<223> OTHER INFORMATION: simian virus 5 (SV-5) epitope

<400> SEQUENCE: 42

Gly Lys Pro Ile Pro Asn Pro Leu Leu Gly Leu Asp Ser Thr
1               5                   10

<210> SEQ ID NO 43
<211> LENGTH: 6
<212> TYPE: PRT
<213> ORGANISM: artificial
<220> FEATURE:
<223> OTHER INFORMATION: hexa-histidine tag

<400> SEQUENCE: 43

His His His His His His
1               5

<210> SEQ ID NO 44
```

```
-continued

<211> LENGTH: 10
<212> TYPE: PRT
<213> ORGANISM: artificial
<220> FEATURE:
<223> OTHER INFORMATION: c-myc tag

<400> SEQUENCE: 44

Phe Gln Lys Leu Ile Ser Glu Glu Asp Leu
1               5                   10

<210> SEQ ID NO 45
<211> LENGTH: 9
<212> TYPE: PRT
<213> ORGANISM: artificial
<220> FEATURE:
<223> OTHER INFORMATION: FLAG tag

<400> SEQUENCE: 45

Asp Tyr Lys Asp Asp Asp Asp Lys Cys
1               5

<210> SEQ ID NO 46
<211> LENGTH: 101
<212> TYPE: PRT
<213> ORGANISM: artificial
<220> FEATURE:
<223> OTHER INFORMATION: antimicrobial peptide inhibitor

<400> SEQUENCE: 46

Gln Asp Gln Pro Tyr Gln Asp Val Leu Asn Arg Phe Ile Gln Glu Tyr
1               5                   10                  15

Asn Thr Lys Ser Glu Ser Glu Ser Leu Phe Arg Leu Ser Val Leu Asn
                20                  25                  30

Leu Pro Ser Gln Glu Ser Asn Asp Pro Thr Ala Pro Gln Leu Leu Lys
            35                  40                  45

Phe Thr Ile Arg Glu Thr Val Cys Ser Lys Ser Glu His Arg Asn Pro
 50                 55                  60

Glu Glu Cys Asp Phe Lys Lys Asn Gly Leu Val Glu Glu Cys Ile Gly
65                  70                  75                  80

Thr Val Asp Leu Asp Ser Ser Pro Ser Val Asp Ile Ser Cys Asp
                85                  90                  95

Gly Pro Glu Lys Val
            100

<210> SEQ ID NO 47
<211> LENGTH: 15
<212> TYPE: PRT
<213> ORGANISM: artificial
<220> FEATURE:
<223> OTHER INFORMATION: antimicrobial peptide inhibitor

<400> SEQUENCE: 47

Pro Glu Ala Val Pro Thr Ala Asp Lys Gln Ile Pro Asn Arg Ala
1               5                   10                  15

<210> SEQ ID NO 48
<211> LENGTH: 69
<212> TYPE: PRT
<213> ORGANISM: artificial
<220> FEATURE:
<223> OTHER INFORMATION: antimicrobial peptide inhibitor

<400> SEQUENCE: 48

Pro Leu Ser Ser Leu Ser Gln Thr Ser Thr Ala His Phe Glu Val His
1               5                   10                  15
```

```
Arg Gly Asn Ala Leu Gln Ile Tyr Ser Ser Pro Asn Gln Gly Pro His
             20                  25                  30

Glu Gln Thr Leu Lys Arg Asn Leu Lys Pro Thr Thr Glu Leu Leu Leu
         35                  40                  45

Asp Gln Thr Asp Leu Lys Gln Ser Ser Asn Glu Gln Gly Ile Ala Ala
     50                  55                  60

Ile Ile Leu Thr Pro
 65

<210> SEQ ID NO 49
<211> LENGTH: 126
<212> TYPE: PRT
<213> ORGANISM: artificial
<220> FEATURE:
<223> OTHER INFORMATION: antimicrobial peptide inhibitor

<400> SEQUENCE: 49

Met Arg Gly Leu Thr Met Gln Val Leu Leu Val Leu Gly Leu Leu
  1               5                  10                  15

Ser Leu Met Asn Pro Leu Gly Tyr Ala Gln Asp Gln Pro Tyr Gln Asp
             20                  25                  30

Val Leu Asn Arg Phe Ile Gln Glu Tyr Asn Thr Lys Ser Glu Ser Glu
         35                  40                  45

Ser Leu Phe Arg Leu Ser Val Leu Asn Leu Pro Ser Gln Glu Ser Asn
     50                  55                  60

Asp Pro Thr Ala Pro Gln Leu Leu Lys Phe Thr Ile Arg Glu Thr Val
 65                  70                  75                  80

Cys Ser Lys Ser Glu His Arg Asn Pro Glu Glu Cys Asp Phe Lys Lys
                 85                  90                  95

Asn Gly Leu Val Glu Glu Cys Ile Gly Thr Val Asp Leu Asp Ser Ser
            100                 105                 110

Ser Pro Ser Val Asp Ile Ser Cys Asp Gly Pro Glu Lys Val
        115                 120                 125

<210> SEQ ID NO 50
<211> LENGTH: 21
<212> TYPE: PRT
<213> ORGANISM: artificial
<220> FEATURE:
<223> OTHER INFORMATION: antimicrobial peptide inhibitor

<400> SEQUENCE: 50

Asp Ser Thr Ser Ala Cys Pro Glu Ala Val Pro Thr Ala Asp Lys Gln
  1               5                  10                  15

Ile Pro Asn Arg Ala
             20

<210> SEQ ID NO 51
<211> LENGTH: 85
<212> TYPE: PRT
<213> ORGANISM: artificial
<220> FEATURE:
<223> OTHER INFORMATION: antimicrobial peptide inhibitor

<400> SEQUENCE: 51

Glu His Arg Lys Val Leu Ala Ser Val Ala Ile Ile Ser Thr Gln Ala
  1               5                  10                  15

Pro Leu Ser Ser Leu Ser Gln Thr Ser Thr Ala His Phe Glu Val His
             20                  25                  30

Arg Gly Asn Ala Leu Gln Ile Tyr Ser Ser Pro Asn Gln Gly Pro His
```

```
                          35                  40                  45
Glu Gln Thr Leu Lys Arg Asn Leu Lys Pro Thr Thr Glu Leu Leu Leu
 50                  55                  60

Asp Gln Thr Asp Leu Lys Gln Ser Ser Asn Glu Gln Gly Ile Ala Ala
 65                  70                  75                  80

Ile Ile Leu Thr Pro
                 85

<210> SEQ ID NO 52
<211> LENGTH: 933
<212> TYPE: PRT
<213> ORGANISM: artificial
<220> FEATURE:
<223> OTHER INFORMATION: Staphylococcus aureus

<400> SEQUENCE: 52

Met Asn Met Lys Lys Glu Lys His Ala Ile Arg Lys Lys Ser Ile
 1               5                  10                  15

Gly Val Ala Ser Val Leu Val Gly Thr Leu Ile Gly Phe Gly Leu Leu
                 20                  25                  30

Ser Ser Lys Glu Ala Asp Ala Ser Glu Asn Ser Val Thr Gln Ser Asp
             35                  40                  45

Ser Ala Ser Asn Glu Ser Lys Ser Asn Asp Ser Ser Val Ser Ala
 50                  55                  60

Ala Pro Lys Thr Asp Asp Thr Asn Val Ser Asp Thr Lys Thr Ser Ser
 65                  70                  75                  80

Asn Thr Asn Asn Gly Glu Thr Ser Val Ala Gln Asn Pro Ala Gln Gln
                 85                  90                  95

Glu Thr Thr Gln Ser Ser Ser Thr Asn Ala Thr Thr Glu Glu Thr Pro
            100                 105                 110

Val Thr Gly Glu Ala Thr Thr Thr Thr Asn Gln Ala Asn Thr Pro
            115                 120                 125

Ala Thr Thr Gln Ser Ser Asn Thr Asn Ala Glu Glu Leu Val Asn Gln
            130                 135                 140

Thr Ser Asn Glu Thr Thr Ser Asn Asp Thr Asn Thr Val Ser Ser Val
145                 150                 155                 160

Asn Ser Pro Gln Asn Ser Thr Asn Ala Glu Asn Val Ser Thr Thr Gln
                165                 170                 175

Asp Thr Ser Thr Glu Ala Thr Pro Ser Asn Asn Glu Ser Ala Pro Gln
            180                 185                 190

Ser Thr Asp Ala Ser Asn Lys Asp Val Val Asn Gln Ala Val Asn Thr
            195                 200                 205

Ser Ala Pro Arg Met Arg Ala Phe Ser Leu Ala Ala Val Ala Ala Asp
            210                 215                 220

Ala Pro Ala Ala Gly Thr Asp Ile Thr Asn Gln Leu Thr Asn Val Thr
225                 230                 235                 240

Val Gly Ile Asp Ser Gly Thr Thr Val Tyr Pro His Gln Ala Gly Tyr
                245                 250                 255

Val Lys Leu Asn Tyr Gly Phe Ser Val Pro Asn Ser Ala Val Lys Gly
            260                 265                 270

Asp Thr Phe Lys Ile Thr Val Pro Lys Glu Leu Asn Leu Asn Gly Val
            275                 280                 285

Thr Ser Thr Ala Lys Val Pro Pro Ile Met Ala Gly Asp Gln Val Leu
            290                 295                 300

Ala Asn Gly Val Ile Asp Ser Asp Gly Asn Val Ile Tyr Thr Phe Thr
305                 310                 315                 320
```

-continued

```
Asp Tyr Val Asn Thr Lys Asp Val Lys Ala Thr Leu Thr Met Pro
                325                 330                 335
Ala Tyr Ile Asp Pro Glu Asn Val Lys Lys Thr Gly Asn Val Thr Leu
            340                 345                 350
Ala Thr Gly Ile Gly Ser Thr Thr Ala Asn Lys Thr Val Leu Val Asp
        355                 360                 365
Tyr Glu Lys Tyr Gly Lys Phe Tyr Asn Leu Ser Ile Lys Gly Thr Ile
    370                 375                 380
Asp Gln Ile Asp Lys Thr Asn Asn Thr Tyr Arg Gln Thr Ile Tyr Val
385                 390                 395                 400
Asn Pro Ser Gly Asp Asn Val Ile Ala Pro Val Leu Thr Gly Asn Leu
                405                 410                 415
Lys Pro Asn Thr Asp Ser Asn Ala Leu Ile Asp Gln Gln Asn Thr Ser
            420                 425                 430
Ile Lys Val Tyr Lys Val Asp Asn Ala Ala Asp Leu Ser Glu Ser Tyr
        435                 440                 445
Phe Val Asn Pro Glu Asn Phe Glu Asp Val Thr Asn Ser Val Asn Ile
    450                 455                 460
Thr Phe Pro Asn Pro Asn Gln Tyr Lys Val Glu Phe Asn Thr Pro Asp
465                 470                 475                 480
Asp Gln Ile Thr Thr Pro Tyr Ile Val Val Asn Gly His Ile Asp
                485                 490                 495
Pro Asn Ser Lys Gly Asp Leu Ala Leu Arg Ser Thr Leu Tyr Gly Tyr
            500                 505                 510
Asn Ser Asn Ile Ile Trp Arg Ser Met Ser Trp Asp Asn Glu Val Ala
        515                 520                 525
Phe Asn Asn Gly Ser Gly Ser Gly Asp Gly Ile Asp Lys Pro Val Val
    530                 535                 540
Pro Glu Gln Pro Asp Glu Pro Gly Glu Ile Glu Pro Ile Pro Glu Asp
545                 550                 555                 560
Ser Asp Ser Asp Pro Gly Ser Asp Ser Gly Ser Asp Ser Asn Ser Asp
                565                 570                 575
Ser Gly Ser Asp Ser Gly Ser Asp Ser Thr Ser Asp Ser Gly Ser Asp
            580                 585                 590
Ser Ala Ser Asp Ser Asp Ser Ala Ser Asp Ser Asp Ser Ala Ser Asp
        595                 600                 605
Ser Asp Ser Ala Ser Ser Asp Ser Ala Ser Asp Ser Asp Ser Asp
    610                 615                 620
Asn Asp Ser Asp Ser Asp Ser Asp Ser Asp Ser Asp Ser Asp Ser Asp
625                 630                 635                 640
Ser Asp Ser Asp Ser Asp Ser Asp Ser Asp Ser Asp Ser Asp Ser Asp
                645                 650                 655
Ser Asp Ser Asp Ser Asp Ser Asp Ser Asp Ser Asp Ser Asp Ser Asp
            660                 665                 670
Ser Asp Ser Asp Ser Asp Ser Asp Ser Asp Ser Asp Ser Asp Ser Asp
        675                 680                 685
Ser Asp Ser Asp Ser Asp Ser Asp Ser Asp Ser Asp Ser Asp Ser Asp
    690                 695                 700
Ser Asp Ser Asp Ser Asp Ser Asp Ser Asp Ser Asp Ser Asp Ser Asp
705                 710                 715                 720
Ser Asp Ser Asp Ser Asp Ser Asp Ser Asp Ser Asp Ser Asp Ser Asp
                725                 730                 735
Ser Asp Ser Asp Ser Asp Ser Asp Ser Asp Ser Asp Ser Asp Ser Asp
```

-continued

```
                 740                 745                 750
Ser Asp Ser Asp Ser Asp Ser Asp Ser Asp Ser Asp Ser Ala
                 755                 760                 765
Ser Asp Ser Asp Ser Asp Ser Asp Ser Asp Ser Asp Ser Asp
             770                 775                 780
Ser Asp Ser Asp Ser Asp Ser Asp Ser Asp Ser Asp Ser Asp
785                 790                 795                 800
Ser Asp Ser Asp Ser Asp Glu Ser Asp Ser Asp Glu Ser Asp
                 805                 810                 815
Ser Asp Ser Asp Ser Asp Ser Asp Ser Asp Ser Asp Ser Asp
             820                 825                 830
Ser Asp Ser Asp Ser Ala Ser Asp Ser Asp Ser Gly Ser Asp Ser Asp
             835                 840                 845
Ser Ser Ser Asp Ser Asp Ser Glu Ser Asp Ser Asn Ser Asp Ser Glu
         850                 855                 860
Ser Gly Ser Asn Asn Val Val Pro Pro Asn Ser Pro Lys Asn Gly
865                 870                 875                 880
Thr Asn Ala Ser Asn Lys Asn Glu Ala Lys Asp Ser Lys Glu Pro Leu
                 885                 890                 895
Pro Asp Thr Gly Ser Glu Asp Glu Ala Asn Thr Ser Leu Ile Trp Gly
             900                 905                 910
Leu Leu Ala Ser Ile Gly Ser Leu Leu Leu Phe Arg Arg Lys Lys Glu
         915                 920                 925
Asn Lys Asp Lys Lys
     930
```

<210> SEQ ID NO 53
<211> LENGTH: 294
<212> TYPE: PRT
<213> ORGANISM: artificial
<220> FEATURE:
<223> OTHER INFORMATION: Pseudimonas aeruginosa

<400> SEQUENCE: 53

```
Met Glu Val Arg Asn Leu Asn Ala Ala Arg Glu Leu Phe Leu Asp Glu
1               5                   10                  15
Leu Leu Ala Ala Ser Ala Ala Pro Ala Ser Ala Glu Gln Glu Glu Leu
             20                  25                  30
Leu Ala Leu Leu Arg Ser Glu Arg Ile Val Leu Ala His Ala Gly Gln
         35                  40                  45
Pro Leu Ser Glu Ala Gln Val Leu Lys Ala Leu Ala Trp Leu Leu Ala
     50                  55                  60
Ala Asn Pro Ser Ala Pro Pro Gly Gln Gly Leu Glu Val Leu Arg Glu
65                  70                  75                  80
Val Leu Gln Ala Arg Arg Gln Pro Gly Ala Gln Trp Asp Leu Arg Glu
                 85                  90                  95
Phe Leu Val Ser Ala Tyr Phe Ser Leu His Gly Arg Leu Asp Glu Asp
                 100                 105                 110
Val Ile Gly Val Tyr Lys Asp Val Leu Gln Thr Gln Asp Gly Lys Arg
             115                 120                 125
Lys Ala Leu Leu Asp Glu Leu Lys Ala Leu Thr Ala Glu Leu Lys Val
         130                 135                 140
Tyr Ser Val Ile Gln Ser Gln Ile Asn Ala Ala Leu Ser Ala Lys Gln
145                 150                 155                 160
Gly Ile Arg Ile Asp Ala Gly Gly Ile Asp Leu Val Asp Pro Thr Leu
                 165                 170                 175
```

Tyr Gly Tyr Ala Val Gly Asp Pro Arg Trp Lys Asp Ser Pro Glu Tyr
            180                 185                 190

Ala Leu Leu Ser Asn Leu Asp Thr Phe Ser Gly Lys Leu Ser Ile Lys
            195                 200                 205

Asp Phe Leu Ser Gly Ser Pro Lys Gln Ser Gly Glu Leu Lys Gly Leu
    210                 215                 220

Ser Asp Glu Tyr Pro Phe Glu Lys Asp Asn Asn Pro Val Gly Asn Phe
225                 230                 235                 240

Ala Thr Thr Val Ser Asp Arg Ser Arg Pro Leu Asn Asp Lys Val Asn
            245                 250                 255

Glu Lys Thr Thr Leu Leu Asn Asp Thr Ser Ser Arg Tyr Asn Ser Ala
            260                 265                 270

Val Glu Ala Leu Asn Arg Phe Ile Gln Lys Tyr Asp Ser Val Leu Arg
            275                 280                 285

Asp Ile Leu Ser Ala Ile
            290

<210> SEQ ID NO 54
<211> LENGTH: 1664
<212> TYPE: PRT
<213> ORGANISM: artificial
<220> FEATURE:
<223> OTHER INFORMATION: Candida albicans

<400> SEQUENCE: 54

Met Asn Ser Thr Pro Ser Lys Leu Leu Pro Ile Asp Lys His Ser His
1               5                   10                  15

Leu Gln Leu Gln Pro Gln Ser Ser Ser Ala Ser Ile Phe Asn Ser Pro
            20                  25                  30

Thr Lys Pro Leu Asn Phe Pro Arg Thr Asn Ser Lys Pro Ser Leu Asp
        35                  40                  45

Pro Asn Ser Ser Ser Asp Thr Tyr Thr Ser Glu Gln Asp Gln Glu Lys
    50                  55                  60

Gly Lys Glu Glu Lys Lys Asp Thr Ala Phe Gln Thr Ser Phe Asp Arg
65                  70                  75                  80

Asn Phe Asp Leu Asp Asn Ser Ile Asp Ile Gln Gln Thr Ile Gln His
                85                  90                  95

Gln Gln Gln Gln Pro Gln Gln Gln Gln Leu Ser Gln Thr Asp Asn
            100                 105                 110

Asn Leu Ile Asp Glu Phe Ser Phe Gln Thr Pro Met Thr Ser Thr Leu
        115                 120                 125

Asp Leu Thr Lys Gln Asn Pro Thr Val Asp Lys Val Asn Glu Asn His
    130                 135                 140

Ala Pro Thr Tyr Ile Asn Thr Ser Pro Asn Lys Ser Ile Met Lys Lys
145                 150                 155                 160

Ala Thr Pro Lys Ala Ser Pro Lys Lys Val Ala Phe Thr Val Thr Asn
                165                 170                 175

Pro Glu Ile His His Tyr Pro Asp Asn Arg Val Glu Glu Asp Gln
            180                 185                 190

Ser Gln Gln Lys Glu Asp Ser Val Glu Pro Leu Ile Gln His Gln
        195                 200                 205

Trp Lys Asp Pro Ser Gln Phe Asn Tyr Ser Asp Glu Asp Thr Asn Ala
    210                 215                 220

Ser Val Pro Pro Thr Pro Pro Leu His Thr Thr Lys Pro Thr Phe Ala
225                 230                 235                 240

-continued

```
Gln Leu Leu Asn Lys Asn Asn Glu Val Asn Ser Pro Glu Ala Leu
                245                 250                 255

Thr Asp Met Lys Leu Lys Arg Glu Asn Phe Ser Asn Leu Ser Leu Asp
            260                 265                 270

Glu Lys Val Asn Leu Tyr Leu Ser Pro Thr Asn Asn Asn Ser Lys
            275                 280                 285

Asn Val Ser Asp Met Asp Ser His Leu Gln Asn Leu Gln Asp Ala Ser
        290                 295                 300

Lys Asn Lys Thr Asn Glu Asn Ile His Asn Leu Ser Phe Ala Leu Lys
305                 310                 315                 320

Ala Pro Lys Asn Asp Ile Glu Asn Pro Leu Asn Ser Leu Thr Asn Ala
                325                 330                 335

Asp Ile Ser Leu Arg Ser Ser Gly Ser Ser Gln Ser Ser Leu Gln Ser
            340                 345                 350

Leu Arg Asn Asp Asn Arg Val Leu Glu Ser Val Pro Gly Ser Pro Lys
        355                 360                 365

Lys Val Asn Pro Gly Leu Ser Leu Asn Asp Gly Ile Lys Gly Phe Ser
    370                 375                 380

Asp Glu Val Val Glu Ser Leu Leu Pro Arg Asp Leu Ser Arg Asp Lys
385                 390                 395                 400

Leu Glu Thr Thr Lys Glu His Asp Ala Pro Glu His Asn Asn Glu Asn
                405                 410                 415

Phe Ile Asp Ala Lys Ser Thr Asn Thr Asn Lys Gly Gln Leu Leu Val
            420                 425                 430

Ser Ser Asp Asp His Leu Asp Ser Phe Asp Arg Ser Tyr Asn His Thr
        435                 440                 445

Glu Gln Ser Ile Leu Asn Leu Leu Asn Ser Ala Ser Gln Ser Gln Ile
    450                 455                 460

Ser Leu Asn Ala Leu Glu Lys Gln Arg Gln Thr Gln Glu Gln Glu Gln
465                 470                 475                 480

Thr Gln Ala Ala Glu Pro Glu Glu Thr Ser Phe Ser Asp Asn Ile
                485                 490                 495

Lys Val Lys Gln Glu Pro Lys Ser Asn Leu Glu Phe Val Lys Val Thr
            500                 505                 510

Ile Lys Lys Glu Pro Val Ser Ala Thr Glu Ile Lys Ala Pro Lys Arg
        515                 520                 525

Glu Phe Ser Ser Arg Ile Leu Arg Ile Lys Asn Glu Asp Glu Ile Ala
    530                 535                 540

Glu Pro Ala Asp Ile His Pro Lys Lys Glu Asn Glu Ala Asn Ser His
545                 550                 555                 560

Val Glu Asp Thr Asp Ala Leu Leu Lys Lys Ala Leu Asn Asp Asp Glu
                565                 570                 575

Glu Ser Asp Thr Thr Gln Asn Ser Thr Lys Met Ser Ile Arg Phe His
            580                 585                 590

Ile Asp Ser Asp Trp Lys Leu Glu Asp Ser Asn Asp Gly Asp Arg Glu
        595                 600                 605

Asp Asn Asp Asp Ile Ser Arg Phe Glu Lys Ser Asp Ile Leu Asn Asp
    610                 615                 620

Val Ser Gln Thr Ser Asp Ile Ile Gly Asp Lys Tyr Gly Asn Ser Ser
625                 630                 635                 640

Ser Glu Ile Thr Thr Lys Thr Leu Ala Pro Pro Arg Ser Asp Asn Asn
                645                 650                 655

Asp Lys Glu Asn Ser Lys Ser Leu Glu Asp Pro Ala Asn Asn Glu Ser
            660                 665                 670
```

```
Leu Gln Gln Gln Leu Glu Val Pro His Thr Lys Glu Asp Asp Ser Ile
            675                 680                 685
Leu Ala Asn Ser Ser Asn Ile Ala Pro Pro Glu Glu Leu Thr Leu Pro
        690                 695                 700
Val Val Glu Ala Asn Asp Tyr Ser Ser Phe Asp Val Thr Lys Thr
705                 710                 715                 720
Phe Asp Ala Tyr Ser Ser Phe Glu Glu Ser Leu Ser Arg His Glu
            725                 730                 735
Thr Asp Ser Lys Pro Ile Asn Phe Ile Ser Ile Trp His Lys Gln Glu
            740                 745                 750
Lys Gln Lys Lys His Gln Ile His Lys Val Pro Thr Lys Gln Ile Ile
            755                 760                 765
Ala Ser Tyr Gln Gln Tyr Lys Asn Glu Gln Glu Ser Arg Val Thr Ser
        770                 775                 780
Asp Lys Val Lys Ile Pro Asn Ala Ile Gln Phe Lys Lys Phe Lys Glu
785                 790                 795                 800
Val Asn Val Met Ser Arg Arg Val Val Ser Pro Asp Met Asp Asp Leu
            805                 810                 815
Asn Val Ser Gln Phe Leu Pro Glu Leu Ser Glu Asp Ser Gly Phe Lys
            820                 825                 830
Asp Leu Asn Phe Ala Asn Tyr Ser Asn Asn Thr Asn Arg Pro Arg Ser
            835                 840                 845
Phe Thr Pro Leu Ser Thr Lys Asn Val Leu Ser Asn Ile Asp Asn Asp
        850                 855                 860
Pro Asn Val Val Glu Pro Pro Glu Pro Lys Ser Tyr Ala Glu Ile Arg
865                 870                 875                 880
Asn Ala Arg Arg Leu Ser Ala Asn Lys Ala Ala Pro Asn Gln Ala Pro
            885                 890                 895
Pro Leu Pro Pro Gln Arg Gln Pro Ser Ser Thr Arg Ser Asn Ser Asn
            900                 905                 910
Lys Arg Val Ser Arg Phe Arg Val Pro Thr Phe Glu Ile Arg Arg Thr
        915                 920                 925
Ser Ser Ala Leu Ala Pro Cys Asp Met Tyr Asn Asp Ile Phe Asp Asp
        930                 935                 940
Phe Gly Ala Gly Ser Lys Pro Thr Ile Lys Ala Glu Gly Met Lys Thr
945                 950                 955                 960
Leu Pro Ser Met Asp Lys Asp Asp Val Lys Arg Ile Leu Asn Ala Lys
            965                 970                 975
Lys Gly Val Thr Gln Asp Glu Tyr Ile Asn Ala Lys Leu Val Asp Gln
            980                 985                 990
Lys Pro Lys Lys Asn Ser Ile Val Thr Asp Pro Glu Asp Arg Tyr Glu
            995                 1000                1005
Glu Leu Gln Gln Thr Ala Ser Ile His Asn Ala Thr Ile Asp Ser
        1010                1015                1020
Ser Ile Tyr Gly Arg Pro Asp Ser Ile Ser Thr Asp Met Leu Pro
        1025                1030                1035
Tyr Leu Ser Asp Glu Leu Lys Lys Pro Pro Thr Ala Leu Leu Ser
        1040                1045                1050
Ala Asp Arg Leu Phe Met Glu Gln Glu Val His Pro Leu Arg Ser
        1055                1060                1065
Asn Ser Val Leu Val His Pro Gly Ala Gly Ala Ala Thr Asn Ser
        1070                1075                1080
Ser Met Leu Pro Glu Pro Asp Phe Glu Leu Ile Asn Ser Pro Ala
```

-continued

```
            1085                1090                1095
Arg Asn Val Ser Asn Ser Asp Asn Val Ala Ile Ser Gly Asn
    1100                1105                1110
Ala Ser Thr Ile Ser Phe Asn Gln Leu Asp Met Asn Phe Asp Asp
    1115                1120                1125
Gln Ala Thr Ile Gly Gln Lys Ile Gln Glu Gln Pro Ala Ser Lys
    1130                1135                1140
Ser Ala Asn Thr Val Arg Gly Asp Asp Asp Gly Leu Ala Ser Ala
    1145                1150                1155
Pro Glu Thr Pro Arg Thr Pro Thr Lys Lys Glu Ser Ile Ser Ser
    1160                1165                1170
Lys Pro Ala Lys Leu Ser Ser Ala Ser Pro Arg Lys Ser Pro Ile
    1175                1180                1185
Lys Ile Gly Ser Pro Val Arg Val Ile Lys Lys Asn Gly Ser Ile
    1190                1195                1200
Ala Gly Ile Glu Pro Ile Pro Lys Ala Thr His Lys Pro Lys Lys
    1205                1210                1215
Ser Phe Gln Gly Asn Glu Ile Ser Asn His Lys Val Arg Asp Gly
    1220                1225                1230
Gly Ile Ser Pro Ser Ser Gly Ser Glu His Gln Gln His Asn Pro
    1235                1240                1245
Ser Met Val Ser Val Pro Ser Gln Tyr Thr Asp Ala Thr Ser Thr
    1250                1255                1260
Val Pro Asp Glu Asn Lys Asp Val Gln His Lys Pro Arg Glu Lys
    1265                1270                1275
Gln Lys Gln Lys His His His Arg His His His His His His Lys
    1280                1285                1290
Gln Lys Thr Asp Ile Pro Gly Val Val Asp Asp Glu Ile Pro Asp
    1295                1300                1305
Val Gly Leu Gln Glu Arg Gly Lys Leu Phe Phe Arg Val Leu Gly
    1310                1315                1320
Ile Lys Asn Ile Asn Leu Pro Asp Ile Asn Thr His Lys Gly Arg
    1325                1330                1335
Phe Thr Leu Thr Leu Asp Asn Gly Val His Cys Val Thr Thr Pro
    1340                1345                1350
Glu Tyr Asn Met Asp Asp His Asn Val Ala Ile Gly Lys Glu Phe
    1355                1360                1365
Glu Leu Thr Val Ala Asp Ser Leu Glu Phe Ile Leu Thr Leu Lys
    1370                1375                1380
Ala Ser Tyr Glu Lys Pro Arg Gly Thr Leu Val Glu Val Thr Glu
    1385                1390                1395
Lys Lys Val Val Lys Ser Arg Asn Arg Leu Ser Arg Leu Phe Gly
    1400                1405                1410
Ser Lys Asp Ile Ile Thr Thr Thr Lys Phe Val Pro Thr Glu Val
    1415                1420                1425
Lys Asp Thr Trp Ala Asn Lys Phe Ala Pro Asp Gly Ser Phe Ala
    1430                1435                1440
Arg Cys Tyr Ile Asp Leu Gln Gln Phe Glu Asp Gln Ile Thr Gly
    1445                1450                1455
Lys Ala Ser Gln Phe Asp Leu Asn Cys Phe Asn Glu Trp Glu Thr
    1460                1465                1470
Met Ser Asn Gly Asn Gln Pro Met Lys Arg Gly Lys Pro Tyr Lys
    1475                1480                1485
```

```
Ile Ala Gln Leu Glu Val Lys Met Leu Tyr Val Pro Arg Ser Asp
    1490            1495            1500

Pro Arg Glu Ile Leu Pro Thr Ser Ile Arg Ser Ala Tyr Glu Ser
    1505            1510            1515

Ile Asn Glu Leu Asn Asn Glu Gln Asn Asn Tyr Phe Glu Gly Tyr
    1520            1525            1530

Leu His Gln Glu Gly Gly Asp Cys Pro Ile Phe Lys Lys Arg Phe
    1535            1540            1545

Phe Lys Leu Met Gly Thr Ser Leu Leu Ala His Ser Glu Ile Ser
    1550            1555            1560

His Lys Thr Arg Ala Lys Ile Asn Leu Ser Lys Val Val Asp Leu
    1565            1570            1575

Ile Tyr Val Asp Lys Glu Asn Ile Asp Arg Ser Asn His Arg Asn
    1580            1585            1590

Phe Ser Asp Val Leu Leu Leu Asp His Ala Phe Lys Ile Lys Phe
    1595            1600            1605

Ala Asn Gly Glu Leu Ile Asp Phe Cys Ala Pro Asn Lys His Glu
    1610            1615            1620

Met Lys Ile Trp Ile Gln Asn Leu Gln Glu Ile Ile Tyr Arg Asn
    1625            1630            1635

Arg Phe Arg Arg Gln Pro Trp Val Asn Leu Met Leu Gln Gln Gln
    1640            1645            1650

Gln Gln Gln Gln Gln Gln Gln Ser Ser Gln Gln
    1655            1660
```